US012705737B2

(12) United States Patent
Mina et al.

(10) Patent No.: US 12,705,737 B2
(45) Date of Patent: Aug. 11, 2026

(54) SYSTEMS, METHODS, AND DEVICES FOR AN INTEGRATED TELEHEALTH PLATFORM

(71) Applicant: EMED LABS, LLC, Miami, FL (US)

(72) Inventors: Michael J. Mina, Newton, MA (US); Sam Miller, Hollywood, FL (US); John Ray Permenter, Miami, FL (US); Gregory E. Page, Fort Lauderdale, FL (US); Raymond Glenn DuBois, Jr., Palm City, FL (US); Eduardo Linares Padron, Hialeah, FL (US); Zachary Carl Nienstedt, Arden, NC (US); John Andrew Sands, Weston, FL (US); Jatniel Viera, Miramar, FL (US); Michael J. Ferro, Jr., Palm Beach, FL (US); Tatiana Souslova, Tampa, FL (US); Kurt R. Hammond, Evanston, IL (US); Igor Javier Rodriguez, Miami, FL (US)

( * ) Notice: Subject to any disclaimer, the term of this patent is extended or adjusted under 35 U.S.C. 154(b) by 180 days.

(21) Appl. No.: 18/395,460

(22) Filed: Dec. 22, 2023

(65) Prior Publication Data

US 2024/0212140 A1 Jun. 27, 2024

Related U.S. Application Data

(60) Provisional application No. 63/493,205, filed on Mar. 30, 2023, provisional application No. 63/487,800,
(Continued)

(51) Int. Cl.
*G06T 7/00* (2017.01)
*G06T 3/18* (2024.01)
(Continued)

(52) U.S. Cl.
CPC .............. *G06T 7/0012* (2013.01); *G06T 3/18* (2024.01); *G06T 5/20* (2013.01); *G06T 5/73* (2024.01);
(Continued)

(58) Field of Classification Search
CPC .......... G06T 7/0012; G06T 3/18; G06T 5/20; G06T 5/73; G06T 5/90; G06T 7/337;
(Continued)

(56) References Cited

U.S. PATENT DOCUMENTS 3,282,114 A 11/1966 Rodney
5,084,005 A 1/1992 Kachigian
(Continued)

FOREIGN PATENT DOCUMENTS

CN 103153248 A 6/2013
CN 103870688 A 6/2014
(Continued)

OTHER PUBLICATIONS

File history of U.S. Appl. No. 63/477,072, filed Dec. 23, 2022.
(Continued)

*Primary Examiner* — Stephen P Coleman
(74) *Attorney, Agent, or Firm* — Ashurst Perkins Coie US LLP

(57) ABSTRACT

Systems, methods, and devices for operating an integrated telehealth platform are disclosed herein. In some embodiments, the integrated telehealth platform provides telehealth kits and associated services and sessions, such as diagnostic testing, temperature measurement, and drug screening, to users. The platform can guide the user through the steps of performing such sessions. The platform can analyze the session results, such as a thermometer reading, and/or coordinate delivery of the telehealth kit to a laboratory for further analysis. Based on the analysis result, the platform can
(Continued)

provide microbenefits to the user in the form of, for example, discounted or free medication. The platform can communicate with users, proctors, providers, pharmacies, and other entities. The platform can also unlock or lock vehicles based on a drug screening test performed by a potential vehicle operator prior to operation of the vehicle.

20 Claims, 32 Drawing Sheets

Related U.S. Application Data filed on Mar. 1, 2023, provisional application No. 63/486,887, filed on Feb. 24, 2023, provisional application No. 63/477,072, filed on Dec. 23, 2022, provisional application No. 63/477,134, filed on Dec. 23, 2022, provisional application No. 63/477,099, filed on Dec. 23, 2022.

(51) Int. Cl.

| | |
|---|---|
| ***G06T 5/20*** | (2006.01) |
| ***G06T 5/73*** | (2024.01) |
| ***G06T 5/90*** | (2024.01) |
| ***G06T 7/33*** | (2017.01) |
| ***G06T 7/90*** | (2017.01) |
| ***G16H 30/40*** | (2018.01) |
| ***G16H 40/67*** | (2018.01) |

(52) U.S. Cl.

CPC ................ *G06T 5/90* (2024.01); *G06T 7/337* (2017.01); *G06T 7/90* (2017.01); *G16H 30/40* (2018.01); *G16H 40/67* (2018.01); *G06T 2207/10024* (2013.01); *G06T 2207/20132* (2013.01); *G06T 2207/20192* (2013.01); *G06V 2201/03* (2022.01)

(58) Field of Classification Search

CPC ............. G06T 7/90; G06T 2207/10024; G06T 2207/20132; G06T 2207/20192; G16H 30/40; G16H 40/67; G06V 2201/03

USPC .......................................................... 382/128

See application file for complete search history.

(56) References Cited

U.S. PATENT DOCUMENTS

| | | | |
|---|---|---|---|
| 5,915,973 | A | 6/1999 | Hoehn-Saric et al. |
| 5,999,525 | A | 12/1999 | Krishnaswamy et al. |
| 7,110,525 | B1 | 9/2006 | Heller et al. |
| 7,176,936 | B2 | 2/2007 | Sauer et al. |
| 7,491,198 | B2 | 2/2009 | Kockro |
| 7,662,113 | B2 | 2/2010 | Pearl et al. |
| 8,059,892 | B1 | 11/2011 | Fan |
| 8,108,190 | B2 | 1/2012 | Riener et al. |
| 8,253,778 | B2 | 8/2012 | Atsushi |
| 8,314,815 | B2 | 11/2012 | Navab et al. |
| 8,485,038 | B2 | 7/2013 | Sengupta et al. |
| 8,520,080 | B2 | 8/2013 | Havens et al. |
| 8,611,988 | B2 | 12/2013 | Miyamoto |
| 8,713,130 | B2 | 4/2014 | Logan et al. |
| 8,768,022 | B2 | 7/2014 | Miga et al. |
| 8,814,691 | B2 | 8/2014 | Haddick et al. |
| 8,911,358 | B2 | 12/2014 | Koninckx et al. |
| 8,948,935 | B1 | 2/2015 | Peeters et al. |
| 8,982,156 | B2 | 3/2015 | Maggiore |
| 9,030,446 | B2 | 5/2015 | Mistry et al. |
| 9,082,319 | B2 | 7/2015 | Shimada et al. |
| 9,111,383 | B2 | 8/2015 | Fein et al. |
| 9,256,711 | B2 | 2/2016 | Horseman |
| 9,262,743 | B2 | 2/2016 | Heins et al. |
| 9,285,871 | B2 | 3/2016 | Geisner et al. |
| 9,338,622 | B2 | 5/2016 | Bjontegard |
| 9,345,957 | B2 | 5/2016 | Geisner et al. |
| 9,380,177 | B1 | 6/2016 | Rao et al. |
| 9,424,761 | B2 | 8/2016 | Tuchschmid et al. |
| 9,498,132 | B2 | 11/2016 | Maier-Hein et al. |
| 9,501,919 | B2 | 11/2016 | Laett et al. |
| 9,547,917 | B2 | 1/2017 | Zamer |
| 9,563,266 | B2 | 2/2017 | Banerjee et al. |
| 9,600,934 | B2 | 3/2017 | Odessky et al. |
| 9,606,992 | B2 | 3/2017 | Geisner et al. |
| 9,648,436 | B2 | 5/2017 | Kraft et al. |
| 9,788,714 | B2 | 10/2017 | Krueger |
| 9,836,888 | B2 | 12/2017 | Skidmore |
| 9,877,642 | B2 | 1/2018 | Duret |
| 9,886,458 | B2 | 2/2018 | Jung et al. |
| 9,892,561 | B2 | 2/2018 | Choukroun et al. |
| 9,898,662 | B2 | 2/2018 | Tsuda et al. |
| 9,916,002 | B2 | 3/2018 | Petrovskaya et al. |
| 9,972,137 | B2 | 5/2018 | Petrovskaya et al. |
| 10,013,896 | B2 | 7/2018 | Feins et al. |
| 10,026,328 | B2 | 7/2018 | Knoche et al. |
| 10,052,026 | B1 | 8/2018 | Tran |
| 10,106,172 | B2 | 10/2018 | Wingfield et al. |
| 10,108,266 | B2 | 10/2018 | Banerjee et al. |
| 10,127,734 | B2 | 11/2018 | Stroila |
| 10,156,900 | B2 | 12/2018 | Publicover et al. |
| 10,197,803 | B2 | 2/2019 | Badiali et al. |
| 10,216,957 | B2 | 2/2019 | Jung et al. |
| 10,224,059 | B2 | 3/2019 | Childress et al. |
| 10,231,614 | B2 | 3/2019 | Krueger |
| 10,244,198 | B2 | 3/2019 | Cizerle |
| 10,249,042 | B2 | 4/2019 | Jung et al. |
| 10,295,815 | B2 | 5/2019 | Romanowski et al. |
| 10,322,313 | B2 | 6/2019 | Mckirdy |
| 10,346,889 | B1 | 7/2019 | Reiss et al. |
| 10,386,918 | B2 | 8/2019 | Shin et al. |
| 10,430,985 | B2 | 10/2019 | Harrises et al. |
| 10,474,233 | B2 | 11/2019 | Swaminathan et al. |
| 10,475,533 | B2 | 11/2019 | Hanina et al. |
| 10,511,597 | B1 | 12/2019 | Phillips et al. |
| 10,524,715 | B2 | 1/2020 | Sahin |
| 10,535,202 | B2 | 1/2020 | Schmirler et al. |
| 10,540,776 | B2 | 1/2020 | Tran et al. |
| 10,559,117 | B2 | 2/2020 | Kaeser et al. |
| 10,593,092 | B2 | 3/2020 | Solomon |
| 10,596,573 | B2 | 3/2020 | Tamir |
| 10,643,210 | B2 | 5/2020 | Smith et al. |
| 10,660,522 | B2 | 5/2020 | Redei |
| 10,664,572 | B2 | 5/2020 | Bitran et al. |
| 10,758,209 | B2 | 9/2020 | Boctor et al. |
| 10,788,791 | B2 | 9/2020 | Gelman et al. |
| 10,802,695 | B2 | 10/2020 | Daniels et al. |
| 10,824,310 | B2 | 11/2020 | Acharya et al. |
| 10,832,488 | B2 | 11/2020 | Petrovskaya et al. |
| 10,849,688 | B2 | 12/2020 | Rios et al. |
| 10,853,761 | B1 | 12/2020 | Bentley et al. |
| 10,885,530 | B2 | 1/2021 | Mercury et al. |
| 10,888,389 | B2 | 1/2021 | Draelos et al. |
| 10,892,052 | B2 | 1/2021 | Jordan et al. |
| 10,910,016 | B2 | 2/2021 | Rothschild et al. |
| 10,932,705 | B2 | 3/2021 | Muhsin et al. |
| 10,943,407 | B1 | 3/2021 | Morgan et al. |
| 10,945,807 | B2 | 3/2021 | Gibby et al. |
| 10,957,111 | B2 | 3/2021 | Weisman et al. |
| 10,984,910 | B2 | 4/2021 | Burkholz et al. |
| 10,991,185 | B1 | 4/2021 | Luthra et al. |
| 10,991,190 | B1 | 4/2021 | Luthra et al. |
| 10,991,461 | B2 | 4/2021 | Divine et al. |
| 11,004,271 | B2 | 5/2021 | Cvetko et al. |
| 11,017,694 | B2 | 5/2021 | Buras et al. |
| 11,082,661 | B1 | 8/2021 | Pollefeys |
| 11,152,093 | B1 | 10/2021 | Hopen et al. |
| 11,194,995 | B1 | 12/2021 | Profida Ferreira |
| 11,211,162 | B1 | 12/2021 | Weiler et al. |
| 11,219,428 | B2 | 1/2022 | Burkholz et al. |
| 11,257,572 | B1 | 2/2022 | Narke et al. |
| 11,270,235 | B1 | 3/2022 | Daianu et al. |
| 11,289,196 | B1 | 3/2022 | Ferro, Jr. et al. |
| 11,315,053 | B1 | 4/2022 | Powell et al. |

(56) References Cited

U.S. PATENT DOCUMENTS 11,322,260 B1 5/2022 Jain et al.
11,367,530 B1 6/2022 Ferro, Jr. et al.
11,369,454 B1 6/2022 Ferro, Jr. et al.
11,373,756 B1 6/2022 Ferro, Jr. et al.
11,393,586 B1 7/2022 Ferro, Jr. et al.
11,410,773 B2 8/2022 Ferro et al.
11,423,697 B1 8/2022 Wucher et al.
11,440,014 B2 9/2022 Kedia et al.
11,468,980 B2 10/2022 Adiri et al.
11,494,571 B2 11/2022 Cooper
11,515,037 B2 11/2022 Ferro, Jr. et al.
11,521,736 B1 12/2022 Gastfriend et al.
11,568,988 B2 1/2023 Ferro, Jr. et al.
11,605,459 B2 3/2023 Ferro, Jr. et al.
11,610,682 B2 3/2023 Ferro et al.
11,615,888 B2 3/2023 Ferro, Jr. et al.
11,623,114 B2 4/2023 Mohieldin et al.
11,651,405 B1 5/2023 Gray et al.
11,763,942 B2 9/2023 Ferro, Jr. et al.
11,798,684 B2 10/2023 Ferro, Jr. et al.
11,804,299 B2 10/2023 Ferro, Jr. et al.
11,810,668 B2 11/2023 Ferro, Jr. et al.
11,854,698 B2 12/2023 Ferro, Jr. et al.
11,869,659 B2 1/2024 Ferro, Jr. et al.
11,875,896 B2 1/2024 Ferro, Jr. et al.
11,894,137 B2 2/2024 Ferro, Jr. et al.
11,894,138 B2 2/2024 Ferro, Jr. et al.
11,929,168 B2 3/2024 Ferro, Jr. et al.
11,942,218 B2 3/2024 Ferro, Jr. et al.
11,955,239 B2 4/2024 Ferro, Jr. et al.
12,014,829 B2 6/2024 Kramer et al.
12,020,814 B1 6/2024 Mcnair et al.
12,073,933 B2 8/2024 Levy
12,094,606 B2 9/2024 Ferro, Jr. et al.
12,119,112 B1 10/2024 Solie
12,315,642 B2 5/2025 Ferro et al.
2004/0151379 A1 8/2004 Kim et al.
2005/0015115 A1 1/2005 Sullivan et al.
2005/0277872 A1 12/2005 Colby et al.
2007/0048723 A1 3/2007 Brewer et al.
2008/0102435 A1 5/2008 Rogers et al.
2008/0299648 A1 12/2008 Tomer
2009/0004055 A1 1/2009 Darrigrand et al.
2009/0263775 A1 10/2009 Ullrich
2010/0121156 A1 5/2010 Yoo
2010/0159434 A1 6/2010 Lampotang et al.
2010/0175024 A1 7/2010 Schumacher et al.
2010/0204600 A1 8/2010 Crucilla
2010/0295685 A1 11/2010 Parvin et al.
2010/0295865 A1 11/2010 Wu et al.
2010/0316131 A1 12/2010 Shanableh et al.
2011/0087133 A1 4/2011 Ching et al.
2011/0164105 A1 7/2011 Lee et al.
2011/0188713 A1 8/2011 Chin et al.
2011/0207108 A1 8/2011 Dorman
2011/0213619 A1 9/2011 Henke
2011/0244919 A1 10/2011 Aller et al.
2011/0279228 A1 11/2011 Kumar
2012/0041784 A1 2/2012 Farooq et al.
2012/0053955 A1 3/2012 Martin et al.
2012/0125995 A1 5/2012 Kim
2012/0221960 A1 8/2012 Robinson et al.
2012/0231431 A1 9/2012 Angelides
2012/0323589 A1 12/2012 Udani
2013/0013333 A1 1/2013 Gopinathan et al.
2013/0017807 A1 1/2013 Rooyen et al.
2013/0044945 A1 2/2013 Nykyforov
2013/0068040 A1 3/2013 Loomis et al.
2013/0096937 A1 4/2013 Campbell et al.
2013/0124523 A1 5/2013 Rogers et al.
2013/0176326 A1 7/2013 Safaee-Rad et al.
2013/0209954 A1 8/2013 Prakash et al.
2013/0216982 A1 8/2013 Bennett et al.
2013/0253339 A1 9/2013 Reyes
2013/0290027 A1 10/2013 Tang et al.
2013/0328997 A1 12/2013 Desai
2013/0344470 A1 12/2013 Morgan et al.
2014/0019149 A1 1/2014 Yu et al.
2014/0043476 A1* 2/2014 Stark .................... G01K 11/12
382/165
2014/0072960 A1 3/2014 Lansing
2014/0073880 A1 3/2014 Boucher et al.
2014/0108842 A1 4/2014 Frank et al.
2014/0143437 A1 5/2014 Mathur et al.
2014/0160264 A1 6/2014 Taylor et al.
2014/0253590 A1 9/2014 Needham et al.
2014/0304335 A1 10/2014 Fung et al.
2014/0342333 A1 11/2014 Knoche et al.
2014/0372137 A1 12/2014 Tryon et al.
2015/0012292 A1 1/2015 Khan
2015/0104104 A1 4/2015 Retterath et al.
2015/0116126 A1 4/2015 Hyde et al.
2015/0118991 A1 4/2015 Chung et al.
2015/0187038 A1 7/2015 Johnson et al.
2015/0187048 A1 7/2015 Yang et al.
2015/0220689 A1 8/2015 Ward et al.
2015/0228086 A1 8/2015 Maurer et al.
2015/0233898 A1 8/2015 Chen et al.
2015/0294079 A1 10/2015 Bergougnan
2015/0297196 A1 10/2015 Ching et al.
2015/0305662 A1 10/2015 Kilmer et al.
2015/0310751 A1 10/2015 Tolia
2015/0324526 A1 11/2015 Cambray et al.
2015/0326901 A1 11/2015 Tiraspolsky et al.
2016/0034642 A1 2/2016 Ehrhart et al.
2016/0058673 A1 3/2016 Francis
2016/0077091 A1 3/2016 Tyrrell et al.
2016/0100906 A1 4/2016 Taylor et al.
2016/0125765 A1 5/2016 Meretei et al.
2016/0179336 A1 6/2016 Ambrus et al.
2016/0187263 A1 6/2016 Brown
2016/0189573 A1 6/2016 Bush
2016/0200462 A1 7/2016 Kriheli et al.
2016/0259911 A1 9/2016 Koester
2016/0285922 A1 9/2016 Ramalingam et al.
2016/0292378 A1 10/2016 Saric
2016/0371884 A1 12/2016 Benko et al.
2016/0378943 A1 12/2016 Vallée
2017/0011179 A1 1/2017 Arshad et al.
2017/0011200 A1 1/2017 Arshad et al.
2017/0039869 A1 2/2017 Gleim et al.
2017/0103440 A1 4/2017 Xing et al.
2017/0106239 A1 4/2017 Sutton et al.
2017/0115742 A1 4/2017 Xing et al.
2017/0116384 A1 4/2017 Ghani
2017/0127117 A1 5/2017 Ayers et al.
2017/0132393 A1 5/2017 Natarajan et al.
2017/0146801 A1 5/2017 Stempora
2017/0173262 A1 6/2017 Veltz
2017/0193833 A1 7/2017 Morgan et al.
2017/0213007 A1 7/2017 Moturu et al.
2017/0244879 A1 8/2017 Bezjian
2017/0277962 A1 9/2017 Kudo
2017/0302880 A1 10/2017 Cizerle
2017/0303886 A1 10/2017 Ferro, Jr.
2017/0323062 A1 11/2017 Djajadiningrat et al.
2017/0324930 A1 11/2017 Shaya
2017/0341152 A1 11/2017 Ida
2017/0347022 A1 11/2017 Pettersson et al.
2018/0007213 A1 1/2018 Mandanapu et al.
2018/0012176 A1 1/2018 Mchale et al.
2018/0039737 A1 2/2018 Dempers et al.
2018/0039752 A1 2/2018 Subbarao et al.
2018/0060510 A1 3/2018 Baldauf et al.
2018/0067106 A1 3/2018 Sim
2018/0092595 A1 4/2018 Chen et al.
2018/0140362 A1 5/2018 Cal et al.
2018/0173913 A1 6/2018 Pulitzer et al.
2018/0181713 A1 6/2018 Pillarisetty et al.
2018/0190373 A1 7/2018 Pulitzer et al.
2018/0196037 A1 7/2018 Polwart et al.
2018/0197624 A1 7/2018 Robaina et al.
2018/0217808 A1 8/2018 Baughman et al.
2018/0225982 A1 8/2018 Jaeh et al.

(56) References Cited

U.S. PATENT DOCUMENTS

2018/0226158 A1 8/2018 Fish et al.
2018/0232688 A1 8/2018 Pike et al.
2018/0253840 A1 9/2018 Tran
2018/0277258 A1 9/2018 Panwala
2018/0278808 A1 9/2018 Hsu et al.
2018/0341919 A1 11/2018 Luhman et al.
2018/0342050 A1 11/2018 Fitzgerald et al.
2018/0353073 A1 12/2018 Boucher et al.
2018/0356541 A1 12/2018 Steadman et al.
2018/0357915 A1 12/2018 Harlow et al.
2018/0365383 A1 12/2018 Bates
2018/0365641 A1 12/2018 Zhu
2018/0365786 A1 12/2018 Thompson
2018/0373844 A1 12/2018 Ferrandez-Escamez et al.
2018/0374580 A1 12/2018 Gupta et al.
2019/0000564 A1 1/2019 Navab et al.
2019/0005195 A1 1/2019 Peterson et al.
2019/0012176 A1 1/2019 Stephens et al.
2019/0020651 A1 1/2019 Soon-Shiong et al.
2019/0025919 A1 1/2019 Tadi et al.
2019/0027233 A1 1/2019 Bender et al.
2019/0050988 A1 2/2019 Dimov et al.
2019/0064520 A1 2/2019 Christensen
2019/0073110 A1 3/2019 Bradley et al.
2019/0087951 A1 3/2019 Hanina et al.
2019/0088026 A1 3/2019 Isaacson et al.
2019/0089701 A1 3/2019 Mercury et al.
2019/0115097 A1 4/2019 Macoviak et al.
2019/0116337 A1 4/2019 Naidoo et al.
2019/0125249 A1 5/2019 Rattner et al.
2019/0139318 A1 5/2019 Tierney et al.
2019/0148014 A1 5/2019 Pulitzer et al.
2019/0156689 A1 5/2019 Jaeh et al.
2019/0179584 A1 6/2019 Masters
2019/0189254 A1 6/2019 Roennow
2019/0197443 A1 6/2019 Anderson et al.
2019/0205891 A1 7/2019 Roebuck
2019/0206134 A1 7/2019 Devam et al.
2019/0216452 A1 7/2019 Nawana et al.
2019/0259483 A1 8/2019 Nicholas
2019/0261914 A1 8/2019 Davis et al.
2019/0261957 A1 8/2019 Zaslavsky et al.
2019/0266663 A1 8/2019 Keeler et al.
2019/0303551 A1 10/2019 Tussy
2019/0341152 A1 11/2019 Mellem et al.
2019/0346429 A1 11/2019 Harris et al.
2019/0362554 A1 11/2019 Chen et al.
2019/0362841 A1 11/2019 Aysin et al.
2019/0378080 A1 12/2019 Srinivasan et al.
2019/0378624 A1 12/2019 Pulitzer et al.
2019/0380790 A1 12/2019 Fuchs et al.
2019/0391638 A1 12/2019 Khaderi et al.
2020/0000401 A1 1/2020 Dullen
2020/0005947 A1 1/2020 Blanchard et al.
2020/0020171 A1 1/2020 Hendricks et al.
2020/0020454 A1 1/2020 Mcgarvey et al.
2020/0073143 A1 3/2020 Macnamara et al.
2020/0074741 A1 3/2020 Schulze et al.
2020/0101367 A1 4/2020 Tran et al.
2020/0152339 A1 5/2020 Pulitzer et al.
2020/0174756 A1 6/2020 Cerar et al.
2020/0175769 A1 6/2020 Mandala
2020/0203024 A1 6/2020 Hunter et al.
2020/0205913 A1 7/2020 Carnes et al.
2020/0207501 A1 7/2020 Urquhart et al.
2020/0209214 A1 7/2020 Zohar et al.
2020/0211291 A1 7/2020 Miller et al.
2020/0211682 A1 7/2020 Zohar et al.
2020/0211693 A1 7/2020 Adiri et al.
2020/0218781 A1 7/2020 Takano et al.
2020/0225830 A1 7/2020 Tang et al.
2020/0226758 A1 7/2020 Carnes et al.
2020/0250389 A1 8/2020 Pulitzer et al.
2020/0261799 A1 8/2020 Cahill et al.
2020/0279659 A1 9/2020 De et al.
2020/0303044 A1 9/2020 Stephen
2020/0312038 A1 10/2020 Samec et al.
2020/0312437 A1 10/2020 Wendland et al.
2020/0320365 A1 10/2020 Arat et al.
2020/0320608 A1 10/2020 Handy et al.
2020/0334810 A1 10/2020 Accomazzi et al.
2020/0337631 A1 10/2020 Sahin
2020/0342679 A1 10/2020 Soon-Shiong
2020/0342963 A1 10/2020 Mohammad
2020/0350072 A1 11/2020 Mcewing et al.
2020/0359891 A1 11/2020 Fried et al.
2020/0367018 A1 11/2020 Reinhardt et al.
2020/0405257 A1 12/2020 Samec et al.
2020/0409159 A1 12/2020 Samec et al.
2021/0015583 A1 1/2021 Avisar et al.
2021/0022646 A1 1/2021 Li et al.
2021/0022810 A1 1/2021 Mahfouz
2021/0058485 A1 2/2021 Devam et al.
2021/0082554 A1 3/2021 Kalia et al.
2021/0086989 A1 3/2021 Luxford
2021/0089814 A1 3/2021 Lopes et al.
2021/0118029 A1 4/2021 Koritala
2021/0118323 A1 4/2021 Quy
2021/0183507 A1 6/2021 Shaya
2021/0202104 A1 7/2021 Bostic et al.
2021/0223239 A1 7/2021 De et al.
2021/0225468 A1 7/2021 Saliman et al.
2021/0244148 A1 8/2021 Harris
2021/0293805 A1 9/2021 Rothberg et al.
2021/0295954 A1 9/2021 Rothberg et al.
2021/0325299 A1 10/2021 Hardie et al.
2021/0326474 A1 10/2021 Sparks et al.
2021/0327304 A1 10/2021 Buras et al.
2021/0334967 A1 10/2021 Adiri et al.
2021/0350883 A1 11/2021 Li et al.
2021/0358064 A1 11/2021 Kudo
2021/0358068 A1 11/2021 Boszczyk et al.
2021/0358602 A1 11/2021 Pannucci
2021/0370288 A1 12/2021 Daly et al.
2021/0401338 A1 12/2021 Flickinger
2021/0405689 A1 12/2021 Kariguddaiah
2022/0003761 A1 1/2022 Pulitzer et al.
2022/0005610 A1 1/2022 Ehrlich et al.
2022/0020236 A1 1/2022 Luthra et al.
2022/0020481 A1 1/2022 Luthra et al.
2022/0027587 A1 1/2022 Cooper
2022/0028562 A1 1/2022 Klasson
2022/0054008 A1 2/2022 Venkatraman et al.
2022/0074000 A1 3/2022 Wong et al.
2022/0084659 A1 3/2022 Rowe et al.
2022/0084665 A1 3/2022 Blackburn et al.
2022/0101608 A1 3/2022 Hu et al.
2022/0157475 A1 5/2022 Pulitzer et al.
2022/0181019 A1 6/2022 Ukrainksy et al.
2022/0223279 A1 7/2022 Ferro, Jr. et al.
2022/0223280 A1 7/2022 Ferro, Jr. et al.
2022/0223281 A1 7/2022 Ferro, Jr. et al.
2022/0223282 A1 7/2022 Ferro et al.
2022/0223300 A1 7/2022 Ferro et al.
2022/0230747 A1 7/2022 Ferro et al.
2022/0236208 A1 7/2022 Carpenter
2022/0254458 A1 8/2022 Mooney et al.
2022/0257149 A1 8/2022 Ralston et al.
2022/0270720 A1 8/2022 Aysin et al.
2022/0270752 A1 8/2022 Ferro et al.
2022/0285007 A1 9/2022 Dehaan et al.
2022/0310249 A1 9/2022 Ferro, Jr. et al.
2022/0310250 A1 9/2022 Ferro, Jr. et al.
2022/0310252 A1 9/2022 Ferro et al.
2022/0310253 A1 9/2022 Ferro et al.
2022/0319676 A1 10/2022 Bosanac et al.
2022/0331047 A1 10/2022 Shelton et al.
2022/0375594 A1 11/2022 Ferro et al.
2022/0375595 A1 11/2022 Ferro et al.
2022/0375596 A1 11/2022 Ferro et al.
2022/0392588 A1 12/2022 Crowley et al.
2022/0392589 A1 12/2022 Lauritzen et al.
2022/0398843 A1 12/2022 Ju et al.
2022/0406458 A1 12/2022 Ferro, Jr. et al.

(56) References Cited

U.S. PATENT DOCUMENTS

| | | | |
|---|---|---|---|
| 2023/0005614 | A1 | 1/2023 | Ferro et al. |
| 2023/0049589 | A1 | 2/2023 | Ferro et al. |
| 2023/0051833 | A1 | 2/2023 | Achin et al. |
| 2023/0057531 | A1 | 2/2023 | Nienstedt et al. |
| 2023/0063441 | A1 | 3/2023 | Kramer et al. |
| 2023/0071025 | A1 | 3/2023 | Kramer et al. |
| 2023/0072470 | A1 | 3/2023 | Miller et al. |
| 2023/0072820 | A1 | 3/2023 | Houshmand et al. |
| 2023/0086239 | A1 | 3/2023 | Morris et al. |
| 2023/0107915 | A1 | 4/2023 | Lyon et al. |
| 2023/0121265 | A1 | 4/2023 | Nienstedt et al. |
| 2023/0130987 | A1 | 4/2023 | Kramer et al. |
| 2023/0166252 | A1 | 6/2023 | Nienstedt et al. |
| 2023/0207078 | A1 | 6/2023 | Nienstedt et al. |
| 2023/0207115 | A1 | 6/2023 | Ferro, Jr. et al. |
| 2023/0207116 | A1 | 6/2023 | Ferro, Jr. et al. |
| 2023/0207117 | A1 | 6/2023 | Ferro, Jr. et al. |
| 2023/0207118 | A1 | 6/2023 | Ferro, Jr. et al. |
| 2023/0207119 | A1 | 6/2023 | Ferro, Jr. et al. |
| 2023/0215561 | A1 | 7/2023 | Ferro, Jr. et al. |
| 2023/0260627 | A1 | 8/2023 | Bychkov et al. |
| 2023/0263671 | A1 | 8/2023 | Schumm et al. |
| 2023/0268057 | A1 | 8/2023 | Zohar et al. |
| 2023/0268070 | A1 | 8/2023 | Nienstedt et al. |
| 2023/0316479 | A1 | 10/2023 | Mulligan |
| 2023/0326586 | A1 | 10/2023 | Nienstedt et al. |
| 2023/0343453 | A1 | 10/2023 | Ferro, Jr. et al. |
| 2023/0352166 | A1 | 11/2023 | Ferro, Jr. et al. |
| 2023/0352167 | A1 | 11/2023 | Ferro, Jr. et al. |
| 2023/0359421 | A1 | 11/2023 | Nienstedt et al. |
| 2023/0368436 | A1 | 11/2023 | Nienstedt et al. |
| 2023/0386677 | A1 | 11/2023 | Ferro et al. |
| 2023/0419728 | A1 | 12/2023 | Miller et al. |
| 2024/0013912 | A1 | 1/2024 | Kramer |
| 2024/0020939 | A1 | 1/2024 | Sands |
| 2024/0028176 | A1 | 1/2024 | Nienstedt et al. |
| 2024/0029888 | A1 | 1/2024 | Kramer et al. |
| 2024/0038385 | A1 | 2/2024 | Nienstedt |
| 2024/0044756 | A1 | 2/2024 | Kramer |
| 2024/0105331 | A1 | 3/2024 | Ferro et al. |
| 2024/0153626 | A1 | 5/2024 | Ferro et al. |
| 2024/0153627 | A1 | 5/2024 | Ferro, Jr. et al. |
| 2024/0161888 | A1 | 5/2024 | Crowley et al. |
| 2024/0238778 | A1 | 7/2024 | Menezes et al. |
| 2024/0265661 | A1 | 8/2024 | Mclachlan et al. |
| 2024/0282443 | A1 | 8/2024 | Ferro, Jr. et al. |
| 2024/0404708 | A1 | 12/2024 | Ben-David |
| 2025/0349441 | A1 | 11/2025 | Ferro et al. |
| 2026/0004908 | A1 | 1/2026 | Souslova et al. |

FOREIGN PATENT DOCUMENTS

| | | | |
|---|---|---|---|
| CN | 105266897 | A | 1/2016 |
| CN | 107894502 | A | 4/2018 |
| CN | 110853021 | A | 2/2020 |
| CN | 213097775 | U | 5/2021 |
| CN | 112989917 | A | 6/2021 |
| EP | 3108244 | A1 | 12/2016 |
| EP | 3872813 | A1 | 9/2021 |
| JP | 2013-233231 | A | 11/2013 |
| KR | 10-2008-0012745 | A | 2/2008 |
| KR | 10-1014852 | B1 | 2/2011 |
| KR | 10-2012-0076652 | A | 7/2012 |
| KR | 10-2012-0076665 | A | 7/2012 |
| KR | 10-2018-0068703 | A | 6/2018 |
| KR | 10-1962066 | B1 | 7/2019 |
| KR | 10-2019-0108119 | A | 9/2019 |
| KR | 10-2020-0125658 | A | 11/2020 |
| KR | 10-2249463 | B1 | 5/2021 |
| WO | 02/17171 | A1 | 2/2002 |
| WO | 2016/016816 | A1 | 2/2016 |
| WO | 2018/218162 | A1 | 11/2018 |
| WO | 2019/213221 | A1 | 11/2019 |
| WO | 2019/222081 | A1 | 11/2019 |
| WO | 2020/023289 | A1 | 1/2020 |
| WO | 2020/121270 | A1 | 6/2020 |
| WO | 2021/026549 | A1 | 2/2021 |
| WO | 2021/044064 | A1 | 3/2021 |
| WO | 2021/064114 | A1 | 4/2021 |
| WO | 2021/149050 | A1 | 7/2021 |
| WO | 2021/170376 | A1 | 9/2021 |
| WO | 2021/171226 | A2 | 9/2021 |
| WO | 2021/180442 | A1 | 9/2021 |
| WO | 2021/211804 | A1 | 10/2021 |
| WO | 2022/060415 | A1 | 3/2022 |
| WO | 2022/074178 | A1 | 4/2022 |
| WO | 2022/204054 | A1 | 9/2022 |

OTHER PUBLICATIONS

File history of U.S. Appl. No. 63/477,099, filed Dec. 23, 2022.
File history of U.S. Appl. No. 63/477,134, filed Dec. 23, 2022.
File history of U.S. Appl. No. 63/486,887, filed Feb. 24, 2023.
File history of U.S. Appl. No. 63/487,800, filed Mar. 1, 2023.
File history of U.S. Appl. No. 63/493,205, filed Mar. 30, 2023.
Abbott, Dec. 2020, BinaxnowTM covid-19 Ag card home test and NavicaTM app, https://web.archive.org/web/20201 224151 604/ https://wwww.globalpointofcare/abbott, 3 pp.
Bamba, Y., et al., "Automated recognition of objects and types of forceps in surgical images using deep learning.", Scientific Reports, vol. 11, No. 1, Nov. 19, 2021, pp. 1-8.
Baruah, Basant, "Augmented reality and QR codes—What you need to know", accessed via wayback machine for Apr. 14, 2021, beaconstac blog.
Cooper, D. "Assessment of COVID-19 Diagnostic Self-testing Using Virtual Point-of-care, fu: ClinicalTrials.gov archive", U.S. National Library of Medicine, Study NCT04348864 [online], Feb. 16, 2021.
Doosti et al., 2020, HOPE-Net: a graph-based model for hand-object pose estimation, IEEE/CVF Conference on Computer Vision and Pattern Recognition (CVPR), pp. 6608-6617.
File history of U.S. Appl. No. 63/365,441, filed May 27, 2022.
File history of U.S. Appl. No. 63/365,461, filed May 27, 2022.
File history of U.S. Appl. No. 63/485,513, filed Feb. 16, 2023.
File history of U.S. Appl. No. 63/491,701, filed Mar. 22, 2023.
Lixia Zheng, "Using Augmented Reality with Interactive Narrative to Help Paediatric Patients Take Prescription Medication", 2020, University College London (Year: 2020).
Majumder et al. 2019, "Smartphone Sensors for Health Monitoring and Diagnosis," Sensors (Basel). May 9, 2019; 19 (9):2164.
N.A., "Clarifi COVID-19 Test Kit—Instructions for Use", Sep. 22, 2020, Food and Drug Administration, all pages. URL: https://www.fda.gov/media/142379/download. (Year: 2020).
Nejati et al. 2016, "Smartphone and Mobile Image Processing for Assisted Living: Health-monitoring apps powered by advanced mobile imaging algorithms," in IEEE Signal Processing Magazine, vol. 33, No. 4, pp. 30-48, Jul. 2016.
Sathyanarayana, Supriya, et al. "Vision-based patient monitoring: a comprehensive review of algorithms and technologies." Journal of Ambient Intelligence and Humanized Computing 9 (2018): 225-251. (Year: 2018).
Shimizu, T., et al., "Hand motion-aware surgical tool localization and classification from an egocentric camera.", Journal of imaging, vol. 7, No. 2, Jan. 25, 2021, pp. 1-13.
Taha et al., Jul. 2014, Human action recognition based on MSVM and depth images, International Journal of Computer Science Issues, 11(4):42-51.
Uber Blog, "Uber expands options for prescription delivery service with ScriptDrop", Mar. 24, 2021. (Year: 2021).
Using AI to detect If I Touch My Face! (Speezlab) Feb. 24, 2014, Retrieved from the Internet <URL:hllps://www.youtube.com/watch?v=OZjlvkatLCs>.
Yu-Hsiang, H. et al., "Performance evaluation and acceptability of point-of-care Trichomonas vaginalis testing in adult female emergency depmtment patients", fu: futernational Journal of STD & AIDS, vol. 31, No. 14, 2020, pp. 1364-1372.

* cited by examiner

Testing Status Board

| Name | Ordered | Shipped | Delivered | Completed | Result | Actions |
|---|---|---|---|---|---|---|
| Smith, John | ✓ | ✓ | ✓ | | | View Details ▼ |
| Brown, David | ✓ | ✓ | ✓ | ✓ | Negative | View Details ▼ |
| Doe, Susan | ✓ | ✓ | | | | View Details ▼ |
| Adams, John | ✓ | ✓ | ✓ | ✓ | Negative | View Details ▼ |
| Smith, Jane | ✓ | | | | | View Details ▼ |
| Jones, Roberta | ✓ | ✓ | ✓ | ✓ | Positive | View Details ▼ |

FIG. 6

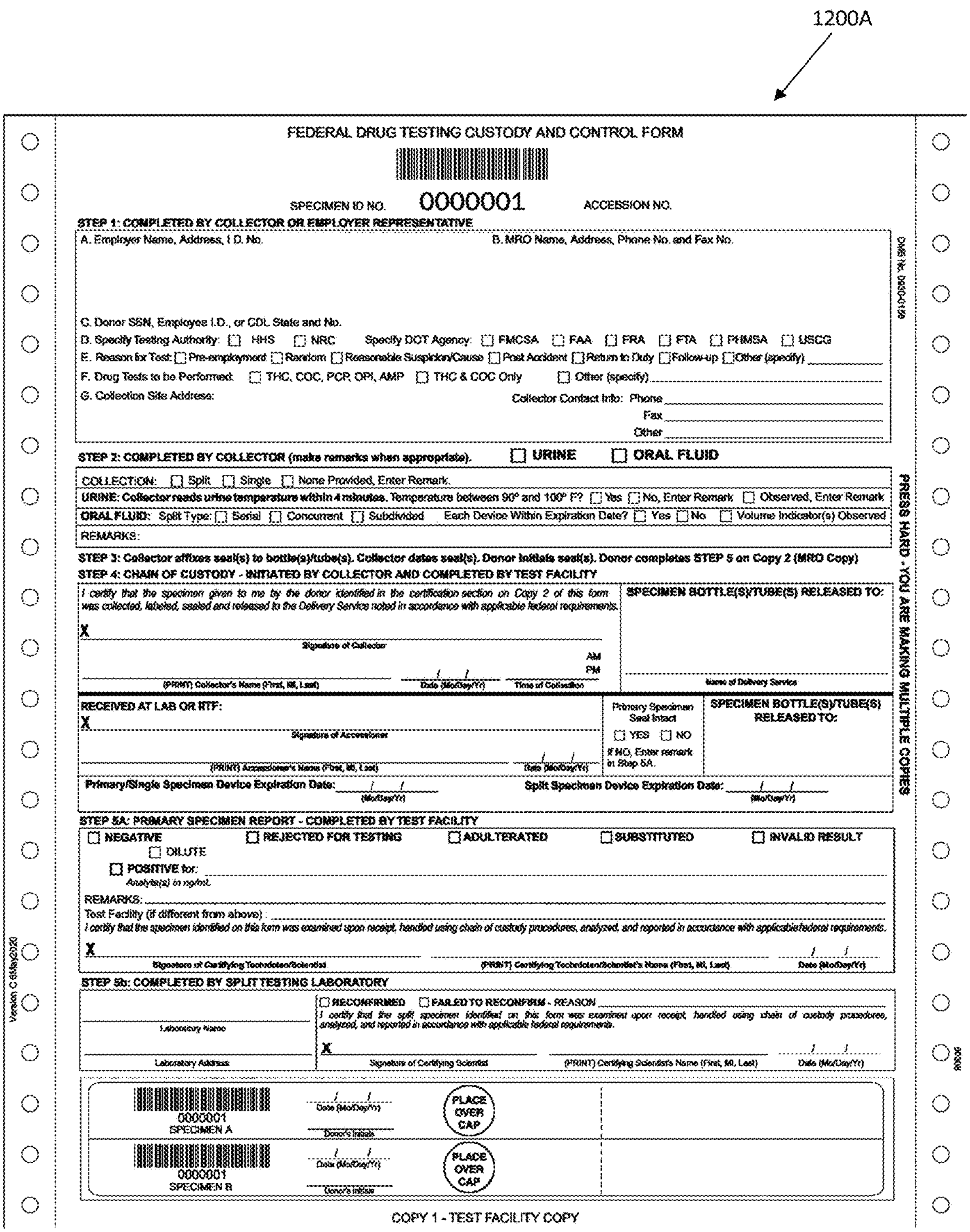

FEDERAL DRUG TESTING CUSTODY AND CONTROL FORM

SPECIMEN ID NO. 0000001 ACCESSION NO.

STEP 1: COMPLETED BY COLLECTOR OR EMPLOYER REPRESENTATIVE

A. Employer Name, Address, I.D. No.

B. MRO Name, Address, Phone No. and Fax No.

C. Donor SSN, Employee I.D., or CDL State and No.

D. Specify Testing Authority: ☐ HHS ☐ NRC Specify DOT Agency: ☐ FMCSA ☐ FAA ☐ FRA ☐ FTA ☐ PHMSA ☐ USCG E. Reason for Test: ☐ Pre-employment ☐ Random ☐ Reasonable Suspicion/Cause ☐ Post Accident ☐ Return to Duty ☐ Follow-up ☐ Other (specify)

F. Drug Tests to be Performed: ☐ THC, COC, PCP, OPI, AMP ☐ THC & COC Only ☐ Other (specify)

G. Collection Site Address:

Collector Contact Info: Phone

Fax

Other

STEP 2: COMPLETED BY COLLECTOR (make remarks when appropriate). ☐ URINE ☐ ORAL FLUID COLLECTION: ☐ Split ☐ Single ☐ None Provided, Enter Remark URINE: Collector reads urine temperature within 4 minutes. Temperature between 90° and 100° F? ☐ Yes ☐ No, Enter Remark ☐ Observed, Enter Remark ORAL FLUID: Split Type: ☐ Serial ☐ Concurrent ☐ Subdivided Each Device Within Expiration Date? ☐ Yes ☐ No ☐ Volume Indicator(s) Observed

REMARKS:

STEP 3: Collector affixes seal(s) to bottle(s)/tube(s). Collector dates seal(s). Donor initials seal(s). Donor completes STEP 5 on Copy 2 (MRO Copy)

STEP 4: CHAIN OF CUSTODY - INITIATED BY COLLECTOR AND COMPLETED BY TEST FACILITY

*I certify that the specimen given to me by the donor identified in the certification section on Copy 2 of this form was collected, labeled, sealed and released to the Delivery Service noted in accordance with applicable federal requirements.*

X

Signature of Collector

AM

PM (PRINT) Collector's Name (First, MI, Last) Date (Mo/Day/Yr) Time of Collection

SPECIMEN BOTTLE(S)/TUBE(S) RELEASED TO:

Name of Delivery Service

RECEIVED AT LAB OR IITF:

X

Signature of Accessioner (PRINT) Accessioner's Name (First, MI, Last) Date (Mo/Day/Yr)

Primary Specimen Seal Intact ☐ YES ☐ NO

If NO, Enter remark in Step 5A.

SPECIMEN BOTTLE(S)/TUBE(S) RELEASED TO:

Primary/Single Specimen Device Expiration Date: (Mo/Day/Yr)

Split Specimen Device Expiration Date: (Mo/Day/Yr)

STEP 5A: PRIMARY SPECIMEN REPORT - COMPLETED BY TEST FACILITY

☐ NEGATIVE ☐ DILUTE ☐ REJECTED FOR TESTING ☐ ADULTERATED ☐ SUBSTITUTED ☐ INVALID RESULT

☐ POSITIVE for:

Analyte(s) in ng/mL

REMARKS:

Test Facility (if different from above):

*I certify that the specimen identified on this form was examined upon receipt, handled using chain of custody procedures, analyzed, and reported in accordance with applicable federal requirements.*

X

Signature of Certifying Technician/Scientist (PRINT) Certifying Technician/Scientist's Name (First, MI, Last) Date (Mo/Day/Yr)

STEP 5b: COMPLETED BY SPLIT TESTING LABORATORY

Laboratory Name

Laboratory Address

☐ RECONFIRMED ☐ FAILED TO RECONFIRM - REASON

*I certify that the split specimen identified on this form was examined upon receipt, handled using chain of custody procedures, analyzed, and reported in accordance with applicable federal requirements.*

X

Signature of Certifying Scientist (PRINT) Certifying Scientist's Name (First, MI, Last) Date (Mo/Day/Yr)

0000001 SPECIMEN A Date (Mo/Day/Yr) Donor's Initials PLACE OVER CAP

0000001 SPECIMEN B Date (Mo/Day/Yr) Donor's Initials PLACE OVER CAP

PRESS HARD - YOU ARE MAKING MULTIPLE COPIES

COPY 1 - TEST FACILITY COPY

FIG. 12A

SYSTEMS, METHODS, AND DEVICES FOR AN INTEGRATED TELEHEALTH PLATFORM

CROSS-REFERENCE TO RELATED APPLICATIONS

The present application claims the benefit of U.S. Provisional Patent Application No. 63/477,134, filed Dec. 23, 2022, U.S. Provisional Patent Application No. 63/477,072, filed Dec. 23, 2022, U.S. Provisional Patent Application No. 63/477,099, filed Dec. 23, 2022, U.S. Provisional Application No. 63/486,887, filed Feb. 24, 2023, U.S. Provisional Patent Application No. 63/493,205, filed Mar. 30, 2023, and U.S. Provisional Patent Application No. 63/487,800, filed Mar. 1, 2023, the disclosures of which are incorporated herein by reference in their entireties.

TECHNICAL FIELD

The present disclosure relates to systems, methods, and devices for an integrated telehealth platform, and particularly for providing health diagnostics and drug screening remotely.

BACKGROUND

The use of telehealth to deliver health care services has grown consistently over the last several decades and has experienced very rapid growth in the last several years. Telehealth can include the distribution of health-related services and information via electronic information and telecommunication technologies. Telehealth can allow for long-distance user and health provider contact, care, advice, reminders, education, intervention, monitoring, and admissions. Often, telehealth can involve the use of a user or patient's personal electronic device such as a smartphone, tablet, laptop, desktop computer, or other type of personal device. For example, the user or patient can interact with a remotely located medical care provider using live video and/or audio through the personal device.

Remote or at-home health care testing and diagnostics can solve or alleviate some problems associated with in-person testing. For example, health insurance may not be required, travel to a testing site is avoided, and tests can be completed at a user's convenience. However, at-home testing introduces various additional logistical and technical issues, such as guaranteeing timely test delivery to a user's home, providing test delivery from a user to an appropriate lab, ensuring test verification and integrity, providing test result reporting to appropriate authorities and medical providers, guiding users through unfamiliar processes such as sample collection and/or processing, connecting users with medical providers, who are sometimes needed to provide guidance and/or oversight of the testing procedures remotely, and delivering treatment to users.

SUMMARY

For purposes of this summary, certain aspects, advantages, and novel features are described herein. It is to be understood that not necessarily all such advantages may be achieved in accordance with any particular embodiment. Thus, for example, those skilled in the art will recognize the disclosures herein may be embodied or carried out in a manner that achieves one or more advantages taught herein without necessarily achieving other advantages as may be taught or suggested herein.

All of the embodiments described herein are intended to be within the scope of the present disclosure. These and other embodiments will be readily apparent to those skilled in the art from the following detailed description, having reference to the attached figures. The invention is not intended to be limited to any particular disclosed embodiment or embodiments.

In some aspects, the techniques described herein relate to a computer-implemented method, the method including: receiving, from a user device, an image of at least a portion of a thermometer used by a user, wherein the portion of the thermometer includes one or more temperature indicator features; analyzing the received image to determine an image transformation, wherein analyzing the received image includes: identifying one or more alignment features in the received image based on at least one of a quality or a number of pixels of the alignment features; generating a matched image by aligning the received image with a template such that the one or more alignment features of the received image positionally align with corresponding one or more alignment features of the template; determining that the one or more alignment features of the received image are within a maximum threshold distance from the corresponding one or more alignment features of the template in the matched image; and generating a warped image by warping the matched image such that the one or more features of the received image positionally align with the corresponding one or more features of the template; determining that the warped image qualifies for interpretation, wherein determining that the warped image qualifies for interpretation includes determining that an image characteristic of the warped image is above a predetermined threshold corresponding to the image characteristic; generating an assist image based on the warped image based on the determined image transformation; and determining a temperature of the user based on the generated assist image.

In some aspects, the techniques described herein relate to a computer-implemented method, wherein analyzing the received image further includes: determining image information from the received image; and determining that the image information is above a second predetermined threshold.

In some aspects, the techniques described herein relate to a computer-implemented method, wherein the image information includes a resolution of the received image.

In some aspects, the techniques described herein relate to a computer-implemented method, wherein generating the assist image includes: generating a cropped image by cropping the warped image such that the one or more temperature indicator features of the thermometer are in the cropped image; determining at least one of a white level or a black level of the cropped image; modifying a dynamic range of the cropped image based on at least one of the determined white level or the determined black level; and generating a balanced image by modifying a white balance of the cropped image based on the determined white level and/or the determined black level.

In some aspects, the techniques described herein relate to a computer-implemented method, wherein generating the assist image further includes: determining that a blur level of the balanced image is below a predetermined threshold; generating a filtered image by applying a filter to the balanced image to preserve edges of one or more features in the balanced image; generating an enhanced image by modifying one or more color attributes of the filtered image; extracting a color of each of the one or more temperature indicator features in the enhanced image; generating a first intermediary assist image from the enhanced image, wherein each of the one or more temperature indicator features are at a corresponding predetermined location in the first intermediary assist image; generating a second intermediary assist image from a virtual thermometer template including one or more virtual temperature indicator features, wherein each of the one or more virtual temperature indicator features are filled with the corresponding extracted color in the second intermediary assist image; and generating the assist image by combining the first intermediary assist image and the second intermediary assist image.

In some aspects, the techniques described herein relate to a computer-implemented method, wherein the filter includes a median filter.

In some aspects, the techniques described herein relate to a computer-implemented method, wherein determining the temperature of the user includes: determining an array of dominant colors based on the generated assist image, wherein the dominant colors of the array correspond to the one or more temperature indicator features; generating an input image, wherein the input image includes a grayscale version of the array of dominant colors; generating a filter waveform of mean or median contrasts of the one or more temperature indicator features, wherein each of data points of the filter waveform corresponds to a different subset of the one or more temperature indicator features; generating a filtered waveform by applying a filter to the filter waveform; and determining the temperature of the user by analyzing the filtered waveform.

In some aspects, the techniques described herein relate to a computer-implemented method, wherein generating the filtered waveform includes: determining a polynomial fit of the filter waveform; and adding the determined polynomial fit or a negative of the determined polynomial fit to the data points of the filter waveform. 9.

In some aspects, the techniques described herein relate to a computer-implemented method, wherein determining the temperature of the user includes: determining a plurality of slopes corresponding to different portions of the filtered waveform between the data points, wherein the temperature of the user corresponds to a temperature value associated with at least one of the data points on the portion with a largest slope.

In some aspects, the techniques described herein relate to a computer-implemented method, further including: performing a confidence check of the determined temperature of the user, wherein performing the confidence check includes confirming that no other portion of the filtered waveform has a slope within a predetermined threshold of the largest slope.

In some aspects, the techniques described herein relate to a non-transient computer readable medium containing program instructions for causing a computer to perform a method including: receiving, from a user device, an image of at least a portion of a thermometer used by a user, wherein the portion of the thermometer includes one or more temperature indicator features; analyzing the received image to determine an image transformation, wherein analyzing the received image includes: identifying one or more alignment features in the received image based on at least one of a quality or a number of pixels of the alignment features; generating a matched image by aligning the received image with a template such that the one or more alignment features of the received image positionally align with corresponding one or more alignment features of the template; determining that the one or more alignment features of the received image are within a maximum threshold distance from the corresponding one or more alignment features of the template in the matched image; and generating a warped image by warping the matched image such that the one or more features of the received image positionally align with the corresponding one or more features of the template; determining that the warped image qualifies for interpretation, wherein determining that the warped image qualifies for interpretation includes determining that an image characteristic of the warped image is above a predetermined threshold corresponding to the image characteristic; generating an assist image based on the warped image based on the determined image transformation; and determining a temperature of the user based on the generated assist image.

In some aspects, the techniques described herein relate to a non-transient computer readable medium, wherein analyzing the received image further includes: determining image information from the received image; and determining that the image information is above a predetermined threshold.

In some aspects, the techniques described herein relate to a non-transient, computer readable medium, wherein the image information includes a resolution of the received image.

In some aspects, the techniques described herein relate to a non-transient computer readable medium, wherein generating the assist image includes: generating a cropped image by cropping the warped image such that the one or more temperature indicator features of the thermometer are in the cropped image; determining at least one of a white level or a black level of the cropped image; modifying a dynamic range of the cropped image based on at least one of the determined white level or the determined black level; and generating a balanced image by modifying a white balance of the cropped image based on the determined white level and/or the determined black level.

In some aspects, the techniques described herein relate to a non-transient computer readable medium, wherein generating the assist image further includes: determining that a blur level of the balanced image is below a predetermined threshold; generating a filtered image by applying a filter to the balanced image to preserve edges of one or more features in the balanced image; generating an enhanced image by modifying one or more color attributes of the filtered image; extracting a color of each of the one or more temperature indicator features in the enhanced image; generating a first intermediary assist image from the enhanced image, wherein each of the one or more temperature indicator features are at a corresponding predetermined location in the first intermediary assist image; generating a second intermediary assist image from a virtual thermometer template including one or more virtual temperature indicator features, wherein each of the one or more virtual temperature indicator features are filled with the corresponding extracted color in the second intermediary assist image; and generating the assist image by combining the first intermediary assist image and the second intermediary assist image.

In some aspects, the techniques described herein relate to a non-transient computer readable medium, wherein the filter includes a median filter.

In some aspects, the techniques described herein relate to a non-transient computer readable medium, wherein determining the temperature of the user includes: determining an array of dominant colors based on the generated assist image, wherein the dominant colors of the array correspond to the one or more temperature indicator features; generating an input image, wherein the input image includes a grayscale version of the array of dominant colors; generating a filter waveform of mean or median contrasts of the one or more temperature indicator features, wherein each of data points of the filter waveform corresponds to a different subset of the one or more temperature indicator features; generating a filtered waveform by applying a filter to the filter waveform; and determining the temperature of the user by analyzing the filtered waveform.

In some aspects, the techniques described herein relate to a non-transient computer readable medium, wherein generating the filtered waveform includes: determining a polynomial fit of the filter waveform; and adding the determined polynomial fit or a negative of the determined polynomial fit to the data points of the filter waveform.

In some aspects, the techniques described herein relate to a non-transient computer readable medium, wherein determining the temperature of the user includes: determining a plurality of slopes corresponding to different portions of the filtered waveform between the data points, wherein the temperature of the user corresponds to a temperature value associated with at least one of the data points on the portion with a largest slope.

In some aspects, the techniques described herein relate to a non-transient computer readable medium, wherein the method further includes: performing a confidence check of the determined temperature of the user, wherein performing the confidence check includes confirming that no other portion of the filtered waveform has a slope within a predetermined threshold of the largest slope.

BRIEF DESCRIPTION OF THE DRAWINGS

Features, aspects, and advantages of the presently disclosed technology may be better understood with regard to the following drawings.

FIG. 6 illustrates an example testing status board interface according to some embodiments.

FIGS. 12A and 12B show example chain of custody forms.

FIGS. 19-21 and 23B are flowcharts illustrating a method or portions thereof for performing a telehealth test in accordance with some embodiments.

Figure 1:
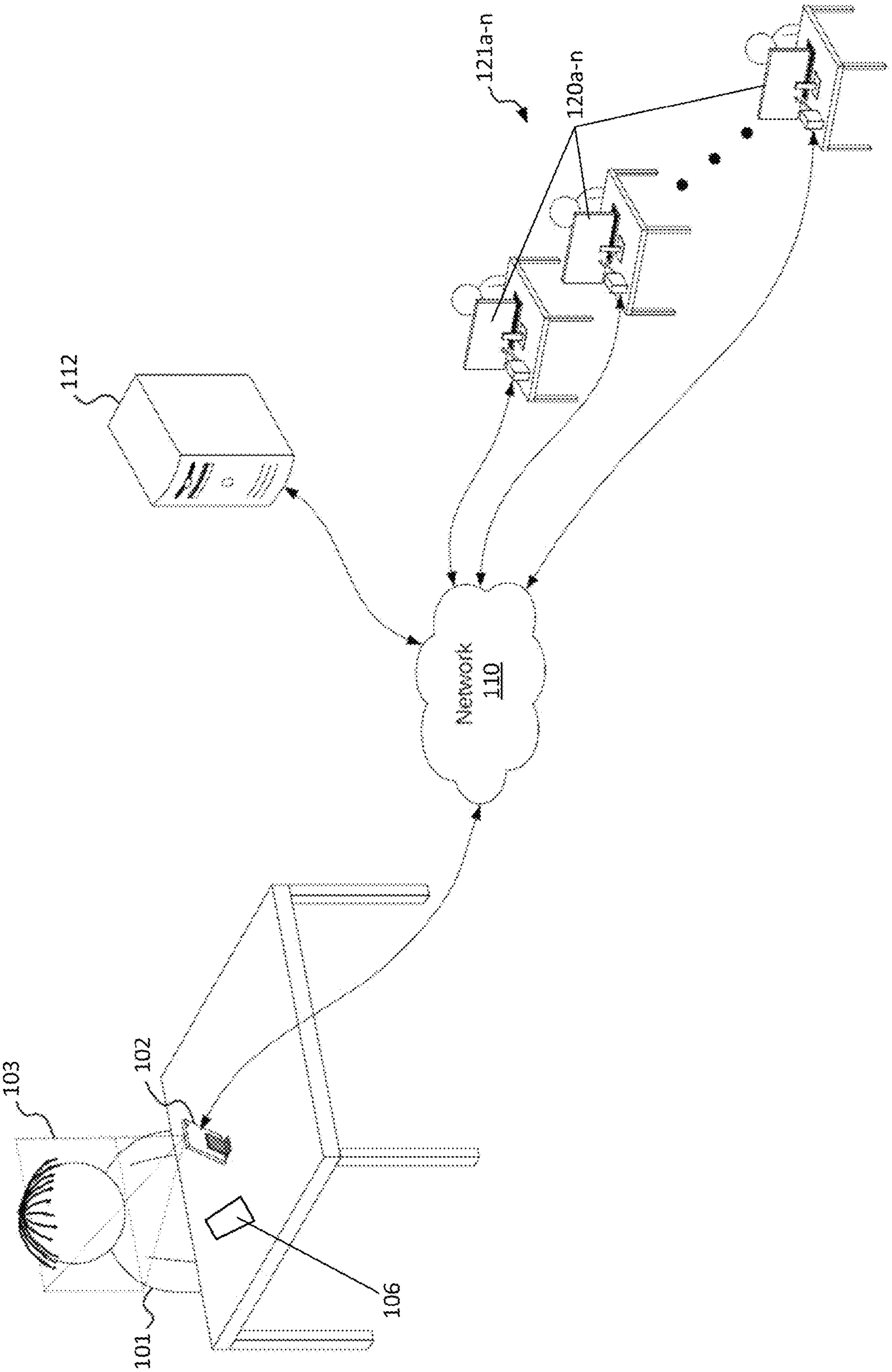
FIG. 1 provides a schematic diagram illustrating a patient interaction or telehealth system according to some embodiments.

A person skilled in the relevant art will understand that the features shown in the drawings are for purposes of illustration, and variations, including different and/or additional features and arrangements thereof, are possible. Features may not be to scale.

DETAILED DESCRIPTION

Overview

Embodiments of the present disclosure relate to systems, methods, and devices for an integrated telehealth platform, and particularly to telehealth platforms providing health diagnostics, drug screening, and/or the like. A user may want to or be required to (e.g., by an employer or government agency) take part in telehealth services, such as receiving diagnoses or undergoing drug screening. The telehealth platform disclosed herein can provide order fulfillment, coordinate delivery of various kits, connect users to providers, guide users in using the kits, analyze kit results, follow up with the user depending on the kit results, and more. The test kits can be for diagnostics, temperature measurement, drug screening, etc.

For example, a user experiencing symptoms such as coughing may want to test themselves for various conditions without leaving their home for purposes of comfort, convenience, avoiding exposure to others, and so forth. The telehealth platform can receive an order for a test kit or other telehealth platform product or service from a user via a user device. The telehealth platform may fulfill the order and coordinate delivery of a diagnostic test kit or other telehealth materials to the user. The diagnostic test kit can include a machine-readable code (e.g., a QR code, barcode, etc.) that allows a user device to easily connect to the telehealth platform over a network, and one or more testing equipment components such as a sample collection device, a thermometer, etc. Once the user device connects to the telehealth platform, the telehealth platform can guide the user in how to use the diagnostic test kit via instructions in the form of text, visuals, and/or audio. In some embodiments, the telehealth platform can perform dynamic provider or proctor routing to connect the user device to a device of a particular provider or proctor, who may observe the user use the kit and/or provide additional guidance to the user. Once the user completes the diagnostics test or other test (e.g., the user has collected a biological sample such as saliva, blood, urine, etc.), the telehealth platform can receive data from the user device (e.g., in the form of images of the sample collection device, video, etc.)) and perform an initial analysis. In some embodiments, the data (e.g., images, video, etc.) can be transmitted from the user device during a testing procedure, for example in real time or nearly real time. In some embodiments, the telehealth platform can request that the user ship the sample or other test result to another entity, such as a laboratory. In some embodiments, a user can obtain an presumptive result during an at-home testing procedure, and can send a sample to a laboratory for confirmatory testing.

If the result comes out as negative, the telehealth platform may provide minimal subsequent instructions, such as instructing the user to re-test after a period of time, to take certain precautions, and so forth. If the result comes out as positive, the telehealth platform may provide further instructions to the user via the user device. In some embodiments, the telehealth platform provides services according to a microbenefits policy, which can include providing prescription medication at no charge or at a reduced cost and without insurance information. In some cases, avoiding reliance on insurance can reduce delay in the user receiving medication.

In another example, a user experiencing a fever may want to measure their temperature and use the telehealth platform to verify results or obtain treatment, a diagnosis, etc., based on the results. The telehealth platform can receive an image of a thermometer from a user device, but the image may not be suitable or otherwise qualify for analysis. In some embodiments, the image may be too blurry, too low contrast, etc., for use. In some embodiments, the image can be manipulated to render it suitable for use. In some embodiments, the telehealth platform can perform a series of image modification steps in order to render the received image more suitable for image analysis and can automatically determine the user's body temperature therefrom. For example, the telehealth platform may perform steps including receiving, from a user device, an image of at least a portion of a thermometer used by a user, wherein the portion of the thermometer includes one or more temperature indicator features, generating a warped image (e.g., to correct perspective or skew) based on the received image, determining that the warped image qualifies for interpretation, wherein determining that the warped image qualifies for interpretation comprises determining that one or more image characteristics of the warped image are above a predetermined threshold corresponding to each of the one or more image characteristics, generating an assist image based on the warped image, and determining a temperature of the user based on the generated assist image. Similar approaches can be used for verifying other types of results. For example, the techniques herein can be applied to a lateral flow strip image.

In another example, an employer may want to confirm that a vehicle operator (e.g., an employee or contractor) is not under the influence of drugs immediately before the vehicle operator begins operating a vehicle. In some embodiments, the telehealth platform connects to a user device of the vehicle operator and/or a device that is part of the vehicle (e.g., display, speaker, microphone, camera) or otherwise integrated with the vehicle (e.g., an electronic device permanently or semi-permanently installed in the vehicle). The telehealth platform can receive a signal from at least one of the above-mentioned devices indicating that the vehicle operator has approached or is inside the vehicle. The telehealth platform can initiate an in-vehicle drug screening procedure in which the vehicle operator uses a sensor (e.g., a breath-based sensor, a touch-based sensor, etc.) configured to measure the presence of one or more drugs, the concentration of one or more drugs, and/or both in the vehicle operator. In some embodiments, the telehealth platform can keep the vehicle locked in a non-operative state such that the vehicle operator may not operate the vehicle until passing the drug screening procedure. In some embodiments, the vehicle can be configured to remain in an inoperative state until the vehicle receives a signal from the telehealth platform indicating that the drug screening procedure has been passed. If the result is negative or under a predetermined threshold, the telehealth platform can unlock operation of the vehicle. If the result is positive or above the predetermined threshold, the telehealth platform can keep the vehicle locked in the non-operative state. In some embodiments, the telehealth platform can communicate with other devices or services. For example, the telehealth platform can automatically request a taxi (e.g., UBER, LYFT) to pick up the vehicle operator and drive them to a destination. In some embodiments, the telehealth platform can report a positive result or result above a predetermined threshold to the employer.

In some embodiments, rather than an employer, testing can be mandated by a government entity. For example, an individual who has been convicted of driving under the influence of an intoxicant can be required to pass a drug screening before the user's vehicle becomes operable.

As used herein, the term "symptom" can refer to any physical or mental feature which is regarded as indicating a condition or disease, particularly a feature that is apparent to the patient. The term may be used interchangeably herein with the terms "indication," "indicator," "sign," "mark," or "feature."

As used herein, the term "condition" can refer to a medical condition or a health impairment which results from birth, injury, or disease, including mental disorder. The term can be used interchangeably herein with the terms "cause" (e.g., the cause of the experienced symptoms), "illness," "ailment," "disease," "disability," and "disorder."

As used herein, the term "intervention" can refer to an action, solution, or approach taken to improve a situation, especially a medical condition or disorder. Examples can include a drug/medication, a diet, or an exercise regimen.

The term may be used interchangeably herein with the terms "treatment" or "treatment plan."

As used herein, the terms "automated diagnosis system" or "system" can refer to a set of interacting or interrelated elements (e.g., components, modules, hardware, software) that act according to a set of rules (e.g., frameworks, protocols, workflows) to form a unified whole for at least: capturing, processing, and evaluating user-associated information/data to determine symptoms; diagnosing causes of the symptoms; and determining interventions/treatments to address the causes. In some embodiments, the system may be implemented using a telehealth platform.

As used herein, the terms "digital diagnostic tool," "differential diagnosis tool," or "diagnostic tool" can refer to a tool that can be used by a user (e.g., on their user device) to perform one or more of the tasks associated with an automated diagnosis system. For example, a digital diagnostic tool may be embodied in a software application installed on the user device or a web-based application accessible via a browser on the user device. In some embodiments, a user can use a digital diagnostic tool to diagnose their condition, transmit the diagnosis to a telehealth platform, transmit information to the telehealth platform for use in diagnosis, or any combination thereof.

It should be noted that the systems described herein may use artificial intelligence (AI) algorithms and/or machine learning (ML) techniques to perform any tasks described herein for which AI/ML may be suitable. However, for the purpose of reducing redundancy, the tasks described herein are frequently described as being performed by the system without explicit reference to AI/ML. It should be understood that, even without explicit reference, the system may be leveraging AI/ML to provide various services or functions to the user. For example, AI/ML may be used to process audio and/or visual data provided by the user (e.g., audio recordings of coughs or images of oral ailments); compare user-provided data to normal baseline data (e.g., using a trained machine learning model) to determine abnormalities, symptoms, and conditions; use user-provided data and/or information about symptoms experienced by the user to determine likely ailments/conditions and their associated treatments; or any combination thereof. AI/ML may be used to automatically and dynamically create a list of treatments that can address or treat the ailment or symptoms experienced by a user; create a suggested set of treatments (e.g., by narrowing down the list of treatments); order/rank treatments, such as to minimize side effects and/or additional harm; and so forth. AI/ML may be used to factor clinical statistics/metrics (e.g., number needed to treat (NNT), number needed to harm (NNH), hazard ratio, etc.) into treatment decisions that can be provided to clinicians.

In the Figures, identical reference numbers identify generally similar, and/or identical, elements. Many of the details, dimensions, and other features shown in the Figures are merely illustrative of particular embodiments of the disclosed technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

Telehealth System

FIG. 1 provides a schematic diagram illustrating a patient interaction or telehealth system 100 ("system 100") leveraging an artificial intelligence or machine learning model ("AI/ML model"). The system 100 can provide AI-driven telehealth care in a variety of settings. For example, the user 101 may undergo a remotely proctored test (which can be, for example, a health or diagnostic test or a drug screening test) using a user device 102, which may be a smartphone, tablet, computer, etc., and a telehealth kit 106. The user device 102 can be equipped with a camera having a field of view 103. A plurality of providers or proctors (individually referred to as 121*a-n*, collectively referred to as "proctors 121") can be available to monitor the user 101 performing the test in real-time, to assess a recording, or both. Individual ones of the proctors 121 can be human proctors or artificial intelligence (AI) or machine learning (ML) proctors. A telehealth platform 112 can allow the proctors 121 to monitor the user 101, guide the user 101 through steps of performing the test, collect pertinent data from the user 101 while the user 101 is performing the test, etc. The user device 102, proctor devices (individually referred to as 120*a-n*, collectively referred to as "proctor devices 120") of the proctors 121, and the telehealth platform 112 can be interconnected via network 110 (e.g., via wired Internet connection, Wi-Fi, cellular data, local communication, etc.). It is appreciated that the proctors 121 may perform functions beyond the conventional role of proctors (e.g., monitoring the patient perform a test). For example, the proctors 121 can also perform functions of a patient intake personnel, a therapist, a nurse practitioner, etc.

During a telehealth session, the user 101 may perform one or more steps of the remotely proctored test (e.g., diagnostic test, drug screening) within the field of view 103 of the camera, such that such steps can be monitored by at least one of the proctors 121. In some embodiments, the proctor 121 can monitor the user 101 live (e.g., in substantially real-time). In some embodiments, the proctor 121 can access a recording of the user 101, such that monitoring does not occur in real-time. In some embodiments, each proctor 121*a-n* may monitor more than one user simultaneously. For example, in some embodiments, a single proctor 121*a* may monitor one, two, three, four, five, six, seven, eight, nine, ten, fifteen, twenty, twenty-five, fifty, any number between these numbers, or more users at a time. In some embodiments, proctors 121 may monitor the user 101 during all steps in the administration of the proctored test. In some embodiments, the user 101 may interact with the same proctor over the course of a proctored test. In some embodiments, proctors may monitor the user 101 during certain steps in the administration of the proctored test. In some embodiments, the user 101 may interact with different proctors 121 over the course of a proctored test (e.g., at different stages or steps of the session).

In some embodiments, the proctors 121 can perform patient intake procedures. For example, an AI/ML proctor can emulate a doctor's assistant and ask the user 101 various clinical questions via text, voice, video, or any combination thereof. In some embodiments, the artificial intelligence proctor generates new clinical questions to ask based on the patient interaction thus far in order to generate a more complete set of data relevant to patient intake. For example, if the user 101 mentions that they have been having a headache, the artificial intelligence proctor can follow-up by asking related questions, such as how long the headache has been lasting, other symptoms, any medication taken in the past couple of days, any recent experiences, etc.

In some embodiments, the telehealth platform 112 performs and/or facilitates order fulfillment of the test kit 106 and other telehealth products or services. At a first step, the user 101 may access a user portal. In some embodiments, the user 101 may access the user portal via a computer system or the user device 102. In some embodiments, the user portal may include a software application, website, and/or any other computer program. In some embodiments, the user 101 may access the user portal via a user account. In some embodiments, the user 101 may login to the user account and/or the user portal via a user login. In some embodiments, the user login may include a username, a user email, a password, and/or any other login information. In some embodiments, the user 101 may order one or more kits 106 via the user portal.

In some embodiments, the user 101 or another entity (e.g., an employer, a telehealth manager, etc.) may review telehealth information. In some embodiments, the telehealth information may include results of one or more prior tests, current status of tests, a number of completed tests, a number of tests in-process, a number of tests with an error, a date a test was administered, a type of the test, a shipment status of test kits/samples, where each test kit/sample is being shipped, and/or any other data or analytics. In some embodiments, the current status of tests may include indications that the test kit 106 was shipped, that the test kit 106 was received by the user 101, that the user 101 started a telehealth session, that the user 101 completed a telehealth session, that a lab test was shipped, that a lab test was received by a laboratory, that a drug screening result is ready, that a certain amount of time in a test window remains, and/or any other status of a drug screening or diagnostic test. In some embodiments, the telehealth information may include one or more videos, photos, and/or audio recordings for a telehealth session. In some embodiments, the telehealth information may include a chain of custody certificate. In some embodiments, the user 101 or another entity may access and/or download the chain of custody certificate for each drug screening. In some embodiments, the user 101 or other entity may access end-to-end session data for each telehealth session. In some embodiments, the user portal may transmit and/or receive the telehealth information to an employee management system via an application programming interface (API).

In some embodiments, the user 101 or other entity may add and/or remove other users from the user account. In some embodiments, the user 101 or other entity may limit and/or grant one or more of the other users access to one or more features of the user portal, for example, the user 101 may restrict one or more other users from ordering tests and grant the one or more other users access to view results of prior drug screenings. In some embodiments, the user 101 may limit and/or grant one or more of the other users access to specific users. In some embodiments, the user portal may update the other users access in real time or substantially real time. In some embodiments, the other users access may be updated when the other users login to the user portal a next time.

In some embodiments, after the user 101 or other entity accesses the user portal, the user 101 or other entity may place an order for one or more test kits 106. In some embodiments, the user 101 or other entity may provide user information to place the order for one or more test kits 106. In some embodiments, the user information may include, for example, a phone number, an email address, a shipping address, a name, a position, and/or any other user information.

In some embodiments, the order may include an automatic order. In some embodiments, an automatic order may include one or more periodic orders. In some embodiments, the user may input a predetermined order period. In some embodiments, the predetermined order period may include a period of about 1 day, about 2 days, about 3 days, about 4 days, about 5 days, days, about 6 days, about 1 week, about 2 weeks, about 3 weeks, about 4 weeks, about 1 month, about 2 months, about 3 months, about 4 months, about 5 months, about 6 months, about 1 years, about 2 years, about 3 years, about 4 years, about 5 years, about 10 years, and/or any other value between the aforementioned values. In some embodiments, the computer system can automatically ship or send a test kit 106 to the user 101 after the predetermined order period. For example, the user 101 or other entity may place an automatic order for the user 101 such that the user 101 receives a test kit 106 every 6 months.

In some embodiments, the automatic order may include a random order. In some embodiments, the random order may include an order for a test kit 106 for a user on a random date. In some embodiments, the random order may include multiple order for test kits 106 for a number of randomly selected users from a group of users. In some embodiments, the user 101 or other entity may select the number of randomly selected users. For example, test kits for drug screening can be sent to a randomly selected group of users.

In some embodiments, the order may include a bulk order and/or an individual order. In some embodiments, if the order includes a bulk order, the user may upload the user information for a plurality of users to the user portal. In some embodiments, the user 101 or other entity may upload the user information via a bulk order file. In some embodiments, the bulk order file may include a file format. In some embodiments, the file format may include .csv, .txt, .doc, .docx, .xls, .xlsx, .pdf, and/or any other file format. In some embodiments, the computer system may automatically and/or dynamically parse and/or extract the user information from the bulk order file.

In some embodiments, if the order includes an individual order, the user 101 or other entity may input the user information into the user portal. In some embodiments, the user portal and/or the computer system may display an order form to the user. In some embodiments, the user 101 or other entity may enter the user information into the user portal and/or the computer system via the order form.

In some embodiments, when the user 101 or other entity places an order for one or more test kits 106, the computer system may automatically generate a user account for each user of the order for one or more test kits 106. In some embodiments, the computer system may access a database of user accounts. In some embodiments, the computer system may automatically determine if a user account exists for each user. In some embodiments, if a user account exists for a user, the computer system may automatically link the order to the user account. In some embodiments, if the user account does not exist, the computer system may automatically generate a user account for the user 101.

In some embodiments, the user account may include any of the telehealth information associated with an order of a test kit 106 for the user 101. In some embodiments, the user account may include any user information of the user. In some embodiments, the user account may include any notification information, as described further below.

In some embodiments, after the user 101 or other entity places an order for one or more test kits 106, the computer system can automatically process the order. In some embodiments, the computer system can automatically associate each test kit 106 of the order with a user and/or a user account. In some embodiments, the computer system can automatically generate a tracking identifier for each test kit 106 of the order.

In some embodiments, after the computer system processes the order, the computer system can automatically transmit a notification to each user of the order. In some embodiments, the notification can include an email, a text message, a call, and/or any other form of communication. In some embodiments, the notification can include notification information. In some embodiments, the notification information may include a notice that the user 101 is scheduled for a telehealth session, a tracking number for the test kit 106, a time period for performing the telehealth session, instructions on how to access the telehealth platform 112, screening instruction, instructions for accessing and/or setting up the user account, a link to start a telehealth session, a verification code, user device constraints, and/or any other order or telehealth session information.

From the telehealth platform end, a telehealth provider may order a plurality of screening equipment from a laboratory or equipment provider. In some embodiments, the telehealth provider may receive the plurality of screening equipment from the laboratory or equipment provider. In some embodiments, the telehealth provider may package and/or assemble the equipment in kits, such as the kit 106. In some embodiments, the telehealth provider may generate identifiers and return packaging and/or any other items included in or on the kits.

In some embodiments, the telehealth provider and/or the laboratory or equipment provider may provide the kits 106 to users 101 and/or other requesting entities. In some embodiments, the telehealth provider and/or the laboratory or equipment provider may ship or send the kits 106 directly to users 101 and/or other requesting entities.

Before or after the user 101 receives the kit 106, the user 101 may access a link to start a telehealth session. In some embodiments, a notification sent to the user device 102 may include the link to start the telehealth session. In some embodiments, the link may direct the user 101 to the telehealth platform 112. In some embodiments, the telehealth platform 112 can include a website, a web application, a mobile application, any other computer software, or any combination thereof.

In some embodiments, the computer system may prompt the user 101 to login to the telehealth platform 112 to start the telehealth session. In some embodiments, the telehealth platform 112 may prompt the user 101 to input an email address and the code included in the notification. In some embodiments, the computer system may access the database of user accounts to verify the email address and the code. In some embodiments, the computer system may compare the code input by the user 101 to a code associated with the email address input by the user 101. In some embodiments, if the email address does not match any email address in the database and/or the code input by the user does not match the code associated with the email address input by the user, the computer system may prevent or inhibit the screening session from starting. In some embodiments, if the code input by the user matches the code, the computer system may start the screening session and log the user into the user account.

In some embodiments, the computer system may prompt the user login to the user account and/or complete user authorization. In some embodiments, if the user has previously accessed the user account, the computer system may prompt the user to login to the user account. In some embodiments, the user may input login information to login to the user account. In some embodiments, the login information may include a password, a biometric identifier, one or more images of the user, one or more videos of the user, and/or voice recordings of the user. In some embodiments, the computer system may compare the login information input by the user to login information stored in the database of user accounts. In some embodiments, the computer system may log the user into the user account if the login information input by the user matches login information stored in the database of user accounts. In some embodiments, the computer system may not login the user to the user account if the login information input by the user does not match login information stored in the database of user accounts.

In some embodiments, if the user has not previously accessed the user account, the telehealth platform may prompt the user to set up the user account. In some embodiments, the telehealth platform may prompt the user to set up a password, a username, and/or any other account information. In some embodiments, the computer system may prompt the user to input user identification information. In some embodiments, the user identification information may include one or more images of the user, a driver's license, a passport, and/or any other identification information.

In some embodiments, after the user logs into the user account the computer system may request authorization from the user. In some embodiments, the computer system may display a consent and/or data authorization agreement to the user. In some embodiments, the computer system may require the user to provide consent and/or accept the data automatization agreement. In some embodiments, the computer system may display a notice of drug testing program or policy to the user. In some embodiments, the computer system may display a notice of final tests results documentation to the user. In some embodiments, the notice of drug testing program or policy and/or the notice of final tests results documentation may be based on a location of the user and/or a location of the user requesting the drug screening. In some embodiments, the user may input the notice of drug testing program or policy, the notice of final tests results documentation, or both into the user portal. In some embodiments, the computer system may retrieve the notice of drug testing program or policy, the notice of final tests results documentation, or both from a database.

In some embodiments, the computer system may connect the user 101 with one or more of the proctors 121 via a video call. In some embodiments, the proctor 121 and/or the computer system may confirm an identity of the user 101. In some embodiments, the proctor and/or the computer system may prompt the user 101 to place a user ID in front of a camera of the user device 102. In some embodiments, if the user is a repeat user, the user ID can previously have been captured and stored, and the proctor, the computer system, or both can compare the user to the stored user ID. In some embodiments, the proctor 121, the computer system, or both may confirm the identity of the user 101 by comparing the user to the user ID. In some embodiments, the computer system may use computer vision (CV) to automatically analyze images or video of the user 101 and/or the user ID captured by the camera of the user device 102 to confirm the identity of the user 101. If the proctor 121 and/or the computer system is unable to confirm the identity of the user 101, the proctor 121 may end the telehealth session, or the computer system may automatically end the telehealth session. In some embodiments, the proctor 121 and/or the computer system is unable to confirm the identity of the user 101, the proctor 121 and/or the computer system may input a notification that the identity of the user 101 cannot be confirmed.

Telehealth Drug Screening

Drug screenings can be important for a variety of reasons, for example to ensure that employers are not under the influence of drugs while on the job, to ensure compliance with regulatory requirements, to enforce court orders, and so forth. While described herein largely with reference to employment-related drug screening, it will be appreciated that the approaches described herein are applicable to a wide variety of situations in which drug screening is performed.

In some cases, users, for example human relations managers and/or employers, may not have time to schedule drug screenings. In some cases, once a user is able to schedule a drug screening for a donor, the donor may have to wait for an extended period of time at a laboratory. In some cases, users may not have access to results of the drug screening. In some cases, the users may not have access to data and/or analytics for drug screenings. In some cases, users may have difficulty locating a lab to conduct drug screenings and/or may struggle to schedule drug screenings as only a limited number of testing providers may be available. In some cases, it may take several days or even weeks before an employee or other individual can undergo drug screening, leaving sufficient time for many drugs to no longer be detectable using some methods such as saliva or urine samples.

In some embodiments, as described herein, a system for telehealth drug screening may be used for employer mandated testing, such as, for example, workers' compensation or unemployment claims defense, casinos, oil and gas companies, etc. In some embodiments, the system for telehealth drug screening may be used for state mandated and/or federally mandated testing, such as, for example, for law enforcement, for probation, for civil court, for custody proceedings, for the Department of Transportation, etc.

In some embodiments, a system for telehealth drug screening may reduce or eliminate donor wait times and/or a time required by a user to schedule a drug screening. In some embodiments, the system may automatically schedule one or more drug screenings and/or automatically ship one or more drug screening kits to donors. In some embodiments, the system may automatically ship one or more drug screening kits to donors periodically. In some embodiments, the system may automatically ship one or more drug screening kits to donors every 1 day or about 1 day, 2 days or about 2 days, 3 days or about 3 days, 4 days or about 4 days, 5 days or about 5 days, 6 days or about 6 days, 1 week or about 1 week, 2 weeks or about 2 weeks, 3 weeks or about 3 weeks, 4 weeks or about 4 weeks, 1 month or about 1 month, 1 months or about 2 months, 3 months or about 3 months, 4 months or about 4 months, 5 months or about 5 months, 6 months or about 6 months, 1 year or about 1 year, 2 years or about 2 years, 3 years or about 3 years, 4 years or about 4 years, 5 years or about 5 years, 10 years or about 10 years, and/or any other value between the aforementioned values. In some embodiments, the system may automatically schedule one or more drug screenings and/or automatically ship one or more drug screening kits to one or more donors at random times.

In some embodiments, a drug screening kit may include a container and screening equipment. In some embodiments, the screening equipment may include a test panel. In some embodiments, the test panel may screen for a plurality of drugs. In some embodiments, the test panel may screen for 1 drug, 2 drugs, 3 drugs, 4 drugs, 5 drugs, 6 drugs, 7 drugs, 8 drugs, 9 drugs, 10 drugs, 11 drugs, 12 drugs, 13 drugs, 14 drugs, 15 drugs, 20 drugs, 25 drugs, 30 drugs, 35 drugs, 40 drugs, 45 drugs, 50 drugs, and/or any value between the aforementioned values.

In some embodiments, the test panel may include a sample collection device and one or more result indicators. In some embodiments, the sample collection device may retrieve or collect a sample from a donor. In some embodiments, the sample collection device may retrieve a fluid sample and/or a DNA sample from the donor. In some embodiments, the fluid sample may include saliva, urine, sweat, blood, and/or any other body fluid. In some embodiments, the sample collection device may retrieve a hair sample, the breath of the donor and/or cells from the nasopharynx of the donor.

In some embodiments, the one or more result indicators may include test strips or result strips. In some embodiments, the one or more result indicators may include a display. In some embodiments, the one or more result indicators may indicate a result of the drug screening. In some embodiments, the one or more result indicators may change color to indicate a result of the drug screening. In some embodiments, the test panel may not indicate which drug each of the one or more result indicators corresponds to. In some embodiments, the one or more result indicators may be anonymized. For example, a result indicator may not include an indication that is understandable by the donor.

In some embodiments, the proctor and/or the computer system may observe the donor collecting the sample. In some embodiments, the proctor and/or the computer system can observe the donor collecting the sample via a video call. In some embodiments, the proctor and/or the computer system may confirm an identity of the donor before the donor collects the sample. In some embodiments, the proctor and/or the computer system may analyze an image of the donor and compare the image of the donor to an image of an ID (e.g., driver's license, passport, state-issued identification, employee ID, and so forth) of the user to confirm an identity of the donor. In some embodiments, the computer system may receive biometric authentication to confirm the identity of the user. For example, the computer system can be configured to use fingerprints, iris scans, facial recognition, and/or the like to confirm the identity of the user.

In some embodiments, the drug screening kit may include a seal. In some embodiments, the seal may include a tamper proof seal. In some embodiments, the tamper proof seal may indicate if the drug screening kit or the container of the drug screening kit is modified, tampered with, or otherwise altered. In some embodiments, a proctor and/or a computer system may analyze the tamper proof seal to ensure the drug screening kit or a container of the drug screening kit is not modified, tampered with, or otherwise altered by a donor or someone else before a drug screening session.

In some embodiments, the drug screening kit, the container, the screening equipment, and/or the test panel may include an identifier. In some embodiments, the identifier may include a barcode, QR code, NFC chip, contact chip, alphanumeric code, and/or any other unique identifier. In some embodiments, the identifier may include a machine-readable code. In some embodiments, the identifier may include a serialized identifier. In some embodiments, the identifier may include a serialized QR code.

In some embodiments, the identifier may include a make and/or model of the drug screening kit. In some embodiments, the identifier may be unique or different for each drug screening kit. In some embodiments, the drug screening kit may include a plurality of identifiers. For example, a drug screening kit can include a first identifier that identifies a type, make, model, and/or the like of the drug screening kit, and can include a second identifier that can be a unique identifier of a particular drug screening kit. In some embodiments, a unique identifier for the drug screening kit can be printed, stamped, or the like on one or more components of the drug screening kit, which can enable verification that individual components (e.g., container, screening equipment, test panel, etc.) belong to the same drug screening kit.

In some embodiments, the proctor and/or the computer system may prompt the donor to scan the identifier at one or more steps throughout the drug screening process to ensure the donor does not change the drug testing kit, the screening equipment, and/or the test panel.

In some embodiments, the drug screening kit may include a stand. In some embodiments, the stand may be configured to receive and/or hold a donor device (e.g., a smartphone, tablet, laptop computer, or other suitable computing device). In some embodiments, the stand may hold the donor device while a donor is performing a drug screening. In some embodiments, the stand may position the donor device so the donor is in view of a camera of the donor device. In some embodiments, the stand may allow the donor to perform the drug screening without holding the donor device.

In some embodiments, the stand may include a portion of the container. In some embodiments, the stand may be coupled to the container. In some embodiments, the container may include one or more features, indentations, and/or extrusions that form the stand. In some embodiments, the container may be folded, bent, or otherwise modified to form the stand.

In some embodiments, the drug screening kit may include return packaging. In some embodiments, the return packaging may include a pre-paid shipping label. In some embodiments, the proctor and/or the computer system may observe the donor placing screening equipment in the return packaging. In some embodiments, the donor may place the screening equipment in the return packaging after the donor completes a drug screening or after the donor collects a sample. In some embodiments, the donor may place the screening equipment in the return packaging if the test panel and/or the one or more result indicators indicate a positive test.

In some embodiments, the donor may send the return packaging to a laboratory for confirmatory testing. In some embodiments, the donor may leave the return packaging at a delivery service. In some embodiments, a courier may pick up the return packaging from the donor. In some embodiments, the courier may deliver the return packaging to the delivery service. In some embodiments, the courier may deliver the return packaging to the laboratory. In some embodiments, the courier may deliver the return packaging to the delivery service.

In some embodiments, the return packaging may include a tamper proof seal. In some embodiments, the tamper proof seal may indicate if the return packaging is modified, tampered with, or otherwise altered before the laboratory receives the return packaging.

In some embodiments, the laboratory may perform confirmatory testing in response to a presumptive positive test result (e.g., a first test result is positive). In some embodiments, the laboratory may perform oral fluid testing and/or urine testing. In some embodiments, the laboratory may perform confirmatory testing on a second sample retrieved by a second sample collection device. In some embodiments, the donor may retrieve the second sample during the drug screening session, before the drug screening session, and/or after the drug screening session. In some embodiments, the laboratory may perform a DNA analysis on both the sample and the second sample to confirm the sample and the second sample are both from a same donor.

In some embodiments, if the laboratory confirms a presumptive positive test result of the drug screening, the laboratory and/or a computer system may determine the result of the drug screening is a confirmed positive result. In some embodiments, the computer system may automatically transmit the positive results or indication that the donor tested positive for one or more drugs to the user portal.

In some embodiments, a presumptive negative test result may not be confirmed with additional confirmatory testing. In some embodiments, a presumptive negative test result may be subject to additional confirmatory testing. For example, if a donor is suspected of drug use and tests negative, additional testing may be ordered to confirm the negative test result.

In some embodiments, a medical review officer (MRO) and/or other laboratory personnel may interpret the result of the drug screening. In some embodiments, the MRO and/or the other laboratory personnel may review the result of the drug screening indicated by one or more of the one or more result indicators and/or a result of the confirmatory testing. In some embodiments, the MRO and/or other laboratory personnel may input the confirmed positive result into the computer system. In some embodiments, the MRO and/or the other laboratory personnel may review donor information to determine if the donor information indicates a reason for the positive result of the drug screening, for example, the donor may have a prescription. In some embodiments, if the donor information indicates a reason of the positive result, the MRO and/or the other laboratory personnel may determine that the positive result of the drug screening is not confirmed, and the result of the drug screening is negative. In some embodiments, the MRO and/or other laboratory personnel may input the negative result into the computer system. In some embodiments, if there is a known reason for the positive result, the MRO and/or other laboratory personnel may perform a more specific test, if available, in order to determine if the positive result is the result of the prescription (or other factor that can result in a false positive result).

In some embodiments, records and/or chain of custody information of the drug screening session may include a name, address, phone number, and/or any other information about the MRO and/or the other laboratory personnel. In some embodiments, a user portal may display to a user the name, address, phone number, and/or any other information about the MRO and/or the other laboratory personnel.

In some embodiments, the computer system may determine a chain of custody for each drug screening kit and/or drug screening session. In some embodiments, the chain of custody may include a chain of custody form. In some embodiments, the chain of custody form may include a chain of custody and control form. In some embodiments, the chain of custody form may include a digital chain of custody form.

In some embodiments, the chain of custody form may be transmitted to the laboratory. In some embodiments, the custody form may be shipped to the laboratory or transmitted digitally to the laboratory. In some embodiments, the laboratory may review the chain of custody form to confirm the return packaging received by the laboratory corresponds to a correct donor and/or a sample included in the return packaging received by the laboratory corresponds to the correct donor.

In some embodiments, the chain of custody form may be transmitted to the user portal. In some embodiments, a user may review the chain of custody form to confirm the return packaging received by the laboratory corresponds to the correct donor and/or the sample included in the return packaging received by the laboratory corresponds to the correct donor. In some embodiments, the user may review the chain of custody form to confirm the sample used during the drug screening and/or the sample used for the confirmatory testing are both samples from the same donor.

In some embodiments, the chain of custody form may include a chain of custody tracker. In some embodiments, the chain of custody tracker may include the identifier and/or a second identifier associated with the identifier. In some embodiments, the chain of custody tracker may be used at each step of the drug screening process to confirm the drug screening kit, the screening equipment, the test panel, the sample, and/or the second sample used are correct and/or the same.

In some embodiments, the chain of custody form may include the donor information, a test method, a confirmatory test method, a test panel and/or screening equipment make or model, billing information, reporting information, MRO and/or other laboratory personnel information, proctor information, results of the confirmatory testing, a reason for the drug screening, for example pre-employment, random, reasonable suspicion, etc., and/or any other chain of custody information about the drug screening process or the drug screening kit.

In some embodiments, the chain of custody form and/or the user portal may include one or more time stamps. In some embodiments, the one or more time stamps may include a time when the identifier is scanned each time throughout a testing and/or confirmatory testing procedure, a time when the drug screening session started, a time when the donor was connected to the proctor via a video call, a time when the return packaging was picked up by a courier, a time when the return packaging was received by the delivery service, a time when the laboratory received the return packaging, a time when the confirmatory testing was performed and/or any other time.

In some embodiments, the computer system may transmit and/or receive chain of custody information and/or any other information from the laboratory via an API, an HL7 file, a JSON file, and/or any other digital communication protocol or pathway.

In some embodiments, the chain of custody information and/or any other information included on the chain of custody form may be based on a location of the user, the location of the donor, the location of the laboratory, the location of the requesting entity, and/or the location of any other party. For example, data retention requirements, chain of custody requirements, and so forth may depend on various laws and regulations which can vary across different jurisdictions.

In some embodiments, the computer system may store the chain of custody information, videos of the drug screening session, images of the drug screening session, the results of the drug screening session, the results of the confirmatory testing, and/or any other information for a period of time. In some embodiments, the period of time may include a time of 1 day or about 1 day, 1 week or about 1 week, 1 month or about 1 month, 2 months or about 2 months, 3 months or about 3 months, 4 months or about 4 months, 5 months or about 5 months, 6 months or about 6 months, 7 months or about 7 months, 8 months or about 8 months, 9 months or about 9 months, 10 months or about 10 months, 11 months or about 11 months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any value between the aforementioned values, or more.

In some embodiments, the computer system and/or the user portal may transmit a system report to the user. In some embodiments, the computer system and/or the user portal may transmit the system report to the user upon request by the user. In some embodiments, the computer system and/or the user portal may transmit the system report to the user periodically. In some embodiments, the computer system and/or the user portal may transmit the system report to the user about every 1 day, 1 week, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, and/or any value between the aforementioned values. In some embodiments, the computer system and/or the user portal may transit the system report to the user upon a new result becoming available. In some embodiments, the system report may include any chain of custody information, videos of drug screening sessions, images of drug screening sessions, results of the drug screening sessions, results of confirmatory tests, and/or any other information about any completed drug screening session over a period of time. In some embodiments, the system report may include a number of tests conducted, a number of positive test results, a number of negative test results, what drugs or substances donors tested positive for, how many screenings of each type of drug screening, and/or any other information.

In some embodiments, a user may access data and/or analytics of one or more drug screenings via a user portal. In some embodiments, the user may access the chain of custody information, videos of the drug screening session, images of the drug screening session, the results of the drug screening session, the results of the confirmatory testing, and/or any other information. In some embodiments, the user may access an order status via the user portal. In some embodiments, the user may access a system report via the user portal. In some embodiments, the system report may include any chain of custody information, videos of drug screening sessions, images of drug screening sessions, results of the drug screening sessions, results of confirmatory tests, and/or any other information about any completed drug screening session over a period of time. In some embodiments, the system report may include a number of tests conducted, a number of positive test results, a number of negative test results, what drugs or substances donors tested positive for, how many screenings of each type of drug screening, and/or any other information.

Figure 2:
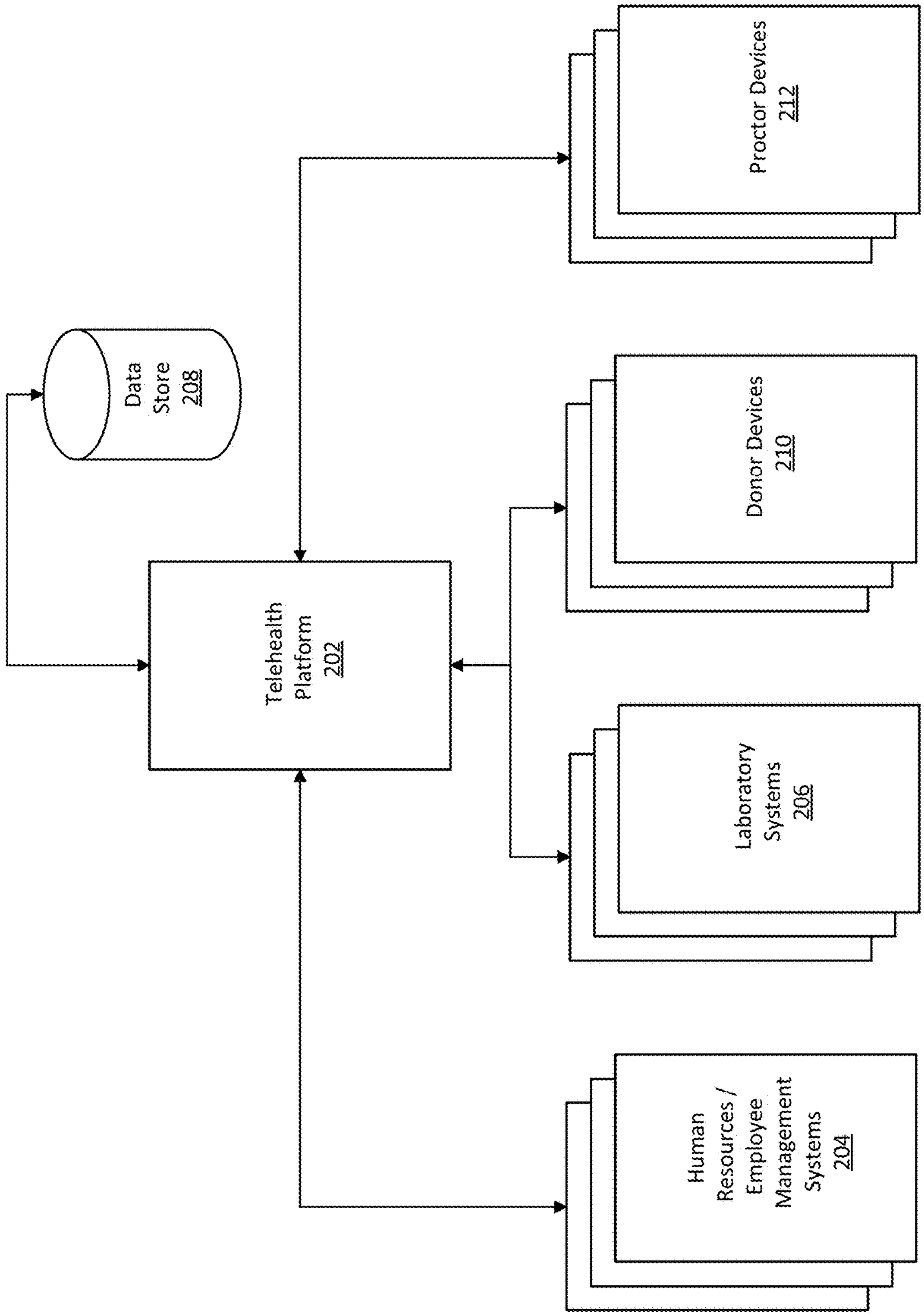
FIG. 2 shows a schematic of various systems that can be involved in drug screening according to some embodiments.

FIG. 2 shows a schematic of various systems that can be involved in drug screening according to some embodiments. As shown in FIG. 2, a telehealth platform 202 can communicate with a data store 208. The data store 208 can be used to store, for example, donor information, drug test result information, chain of custody information, test kit order information, test kit delivery information, drug test order status, and so forth. The telehealth platform can be in communication with one or more human resources/employee management systems 204, one or more laboratory systems 206, one or more donor devices 210, and/or one or more proctor devices 212. The donor devices 210 and/or proctor devices 212 can include, for example, smartphones, tablets, laptops, desktop computers, and/or the like.

Drug Screening Kit

Figure 3A:
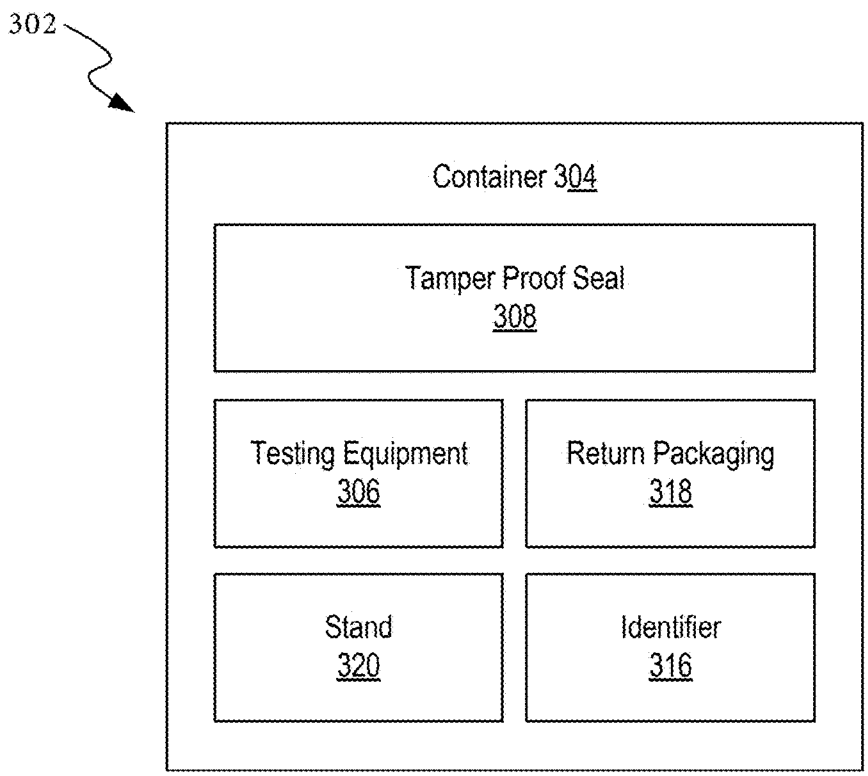
FIGS. 3A and 3B show examples of a screening kit according to some embodiments.

FIG. 3A shows a schematic of a drug screening kit 302 for telehealth drug screening. In some embodiments, the drug screening kit 302 may include a container 304 and screening equipment 306. In some embodiments, the container 304 may be adapted to hold and store contents. In some embodiments, the container 304 may be made of plastic, cardboard, metal, polymer, other material, or a combination of materials.

In some embodiments, the container 304 may include a tamper proof container and/or packaging. In some embodiments, the container 304 may include a tamper proof seal 308. In some embodiments, the tamper proof seal 308 may indicate whether a donor has modified, tampered with, or otherwise altered the container 304 and/or the tamper proof seal 308. In some embodiments, the screening equipment 306 may include the tamper proof seal 308. In some embodiments, the tamper proof seal 308 may indicate whether the donor has modified, tampered with, or otherwise altered the screening equipment 306 and/or the tamper proof seal 308.

Figure 3B:
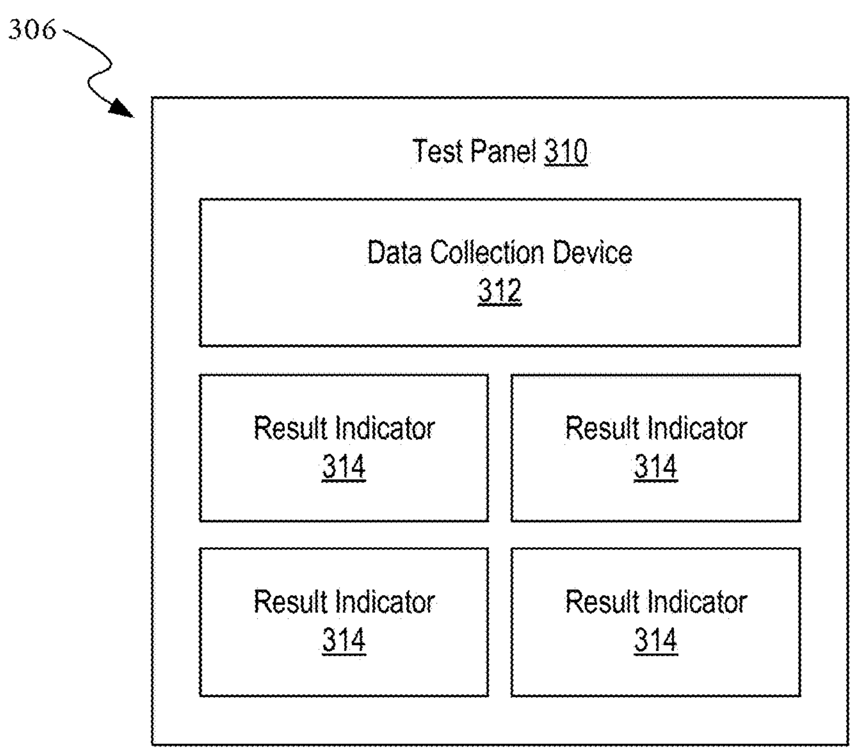

In some embodiments, the screening equipment 306 may include a test panel 310, as shown in FIG. 3B. In some embodiments, the test panel 310 may screen for a plurality of drugs. In some embodiments, the test panel 310 may screen for 1 drug, 2 drugs, 3 drugs, 4 drugs, 5 drugs, 6 drugs, 7 drugs, 8 drugs, 9 drugs, 10 drugs, 11 drugs, 12 drugs, 13 drugs, 14 drugs, 15 drugs, 20 drugs, 25 drugs, 30 drugs, 35 drugs, 40 drugs, 45 drugs, 50 drugs, and/or any value between the aforementioned values.

In some embodiments, the test panel 310 may include a sample collection device 312 (also referred to herein as a data collection device). In some embodiments, the sample collection device 312 may retrieve or collect a sample from the donor for drug screening. In some embodiments, the sample collection device 312 may retrieve a fluid sample from the donor. In some embodiments, the fluid sample may include saliva, urine, sweat, blood, and/or any other body fluid. In some embodiments, the sample collection device 312 may retrieve a hair sample from the donor. In some embodiments, the donor may breathe into the sample collection device 312 and the sample collection device 312 may collect the breath of the donor. In some embodiments, the sample collection device 312 may retrieve or collect cells from the nasopharynx of the donor.

In some embodiments, the test panel 310 may include one or more result indicators 314. In some embodiments, the one or more result indicators 314 may include test strips or result strips. In some embodiments, the one or more result indicators 314 may include one or more displays. In some embodiments, at least one of the one or more result indicators 314 may indicate whether one or more drugs are present the sample retrieved or collected by the sample collection device 312. In some embodiments, at least one of the one or more result indicators 314 can contain a fluid that changes colors, opacity, or other optical properties to indicate a result. In some embodiments, at least one of the one or more result indicators 314 may indicate detection of one or more drugs in the sample retrieved or collected by the sample collection device 312. In some embodiments, at least one of the one or more result indicators 314 may indicate an absence of one or more drugs in the sample retrieved or collected by the sample collection device 312. In some embodiments, at least one of the one or more result indicators 314 may indicate whether the results indicated by the one or more result indicators 314 are valid.

In some embodiments, at least one of the one or more result indicators 314 may change color to indicate detection of one or more drugs in the sample retrieved or collected by the sample collection device 312. In some embodiments, at least one of the one or more result indicators 314 may change from a first color to a second color to indicate detection of one or more drugs in the sample retrieved or collected by the sample collection device 312.

In some embodiments, at least one the one or more result indicators 314 may remain the first color to indicate an absence of one or more drugs in the sample retrieved or collected by the sample collection device 312. In some embodiments, at least one of the one or more result indicators 314 may change color to indicate an absence of one or more drugs in the sample retrieved or collected by the sample collection device 312. In some embodiments, at least one of the one or more result indicators 314 may change from the first color to a third color to indicate an absence of one or more drugs in the sample retrieved or collected by the sample collection device 312.

In some embodiments, at least one of the one or more result indicators 314 may remain the first color to indicate whether the results indicated by the one or more result indicators 314 are valid. In some embodiments, at least one of the one or more result indicators 314 may change color to indicate whether the results indicated by the one or more result indicators 314 are valid. In some embodiments, at least one of the one or more result indicators 314 may change from the first color to a fourth color to indicate whether the results indicated by the one or more result indicators 314 are valid.

In some embodiments, the one or more result indicators 314 may include one or more anonymized result indicators. In some embodiments, the donor may not be able to determine which drug each of the one or more result indicators 314 corresponds to.

As shown in FIG. 3A, in some embodiments, the container 304 and/or the screening equipment 306 may include an identifier 316. In some embodiments, the identifier 316 may include a barcode, QR code, NFC chip, contact chip, alphanumeric code, and/or any other unique identifier. In some embodiments, the identifier 316 may include a machine-readable code. In some embodiments, the identifier 316 may include a serialized identifier. In some embodiments, the identifier 316 may include a serialized QR code.

In some embodiments, the identifier 316 may include a make and/or model of the drug screening kit 302 and/or the screening equipment 306. In some embodiments, the identifier 316 may be unique (i.e., different) for each drug screening kit 302 and/or screening equipment 306. In some embodiments, the identifier 316 may be used for chain of custody tracking, test verification, and/or otherwise to identify the drug screening kit 302 and/or the screening equipment 306. In some embodiments, the identifier 316 may not include such information. In some embodiments, the identifier 316 can uniquely identify a test kit, testing equipment, or both, and the identifier 316 can be used to query a database or other data store to determining information about the kit, testing equipment, or both, such as make, model, manufacturing date, expiration date, a customer to associate with the kit, and so forth.

In some embodiments, the drug screening kit 302 may include return packaging 318. In some embodiments, the return packaging 318 may include a bag, a box, and/or any other container or packaging. In some embodiments, the return packaging 318 may include a return label and/or a pre-paid return label. In some embodiments, the return packaging 318 may include tamper proof return packaging. In some embodiments, the tamper proof return packaging may indicate whether the return packaging 318 was modified, tampered with, or otherwise altered before the return packaging 318 is received by a testing laboratory.

In some embodiments, the drug screening kit 302 may include a stand 320. In some embodiments, the stand 320 may be configured to receive and/or hold a donor device. In some embodiments, the stand 320 may hold the donor device while a donor is performing a drug screening. In some embodiments, the stand 320 may position the donor device so the donor is in view of a camera of the donor device. In some embodiments, the stand 320 may allow the donor to perform the drug screening without holding the donor device.

In some embodiments, the stand 320 may include a portion of the container 304. In some embodiments, the stand 320 may be coupled to the container 304. In some embodiments, the container 304 may include one or more features, indentations, and/or extrusions that form the stand 320. In some embodiments, the container 304 may be folded, bent, or otherwise modified to form the stand 320.

In some embodiments, the telehealth provider may transmit the return packaging 318 to the laboratory or equipment provider for confirmatory testing. In some embodiments, the laboratory or equipment provider may perform the confirmatory testing. In some embodiments, the telehealth provider may provide the telehealth session results and/or the results of the confirmatory testing to the user, the user portal, the requesting entity, and/or any other entity.

During a telehealth session, once the proctor and/or the computer system confirms the identity of the user, the proctor and/or the computer system may prompt the user to scan the identifier 316 of the kit 302. In some embodiments, the user may capture an image of the identifier 316 to scan the identifier 316. In some embodiments, the proctor and/or the computer system may compare the identifier 316 of the particular kit 302 to an identifier associated with the user account. In some embodiments, if the identifier 316 of the kit 302 and the identifier associated with the user account are not the same, the proctor and/or the computer system may input a notification or indication.

In some embodiments, if the identifier 316 of the kit 302 and the identifier associated with the user account are the same, the proctor and/or the computer system may start administration of the telehealth session. In some embodiments, the proctor and/or the computer system may provide the user with instructions for using the testing equipment 306 and/or the test panel 310 of the kit 302. In some embodiments, the proctor and/or the computer system may provide the user with instructions for collecting data or retrieving a sample via the data collection device 312 of the test panel 310. In some embodiments, the proctor and/or the computer system may provide the user with instructions for inputting the sample and/or the data collection device 312 into the test panel 310.

In some embodiments, the proctor and/or the computer system may observe the user performing steps of the telehealth test (e.g., sample collection, diagnostics test, drug screening, temperature measurement) to determine if the user performs administration of the test correctly and/or does not attempt to modify results of the test. In some embodiments, the computer system may analyze video captured by the user device via computer vision to determine if the user performs the test correctly and/or does not attempt to modify results of the test. In some embodiments, the proctor and/or the computer system may determine if the user collects the sample correctly, for example, inserts a swab a proper depth into the mouth of the user. In some embodiments, the proctor and/or the computer system may determine if the user has modified, tampered with, or otherwise altered tamper-proof seal 308.

In some embodiments, the proctor and/or the computer system may input a notification or indication into the telehealth system if one or more errors occur. In some embodiments, the one or more errors may include incorrect collection of the sample, modification, tempering with, or otherwise altering the tamper-proof seal 308, any of the testing equipment 306 leaving a field of view of the camera of the user device, the user leaving the field of view of the camera of the user device, and/or any other error during the test. In some embodiments, the notification or indication of one or more errors may indicate to the telehealth platform, the proctor, and/or another entity to review a recording of the administration of the test.

In some embodiments, the computer system and/or the telehealth platform may display a proctor script to the proctor via a proctor device. In some embodiments, the proctor script may include one or more instructions or prompts for the proctor to provide to the user, one or more reminders for the proctor of a tone to use when providing instructions or prompts to the user, instruction for how to handle one or more user reactions throughout administration of the test and/or any other information for the proctor.

In some embodiments, after the user administers the test, the proctor and/or the computer system may analyze results of the test. In some embodiments, the proctor and/or the computer system may prompt the user to position the test panel 310 in the field of view of the camera of the user device.

In some embodiments, as described above, the one or more result indicators 314 of the test panel 310 may include anonymized result indicators so the user may not be able to determine which drug each of the one or more result indicators 314 correspond to. In some embodiments, the proctor device may display to the proctor which drug each of the one or more result indicators 314 corresponds to. In some embodiments, the computer system may display text or graphics to indicate to the proctor which drug each of the one or more result indicators 314 correspond to. In some embodiments, the computer system may display one or more graphics overlayed on one or more images or video captured by the camera of the user device.

In some embodiments, the proctor may analyze the one or more images or video captured by the camera of the user device to determine a result of the test indicated by one or more of the one or more result indicators 314. In some embodiments, the computer system may use computer vision (CV) to automatically analyze the one or more images or video captured by the camera of the user device. In some embodiments, the computer system may use CV to automatically determine the result of the test indicated by one or more of the one or more result indicators 314. In some embodiments, both the proctor and the computer system may analyze the one or more images or video captured by the camera of the user device to determine the result of the drug screening indicated by one or more of the one or more result indicators 314.

In some embodiments, if none of the one or more result indicators 314 indicate detection of one or more conditions and/or drugs or all of the one or more result indicators 314 indicate an absence of one or more conditions and/or drugs, the proctor and/or the computer system may end the telehealth session. In some embodiments, if at least one of the one or more result indicators 314 do not indicate detection of one or more conditions and/or drugs or at least one of the one or more result indicators 314 indicate an absence of one or more conditions and/or drugs, the proctor and/or the computer system may end the telehealth session.

In some embodiments, if one or more result indicators 314 indicate detection of one or more conditions and/or drugs, the proctor and/or the computer system may determine that the indication is a presumptive positive. In some embodiments, a presumptive positive result can be confirmed by a laboratory. In some embodiments, if one or more result indicators 314 indicate detection of one or more conditions and/or drugs, the proctor and/or the computer system may indicate to the user that the test panel 310 and/or one or more result indicators 314 indicated a non-negative result. In some embodiments, the proctor and/or the computer system may instruct the user to place the test panel 310 and/or any other of the testing equipment 306 in the return packaging 318. In some embodiments, the proctor and/or the computer system can instruct the user to collect an additional sample and place the additional sample in the return packaging 318. In some embodiments, the proctor and/or the computer system may observe the user placing the test panel 310, any other of the testing equipment 306, an additional sample, or any combination thereof in the return packaging 318. In some embodiments, the proctor and/or the computer system may determine if the user attempts to modify, tamper with, or otherwise alter the test panel 310, any other of the testing equipment 306, the additional sample, the return packaging 318, or any combination thereof. In some embodiments, if the proctor and/or the computer system determine that the user attempts to modify, tamper with, or otherwise alter the test panel 310, any other of the testing equipment 306, the additional sample, the return packaging 318, or any combination thereof, the proctor and/or the computer system may input a notification and/or an indication of the same. The notification or indication can become part of a record associated with the telehealth session.

In some embodiments, the proctor and/or the computer system may prompt the user to scan the identifier 316 of the kit 302 and/or the return packaging 318 to confirm the kit 302 and/or the return packaging 318 are the correct kit and/or return packaging. In some embodiments, the proctor and/or the computer system may prompt the user to scan the identifier 316 of the kit 302 to confirm the kit 302 the user placed in the return packaging 318 is a same kit the user used for the test. In some embodiments, the proctor and/or the computer system may prompt the user to scan the identifier 316 of return packaging 318 to confirm the return packaging 318 is the return packaging associated with the kit 302 and/or the testing equipment 306.

In some embodiments, the proctor and/or the computer system may prompt or instruct the user to ship, transmit, or otherwise send the return packaging 318 to a laboratory. In some embodiments, the proctor and/or the computer system may prompt the user to capture one or more images or videos of the return packaging 318 after the user places the test panel 310 and/or any other of the testing equipment 306 in the return packaging 318. In some embodiments, the proctor and/or the computer system may prompt the user capture one or more images or videos of the return packaging 318 before the user ships, transmits, or otherwise sends the return packaging 318 to the laboratory. In some embodiments, the proctor and/or the computer system may prompt or instruct the user to take the return packaging 318 to a delivery service, for example, FEDEX, UPS, USPS, etc.

In some embodiments, a courier may retrieve or pick-up the return packaging 318 from the user. In some embodiments, the computer system may prompt the courier to capture one or more images or videos of the return packaging 318. In some embodiments, the courier may take the return packaging 318 to the delivery service.

In some embodiments, the delivery service and/or the computer system may assign a tracking number to the return packaging 318. In some embodiments, the computer system may automatically retrieve the tracking number and/or other delivery information for the return packaging 318 from the delivery service. In some embodiments, the computer system may automatically retrieve the tracking number and/or delivery information via an API. In some embodiments, the computer system may use the tracking number and/or delivery information for chain of custody.

In some embodiments, the laboratory may receive the return packaging 318. In some embodiments, if the return packaging 318 is modified, tampered with, or otherwise altered when the laboratory receives the return packaging 318, the laboratory may input a notification and/or indication of the same.

In some embodiments, the laboratory may perform confirmatory testing on the sample retrieved by the data collection device 312. In some embodiments, the laboratory may perform oral fluid testing and/or urine testing. In some embodiments, the laboratory may perform confirmatory testing on a second sample retrieved by a second data collection device 312. In some embodiments, the user may retrieve the second sample during the drug screening session, before the drug screening session, and/or after the drug screening session. In some embodiments, the laboratory may perform a DNA analysis on both the sample and the second sample to confirm the sample and the second sample are both from a same user.

In some embodiments, if the laboratory confirms the presumptive positive of the drug screening, the laboratory and/or the computer system may determine the result of the drug screening is a confirmed positive result. In some embodiments, the computer system may automatically transmit the positive results or indication that the user tested positive for one or more drugs to the user portal or otherwise makes the results or indication available in the user portal.

In some embodiments, a medical review officer (MRO) and/or other laboratory personnel may interpret the result of the drug screening. In some embodiments, the MRO and/or the other laboratory personnel may review the result of the drug screening indicated by one or more of the one or more result indicators 314 and/or a result of the confirmatory testing. In some embodiments, the MRO and/or the other laboratory personnel may input the confirmed positive result into the computer system. In some embodiments, the MRO and/or the other laboratory personnel may review user information to determine if the user information indicates a reason for the positive result of the drug screening, for example, the user may have a prescription. In some embodiments, if the user information indicates a reason of the positive result, the MRO and/or the other laboratory personnel may determine that the positive result of the drug screening is not confirmed, and the results of the drug screening is negative. In some embodiments, the MRO and/or the other laboratory personnel may input the negative result into the computer system.

In some embodiments, any records or the chain of custody of the drug screening session may include a name, address, phone number, and/or any other information about the MRO and/or the other laboratory personnel. In some embodiments, the user portal may display to a user the name, address, phone number, and/or any other information about the MRO and/or the other laboratory personnel.

In some embodiments, the computer system may transmit any of the notifications and/or the indications input by the proctor, the laboratory, and/or the computer system at any point in time. In some embodiments, a user may review images, videos, and/or any other information about the drug screening session based on the notifications and/or the indications.

In some embodiments, the computer system may transmit any results of the drug screening session and/or the confirmatory testing to a user and/or the user via an email, a text message, a call, and/or any other form of communication. In some embodiments, the results may include a file format. In some embodiments, the file format may include .csv, .txt, .doc, .docx, .xls, .xlsx, .pdf, and/or any other file format.

In some embodiments, the computer system may automatically update the chain of custody and/or a digital audit trail throughout. In some embodiments, the chain of custody and/or the digital audit trail may be displayed to the user via a user portal.

Drug Screening Kit Order Fulfillment

Figure 4:
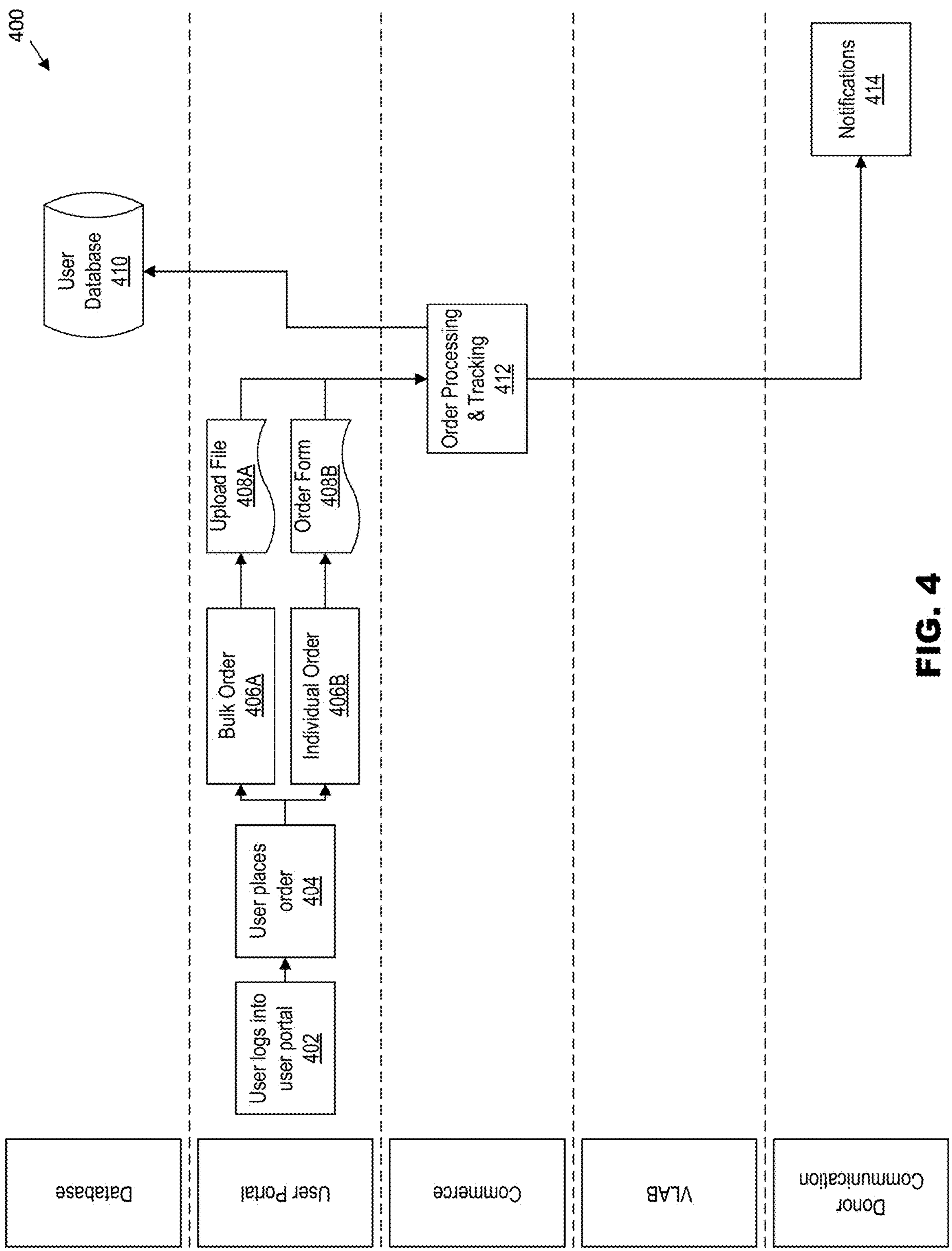
FIG. 4 shows a schematic of a method for drug screening kit order fulfillment according to some embodiments.

FIG. 4 shows a schematic of a method 400 for drug screening kit order fulfillment according to some embodiments. In some embodiments, at step 402 a user may access a user portal. In some embodiments, the user may access the user portal via a computer system. In some embodiments, the user portal may include a software application, website, and/or any other computer program. In some embodiments, the user may access the user portal via a user account. In some embodiments, the user may login to the user account and/or the user portal via a user login. In some embodiments, the user login may include a username, a user email, a password, and/or any other login information. In some embodiments, the user may order drug screening kits (e.g., screening kits 302) via the user portal.

In some embodiments, the user may review drug screening information. In some embodiments, the drug screening information may include results of prior drug screenings, a current status of drug screenings, a number of completed drug screenings, a number of drug screenings in-process, a number of drug screenings with an error, a date a drug screening was administered, a type of the drug screening, a shipment status of drug screenings, where each drug screening is being and/or has been shipped, and/or any other data or analytics. In some embodiments, the current status of drug screening may include that a drug screening kit 302 was shipped, a drug screening kit 302 was received by a donor, a donor started a drug screening session, a donor completed a drug screening session, a lab test was shipped, a lab test was received by a laboratory, a drug screening result is ready, a remaining time in a test window, and/or any other status of the drug screening. In some embodiments, the drug screening information may include one or more videos, photos, and/or audio recordings for a drug screening session. In some embodiments, the drug screening information may include a chain of custody certificate. In some embodiments, the user may access and/or download the chain of custody certificate for each drug screening. In some embodiments, the user may access end-to-end session data for each drug screening.

In some embodiments, the user portal may transmit and/or receive the drug screening information to an employee management system via an application programming interface (API).

In some embodiments, the user may add and/or remove other users from the user account. In some embodiments, the user may limit and/or grant one or more of the other users access to one or more features of the user portal, for example, the user may restrict one or more other users from ordering tests and grant the one or more other users access to view results of prior drug screenings. In some embodiments, the user may limit and/or grant one or more of the other users access to specific donors (e.g., a manager may have access to information about donors who are direct reports to the manager). In some embodiments, the user portal may update the other users' access in real time or substantially real time. In some embodiments, the other users' access may be updated when the other users login to the user portal a next time.

In some embodiments, the computer system may store chain of custody information, videos of a drug screening session, images of the drug screening session, results of the drug screening session, results of the confirmatory testing, and/or any other information. In some embodiments, the computer system may store chain of custody information, videos of a drug screening session, images of the drug screening session, results of the drug screening session, results of the confirmatory testing, and/or any other information for a period of time. In some embodiments, the period of time may include a time of 1 day or about 1 day, 1 week about 1 week, 1 month or about 1 month, 2 months or about 2 months, 3 months or about 3 months, 4 months or about 4 months, 5 months or about 5 months, 6 months or about 6 months, 7 months or about 7 months, 8 months or about 8 months, 9 months or about 9 months, 10 months or about 10 months, 11 months or about months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any value between the aforementioned values, or more.

In some embodiments, after the user accesses the user portal at step 402, the user may place an order for one or more drug screening kits (e.g., screening kits 302) at step 404. In some embodiments, the user may provide donor information to place the order for one or more drug screening kits. In some embodiments, the donor information may include, for example, a phone number, an email address, a shipping address, a name, a position, and/or any other donor information.

In some embodiments, the order may include an automatic order. In some embodiments, an automatic order may include one or more periodic orders. In some embodiments, the user may input a predetermined order period. In some embodiments, the predetermined order period may include a period of 1 day or about 1 day, 2 days or about 2 days, 3 days or about 3 days, 4 days or about 4 days, 5 days or about 5 days, 6 days or about 6 days, 1 week or about 1 week, 2 weeks or about 2 weeks, 3 weeks or about 3 weeks, 1 month or about 1 month, 2 months or about 2 months, 3 months or about 3 months, 4 months or about 4 months, 5 months or about 5 months, 6 months or about 6 months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any other value between the aforementioned values, or more. In some embodiments, the computer system can automatically ship or send a drug screening kit to a donor after the predetermined order period. For example, the user may place an automatic order for a donor such that the donor receives a drug screening kit 302 every 6 months.

In some embodiments, the automatic order may include a random order. In some embodiments, the random order may include an order for a drug screening kit (e.g., screening kit 302) for a donor on a random date. In some embodiments, the random order may include multiple orders for drug screening kits for a number of randomly selected donors from a group of donors. In some embodiments, the user may select the number of randomly selected donors.

In some embodiments, the order may include a bulk order 406A and/or an individual order 406B. In some embodiments, if the order includes a bulk order 406A, the user may upload the donor information for a plurality of donors to the user portal. In some embodiments, the user may upload the donor information via a bulk order file 408A. In some embodiments, the bulk order file 408A may be provided in a particular format. In some embodiments, the file format may include .csv, .txt, .doc, .docx, .xls, .xlsx, .pdf, and/or any other file format. In some embodiments, the computer system may automatically and dynamically parse and/or extract the donor information from the bulk order file 408A.

In some embodiments, a system can be configured to communicate with one or more human resources or human relations systems (hereinafter HR systems). For example, the system can be configured to communicate with one or more HR systems using an application programming interface (API). In some embodiments, the system can query the one or more HR systems to obtain information about donors (e.g., information about employees of a company). Information can include, for example, employee name, date of birth, job role, contact information, and so forth.

In some embodiments, the system can be configured to automatically generate testing plans, testing schedules, and so forth based on donor information (e.g., donor information uploaded by users and/or donor information obtained from one or more HR systems). For example, in some embodiments, the system can be configured to schedule drug screenings based on job role. For example, truck drivers, heavy machinery operators, and so forth can be automatically scheduled for more frequent screenings than other donors who do not operate dangerous equipment on a regular basis.

In some embodiments, the system can be integrated into a hiring or onboarding process of an HR system (which can be the same as or different from an HR system used for current employees). For example, as part of an onboarding process or pre-employment process for an individual, the system can be configured to automatically arrange a drug test for the individual. For example, the system can be configured to automatically cause a drug screening kit to be sent to the individual, can automatically notify the individual of the need to perform the drug screening, and so forth. In some embodiments, results of the drug screening can be made available to the HR system. For example, the results can be automatically uploaded to the HR system and/or the HR system can access the test results via an API. In some embodiments, it can be preferable not to upload results into the HR system itself, as doing so can increase the risk that results are mishandled or can be accessed by unauthorized users. In some embodiments, a user of the HR system can receive a notification, link, and/or the like to enable the user to sign in to a user portal of a drug screening platform to view the results of the drug screening.

In some embodiments, if the order includes an individual order 406B, the user may input the donor information into the user portal. In some embodiments, the user portal and/or the computer system may display an order form 408B to the user. In some embodiments, the user may enter the donor information into the user portal and/or the computer system via the order form 408B.

In some embodiments, when the user places an order for one or more drug screening kits 302 at step 404, the computer system may automatically generate a donor account in donor account data store 410 for each donor of the order for one or more drug screening kits at step 412. In some embodiments, the computer system may access a database of donor accounts. In some embodiments, the computer system may automatically determine if a donor account exists for each donor. In some embodiments, if a donor account exists for a donor, the computer system may automatically link the order to the donor account. In some embodiments, if the donor account does not exist, the computer system may automatically generate a donor account for the donor, for example in the data store 410.

In some embodiments, the donor account may include any of the drug screening information associated with an order of a drug screening kit for the donor. In some embodiments, the donor account may include any donor information of the donor, such as name, date of birth, address, phone number, email address, employer name, license number, and/or the like. In some embodiments, the donor account may include any notification information, as described further below.

In some embodiments, after the user places an order for one or more drug screening kits at step 404, the computer system can automatically process the order at step 412. In some embodiments, the computer system can automatically associate each drug screening kit 302 of the order with a donor and/or a donor account. In some embodiments, the computer system can automatically generate a tracking identifier for each drug screening kit of the order.

In some embodiments, after the computer system processes the order at step 412, the computer system can automatically transmit a notification to one or more donors of the order at step 414. In some embodiments, the notification can include an email, a text message, a call, and/or any other form of communication. In some embodiments, the notification can include notification information. In some embodiments, the notification information may include a notice that the donor is scheduled for a drug screening, a tracking number for the drug screening kit 302, a time period for performing the drug screening, instructions on how to access a telehealth platform, screening instruction, instructions for accessing and/or setting up the donor account, a link to start a screening session, a verification code, donor device constraints, and/or any other order or drug screening session information. In some embodiments, a notification can be sent shortly (e.g., immediately) after the order is placed. In some embodiments, a notification may be sent later, such as shortly before or after the drug screening kit 302 is delivered to the donor. Such an approach may be desirable because, for example, if a donor is given advance notice of a drug screening, the donor may have an opportunity to allow any illicit substances to clear from their body prior to taking the drug screening. For example, for a drug test that uses an oral swab for sample collection, illicit substances may only be detectable for from a few hours to about two days after ingestion. For urine-based testing, illicit substances may be detectable for from about a day to about a week, or potentially longer in the case of chronic users.

In some embodiments, a drug screening kit can be sent well in advance of a donor being asked to perform drug screening. For example, a drug screening kit can be delivered to a donor a week, a month, six months, or even longer if desired, before the donor is asked to perform drug testing. This can help avoid a negative result arising from a temporary cessation of drug usage by a donor who knows they will soon be tested.

By sending notifications shortly before a donor is to be screened for drugs and/or by shipping a drug screening kit far in advance of a required drug screening, employers, government officials, and so forth can maintain an element of surprise that can reduce the likelihood of someone being able to elude detection.

Figure 5:
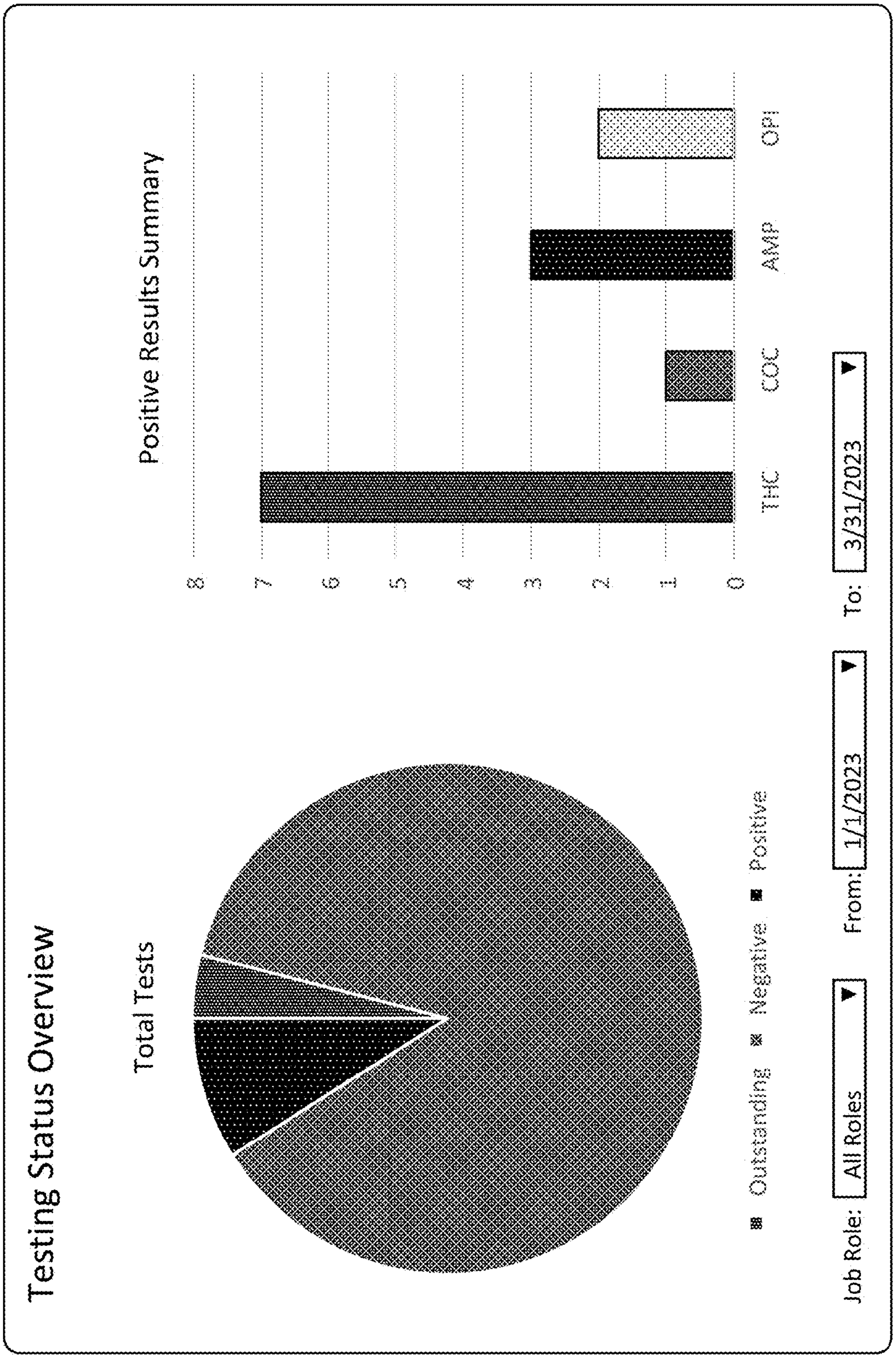
FIG. 5 shows an example interface for a user portal according to some embodiments.

FIG. 5 shows an example interface for a user portal according to some embodiments. As shown in FIG. 5, the interface can include a testing status overview that indicates, for example, a total number of tests, a number of positive tests, a number of negative tests, and a number of outstanding tests (e.g., tests that have not yet been delivered, taken, and/or processed). The interface can include a summary of positive results. For example, as shown in FIG. 5, the interface can include a bar graph or other representation that shows the number of positive test results. In some embodiments, the positive test results can be broken down by, for example, specific drugs or drug categories. In the example interface of FIG. 5, the bar chart shows the number of tests that were positive for THC, cocaine (COC), amphetamines (AMP), and opiates (OPI). It will be appreciated that other categorizations, groupings, and so forth are possible.

In some embodiments, the user interface can include one or more filtering options. For example, as shown in FIG. 5, filtering options can include job roles and/or a time period. Other filtering is also possible. For example, in some embodiments, a user can filter by job location, shift (e.g., day shift, night shift, etc.), and so forth.

FIG. 6 illustrates an example testing status board interface according to some embodiments. As shown in FIG. 6, the testing status board interface can include a table listing the names of donors and various information related to drug screening of each donor. For example, as shown in FIG. 6, the testing status board interface can include indications that a drug screening test has been ordered for a donor, shipped to the donor, delivered to the donor, completed by the donor, and so forth. The testing status board can indicate whether the donor tested positive or negative. In some embodiments, a user can click a button, link, and/or the like to obtain additional details, to take additional actions (e.g., to request an additional test), and so forth.

Figure 7:
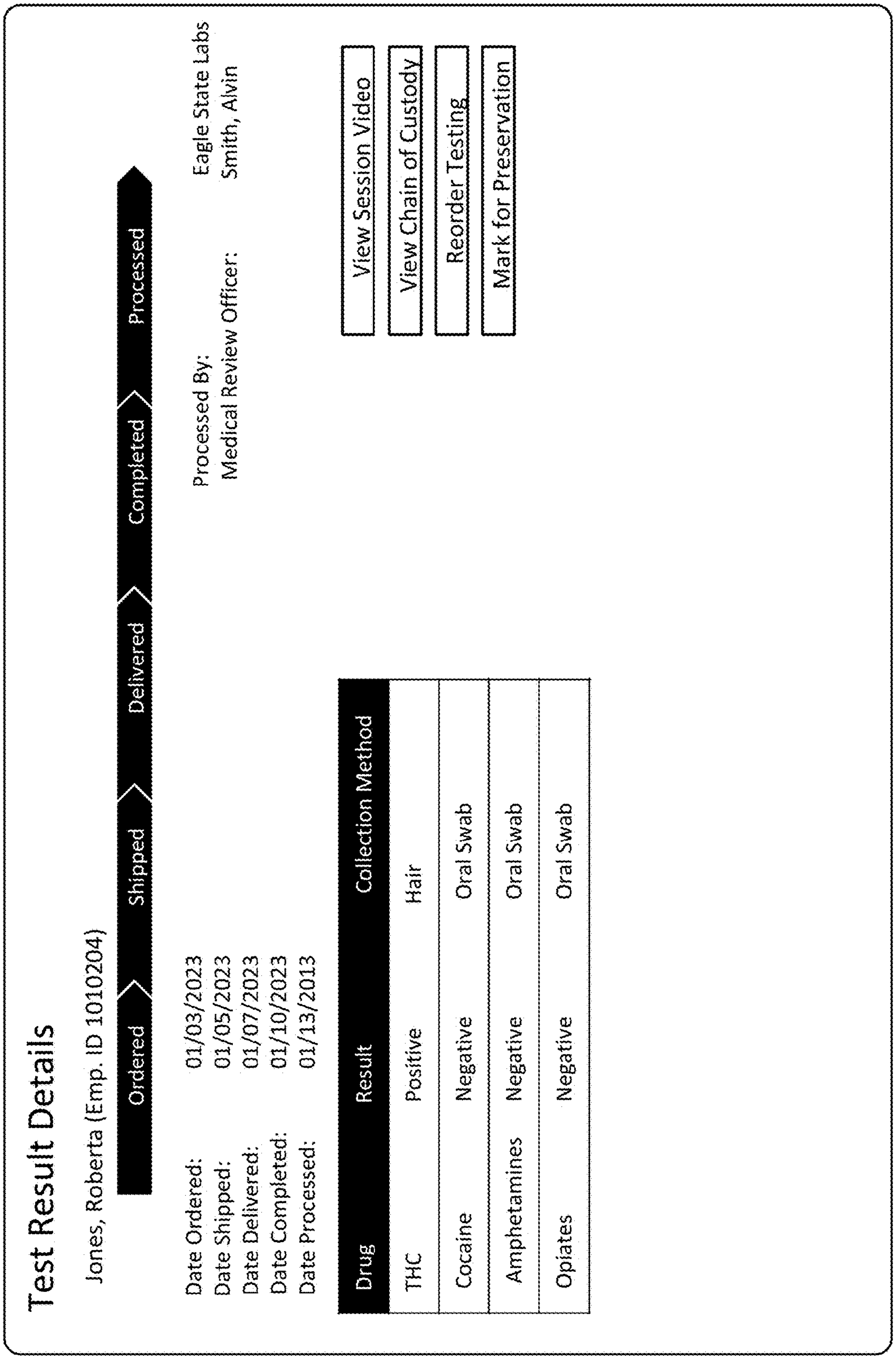
FIG. 7 shows an example interface that can be used to view test result details and/or to take additional actions according to some embodiments.

FIG. 7 shows an example interface that can be used to view test result details and/or to take additional actions. As shown in FIG. 7, the test result details interface can indicate that a drug test has been ordered, shipped, delivered, completed, and/or processed. The test result details interface can indicate the dates of various significant events, such as when the test was ordered, shipped, delivered, completed by the donor, and/or processed by a lab. The test result interface can include details about the testing such as for which drugs the donor was tested, a test result associated with each drug, sample collection method (e.g., oral swab, blood, breath, urine, hair sample, etc.), and so forth.

In some embodiments, the interface can include links or buttons to allow a user to view video of the drug screening session, to view chain of custody information (e.g., a chain of custody form), to reorder testing (e.g., a donor who tests positive may be required to take a second drug test prior to further action (e.g., employment termination)) being taken. In some embodiments, a user may mark a test result for preservation. As discussed in more detail below, it can be important to maintain records of drug testing, especially when decisions rest on the drug testing results. For example, if a donor tests positive on a pre-employment drug screening, that donor may be denied the job. If an existing employee tests positive on a drug screening, the employee may be subject to various actions such as reassignment, being ordered to attend drug counseling or treatment as a condition of employment, being terminated, and so forth.

Figure 8:
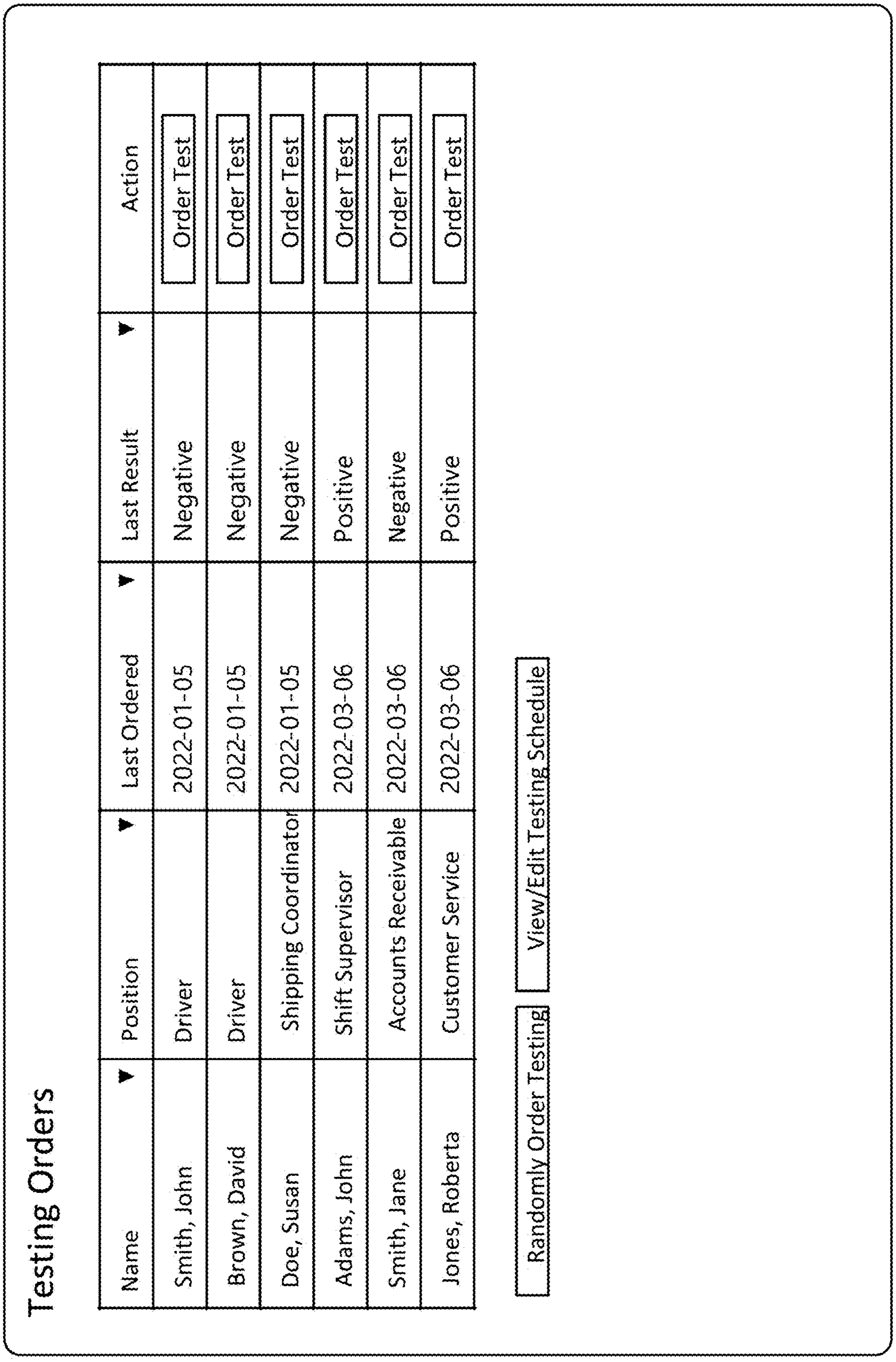
FIG. 8 illustrates an example interface that can be used to order drug screening according to some embodiments.

FIG. 8 illustrates an example interface that can be used to order drug screening according to some embodiments. As shown in FIG. 8, a testing order interface can include a list of employees for whom drug screening can be ordered (which can be provided to a drug screening platform in the form of a file, via an API tie-in to an HR system, manually input, or by any other method). In some embodiments, the interface can include a position for each employee, a date when the employee was last tested, and/or a last test result. In some embodiments, the interface can include filters that enable a user to sort by one or more columns, exclude one or more positions, show only employees that have not been tested within a particular time frame, and so forth. Such features can enable the user to quickly filter through a potentially large list of employees to identify specific employees for whom testing is to be ordered. In some embodiments, the user can click a button, link, or the like to order drug testing for a donor.

While it can be important to be able to order individual tests, for example after an accident, when an employee's behavior is concerning (e.g., missing work, showing up late, leaving early, being inattentive on the job, and so forth), and so forth, it may be prohibitively time consuming for HR professionals or other users to manually administer a drug screening program. The interface can include features that enable the user to order random testing and/or to view/edit a drug testing schedule.

While FIG. 8 shows an interface for ordering tests for existing employees, similar approaches can be used in other contexts. For example, the interface could instead be populated with a list of parolees who are subject to drug screening. The list can be populated by communicating with a data source containing information about the parolees, could be populated as a result of a user uploading a file containing information about the parolees, and/or could be populated via manual input. As another example, in some embodiments, the list could comprise potential employees.

In some embodiments, drug screening can be ordered without the use of a user interface such as the user interface of FIG. 8. For example, in some embodiments, an API can be used to integrate directly with an HR system such that, for example, when a new employee is hired, drug screening for the new employee is automatically ordered, employees are placed on a regular or randomized drug screening program, and/or the like.

Figure 9:
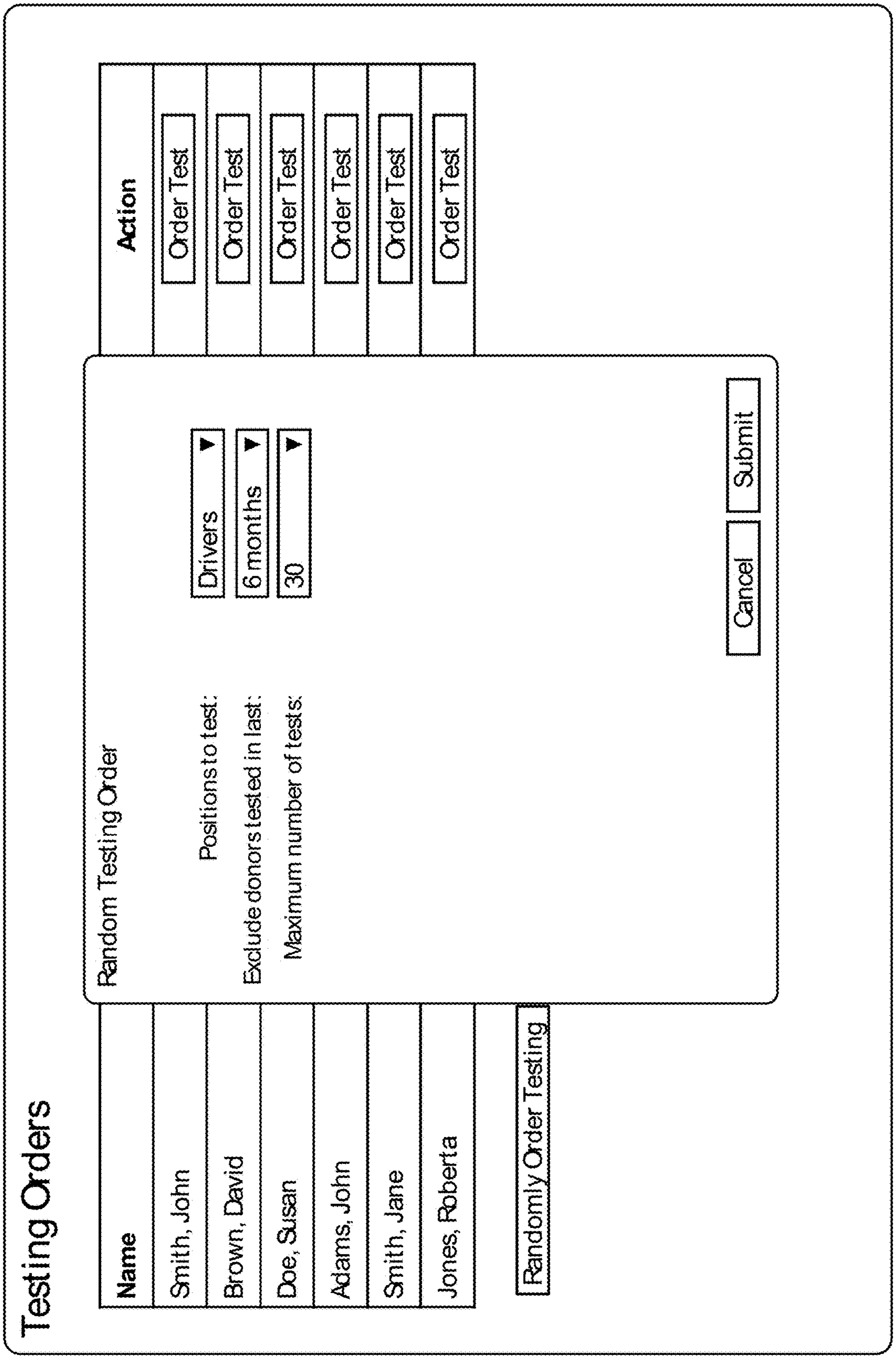
FIG. 9 illustrates an example random testing order interface according to some embodiments.

FIG. 9 illustrates an example random testing order interface according to some embodiments. As shown in FIG. 9, the interface can allow the user to select positions to test (e.g., drivers, customer service, all employees, etc.). In some embodiments, the user can exclude certain employees, for example employees that were tested in the last week, last month, last three months, last six months, last one year, last two years, and so forth, or any other time period. In some embodiments, the user can specify a maximum number of tests. For example, an organization may have budgeted for a limited number of tests. In some embodiments, if the maximum number of tests exceeds the number of employees matching other criteria, every employee matching the criteria can be tested. In some embodiments, a system can be configured to warn the user that the maximum number of tests exceeds the number of matching employees, in which case the user may choose to continue or may wish to alter the maximum number of tests to a smaller number (e.g., to a number that is less than the number of employees matching the criteria). In some embodiments, the user may choose to increase the number of matchings by broadening the criteria used for selecting employees to be tested. In some embodiments, the user may not increase the maximum number of tests, and tests can be randomly assigned to users matching the criteria. In some cases, the user can tighten the criteria so that fewer individuals match the criteria.

Figure 10:
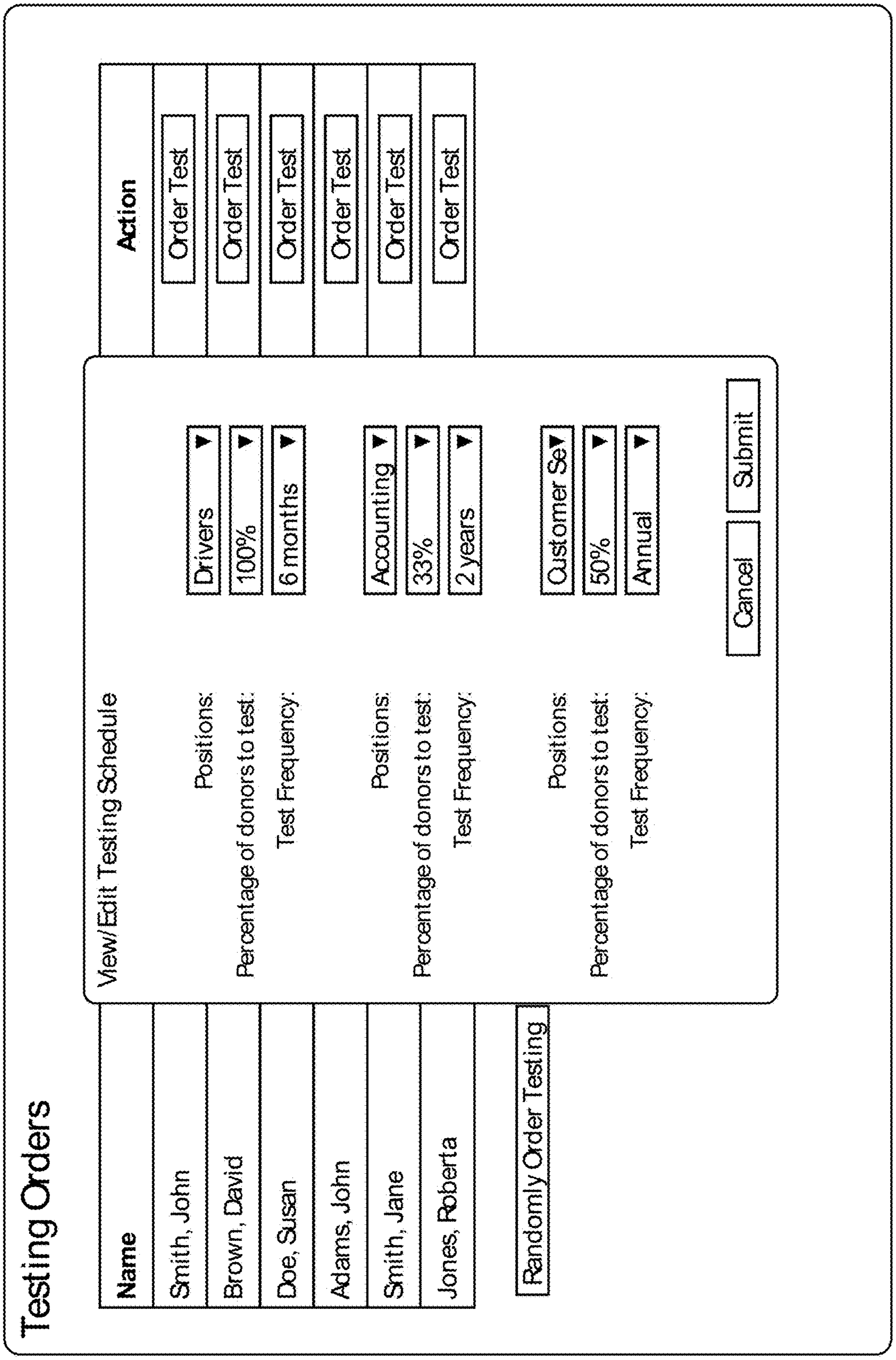
FIG. 10 illustrates an example interface for viewing and/or editing a testing schedule according to some embodiments.

FIG. 10 illustrates an example interface for viewing and/or editing a testing schedule according to some embodiments. As shown in FIG. 10, a user can be provided with various options for defining a testing schedule. For example, as shown in FIG. 10, the user can specify different groups of employees, different numbers of employees to be tested, and/or testing frequencies for different groups of employees. For example, as shown in FIG. 10, a testing schedule can include testing all drivers every six months, testing one third of accounting employees every two years (e.g., after six years, approximately all accounting employees may have been tested), and testing half of customer service employees each year. Using such an approach, a drug screening platform can automatically manage ordering tests for employees in a manner consistent with the employer's testing needs, budget, and so forth. Advantageously, users (e.g., HR employees) do not need to be involved in routine drug testing processes. Users can simply review results as they become available and can take appropriate action in response to those results.

Proctored Drug Screening

Figure 11:
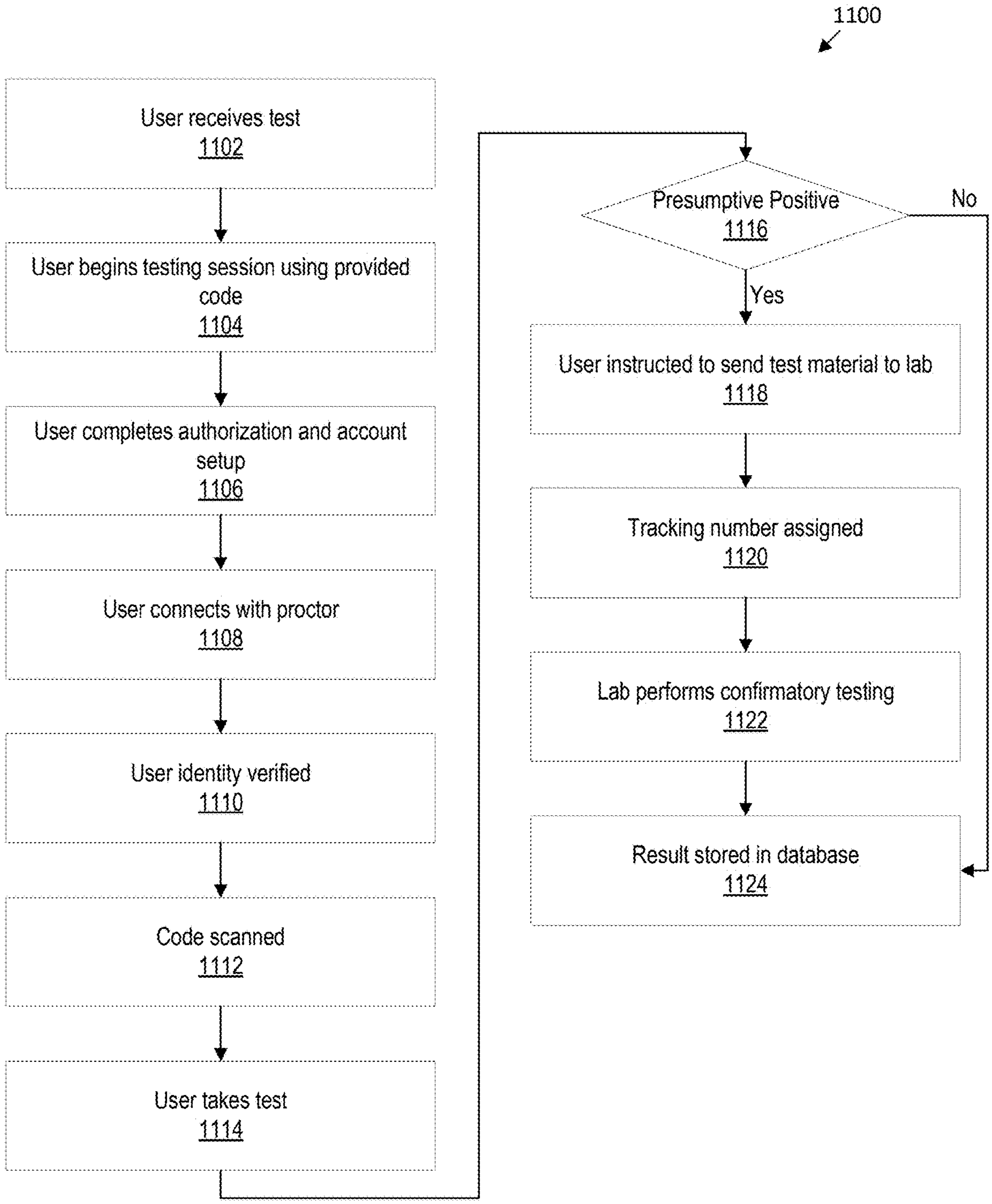
FIG. 11 shows a schematic of a method for proctored drug screening according to some embodiments.

FIG. 11 shows a schematic of a method 1100 for proctored drug screening. In some embodiments, at step 1102, a donor may receive a drug screening kit (e.g., screening kit 302). In some embodiments, after the donor receives the drug screening kit, the donor may access a link to start a screening session, at step 1104. In some embodiments, as described above with reference to FIG. 4, the notification sent to the donor at step 414 may include the link to start the screening session. In some embodiments, the link may direct a donor to a telehealth platform. In some embodiments, the telehealth platform may be a website, a web application, mobile application, and/or any other computer software.

In some embodiments, the computer system may prompt the donor to login to the telehealth platform to start the screening session. In some embodiments, the telehealth platform may prompt the donor to input an email address and the code included in the notification. In some embodiments, the computer system may access a database of donor accounts to verify the email address and the code. In some embodiments, the computer system may compare the code input by the donor to a code associated with the email address input by the user. In some embodiments, if the email address does not match any email address in the database and/or the code input by the user does not match the code associated with the email address input by the user, the computer system may prevent or inhibit the screening session from starting. In some embodiments, if the code input by the user matches the code associated with the email address input by the user, the computer system may start the screening session and log the donor into the donor account. In some embodiments, the system can be configured to accept other inputs. For example, the system can be configured to accept only a code, to accept a code and identifying information such as date of birth, employee identification number, phone number, name, etc. In some embodiments, the system can proceed if the code matches the code associated with a donor having matching identifying information. In some embodiments, the system may not proceed if the information does not match. In some embodiments, the system can be configured to provide a warning or other alert to the donor if information does not match.

In some embodiments, at step 1106, the computer system may prompt the donor to login to the donor account and/or complete donor authorization. In some embodiments, if the donor has previously accessed the donor account, the computer system may prompt the donor to login to the donor account. In some embodiments, the donor may input login information to login to the donor account. In some embodiments, the login information may include a password, a biometric identifier, one or more images of the donor, one or more videos of the donor, and/or one or more voice recordings of the donor. In some embodiments, the computer system may compare the login information input by the donor to login information stored in the database of donor accounts. In some embodiments, the computer system may log the donor into the donor account if the login information input by the donor matches login information stored in the database of donor accounts. In some embodiments, the computer system may not login the donor to the donor account if the login information input by the donor does not match login information stored in the database of donor accounts.

In some embodiments, the system can be configured to use multifactor authentication to complete a login process. For example, the system can be configured to send an email with a code to an email address associated with the donor, to send a code to a phone number associated with the donor (e.g., via a text message and/or phone call), and so forth.

In some embodiments, if the donor has not previously accessed the donor account, the telehealth platform may prompt the donor to set up the donor account. In some embodiments, the telehealth platform may prompt the donor to set up a password, a username, and/or any other account information. In some embodiments, the computer system may prompt the donor to input donor identification information. In some embodiments, the donor identification information may include one or more images of the donor, a driver's license, a passport, and/or any other identification information. In some embodiments, the computer system can prompt to donor to input information such as, for example, email, phone number, address, date of birth, gender, gender identity, prescription medications, and so forth.

In some embodiments, after the donor logs into the donor account, the computer system may request authorization from the donor. In some embodiments, the computer system may display a consent and/or data authorization agreement to the donor. In some embodiments, the computer system may require the user to provide consent and/or accept a data authorization agreement. In some embodiments, the computer system may display a notice of drug testing program or policy to the donor. In some embodiments, the computer system may display a notice of final test results documentation to the donor. In some embodiments, the notice of drug testing program or policy and/or the notice of final test results documentation may be based on a location of the donor and/or a location of the user requesting the drug screening. In some embodiments, the user may input the notice of drug testing program or policy and/or the notice of final tests results documentation into the user portal, and/or the computer system may retrieve the notice of drug testing program or policy and/or the notice of final tests results documentation from a database.

In some embodiments, at step 1108, the computer system may connect the donor with a proctor, for example via a video call. In some embodiments, at step 1110, the proctor and/or the computer system may confirm an identity of the donor. In some embodiments, the proctor and/or the computer system may prompt the donor to place a donor ID in front of a camera of the donor device. In some embodiments, the proctor may confirm the identity of the donor by comparing the donor to the donor ID. In some embodiments, the computer system may use computer vision (CV) to automatically analyze images or video of the donor and/or the donor ID captured by the camera of the donor device to confirm the identity of the donor. For example, the computer system can be configured to generate a vector representation or hash of an image of the donor in the donor ID and/or a vector representation or hash of an image captured of the donor via the camera of the donor device. In some embodiments, the computer system can store an image of a donor's ID during a sign up process, during an initial testing process, and/or the like, and the proctor and/or the computer system can compare the video of the donor to the stored ID, such that the donor does not have to show ID when taking a screening test. If the proctor and/or the computer system is unable to confirm the identity of the donor, the proctor may end the drug screening session, or the computer system may automatically end the drug screening session. In some embodiments, if the proctor and/or the computer system is unable to confirm the identity of the donor, the proctor and/or the computer system may input a notification that the identity of the donor cannot be confirmed.

In some embodiments, after the proctor and/or the computer system confirms the identity of the donor at step 1110, the proctor and/or the computer system may prompt the donor to scan an identifier (e.g., identifier 316) of the drug screening kit (e.g., screening kit 302) at step 1112. In some embodiments, the donor may capture an image of the identifier of the drug screening kit to scan the identifier. In some embodiments, the proctor and/or the computer system may compare the identifier of the drug screening kit to an identifier associated with the donor account. In some embodiments, if the identifier of the drug screening kit and the identifier associated with the donor account are not a same identifier, the proctor and/or the computer system may input a notification or indication.

In some embodiments, if the identifier of the drug screening kit and the identifier associated with the donor account are the same identifier, the proctor and/or the computer system may start administration of the drug screening at step 1114. In some embodiments, the proctor and/or the computer system may provide the donor with instructions for using the screening equipment (e.g., screening equipment 306) and/or the test panel (e.g., test panel 310) of the drug screening kit. In some embodiments, the proctor and/or the computer system may provide the donor with instructions for collecting or retrieving a sample via the sample collection device of the test panel. In some embodiments, the proctor and/or the computer system may provide the donor with instructions for inputting the sample and/or the sample collection device into the test panel.

In some embodiments, the proctor and/or the computer system may observe the donor performing steps of the administration of the drug screening to determine if the donor performs administration of the drug screening correctly and/or does not attempt to modify results of the drug screening. In some embodiments, the computer system may analyze video captured by the donor device via computer vision to determine if the donor performs administration of the drug screening correctly and/or does not attempt to modify results of the drug screening. As just one example, in some embodiments, a computer vision system can analyze images or video of a user collecting a cheek swab and can, for example, evaluate an insertion angle, insertion depth, and so forth to determine if the donor has actually swabbed their cheek or has attempted to trick the system by placing the swab in their mouth but not actually collecting a sample. In some embodiments, the proctor and/or the computer system may determine if the donor collects the sample correctly, for example, inserts a swab a proper depth into the mouth of the donor. In some embodiments, the proctor and/or the computer system may determine if the donor has modified, tampered with, or otherwise altered a tamper proof seal (e.g., tamper proof seal 308).

In some embodiments, the proctor and/or the computer system may input a notification or indication into the telehealth system if one or more errors occur. In some embodiments, the one or more errors may include incorrect collection of the sample, modification, tampering with, or otherwise altering the tamper proof seal, any of the screening equipment leaving a field of view of the camera of the donor device, the donor leaving the field of view of the camera of the donor device, and/or any other error or abnormality during the administration of the drug screening. In some embodiments, the notification or indication of one or more errors may indicate to the telehealth platform, the proctor, and/or a user to review a recording of the administration of the drug screening.

In some embodiments, computer vision systems can be used to detect abnormalities or errors. For example, a computer vision system can be configured to identify that a component of the drug screening kit has moved out of a field of view of a camera of the donor device. In some embodiments, such events can be flagged for review by a proctor, administrator (e.g., HR employee), and so forth. In some embodiments, a system may automatically end a screening session and the donor may be required to redo the test. In some embodiments, the system can flag evidence of tampering or otherwise not performing the drug screening according to the instructions. In some embodiments, a proctor, administrator, or the like can determine if the test should be invalidated, repeated, and so forth. Such an approach can offer a significant improvement in testing. For example, without computer vision, a proctor must carefully monitor a user throughout the testing process, which can limit the number of screenings a proctor can perform in a given time period. Moreover, proctors can glance away, become distracted, and so forth, which can result in the proctor missing certain errors or abnormalities. In contrast, a computer vision system can monitor testing processes without distraction experienced by humans, and proctors can review many tests and/or assist multiple users with screening at the same time, and the computer vision system can be used to flag screenings that warrant further review. In some embodiments, a telehealth platform can be configured to automatically invalidate a screening if errors or abnormalities are detected, for example if errors or abnormalities are detected with at least a threshold confidence.

In some embodiments, the computer system and/or the telehealth platform may display a proctor script to the proctor via a proctor device. In some embodiments, the proctor script may include one or more instructions or prompts for the proctor to provide to the donor, one or more reminders for the proctor of a tone to use when providing instructions or prompts to the donor, instruction for how to handle one or more donor reactions throughout administration of the drug screening, and/or any other information for the proctor.

In some embodiments, after the donor administers the drug screening at step 1114, the proctor and/or the computer system may analyze results of the drug screening at step 1116. In some embodiments, the proctor and/or the computer system may prompt the user to position the test panel in the field of view of the camera of the donor device.

In some embodiments, as described above with reference to FIG. 3B, the one or more result indicators of the test panel may include anonymized result indicators so the donor may not be able to determine which drug each of the one or more result indicators corresponds to. In some embodiments, the proctor device may display to the proctor which drug each of the one or more result indicators corresponds to. In some embodiments, the computer system may display text or graphics to indicate to the proctor which drug each of the one or more result indicators corresponds to. In some embodiments, the computer system may display one or more graphics overlayed on one or more images or video captured by the camera of the donor device.

In some embodiments, the proctor may analyze the one or more images or video captured by the camera of the donor device to determine a result of the drug screening indicated by one or more of the one or more result indicators. In some embodiments, the computer system may use computer vision (CV) to automatically analyze the one or more images or video captured by the camera of the donor device. In some embodiments, the computer system may use CV to automatically determine the result of the drug screening indicated by one or more of the one or more result indicators. In some embodiments, both the proctor and the computer system may analyze the one or more images or video captured by the camera of the donor device to determine the result of the drug screening indicated by one or more of the one or more result indicators 14.

In some embodiments, if none of the one or more result indicators indicate detection of one or more drugs or all of the one or more result indicators indicate an absence of one or more drugs the proctor and/or the computer system may end the screening session at step 1124. The results can be stored in a database. In some embodiments, if the one or more result indicators do not indicate detection of one or more drugs and/or the one or more result indicators indicate an absence of one or more drugs the proctor and/or the computer system may end the screening session at step 1124. The results can be stored in the database In some embodiments, if one or more result indicators indicate detection of one or more drugs, the proctor and/or the computer system may determine that the indication is a presumptive positive or the indication should be confirmed by a laboratory. In some embodiments, if one or more result indicators indicate detection of one or more drugs, the proctor and/or the computer system may indicate to the donor that the test panel and/or one or more result indicators indicated a non-negative result. In some embodiments, the proctor and/or the computer system may instruct the donor to place the test panel and/or any other of the screening equipment in the return packaging at step 1118. In some embodiments, the proctor and/or the computer system may observe the donor placing the test panel and/or any other of the screening equipment in the return packaging. In some embodiments, the proctor and/or the computer system may determine if the donor attempts to modify, tamper with, or otherwise alter the test panel, any other of the screening equipment, and/or the return packaging. In some embodiments, if the proctor and/or the computer system determine that the donor attempts to modify, tamper with, or otherwise alter the test panel, any other of the screening equipment, and/or the return packaging, the proctor and/or the computer system may input a notification and/or an indication of the same.

In some embodiments, the proctor and/or the computer system may prompt the donor to scan the identifier of the drug screening kit and/or the return packaging to confirm the drug screening kit and/or the return packaging are a correct drug screening kit and/or the return packaging. In some embodiments, the proctor and/or the computer system may prompt the donor to scan the identifier of the drug screening kit to confirm the drug screening kit the donor placed in the return packaging is a same drug screening kit the donor used for the drug screening. In some embodiments, the proctor and/or the computer system may prompt the donor to scan the identifier of the return packaging to confirm the return packaging is the return packaging associated with the drug screening kit and/or the screening equipment.

In some embodiments, the proctor and/or the computer system may prompt or instruct the donor to ship, transmit, or otherwise send the return packaging to a laboratory. In some embodiments, the proctor and/or the computer system may prompt the donor to capture one or more images or videos of the return packaging after the user places the test panel and/or any other of the screening equipment in the return packaging. In some embodiments, the proctor and/or the computer system may prompt the donor to capture one or more images or videos of the return packaging before the user ships, transmits, or otherwise sends the return packaging to the laboratory. In some embodiments, the proctor and/or the computer system may prompt or instruct the donor to take the return packaging to a delivery service, for example, FEDEX, UPS, USPS, etc.

In some embodiments, a courier may retrieve or pick up the return packaging from the donor. In some embodiments, the computer system may prompt the courier to capture one or more images or videos of the return packaging. In some embodiments, the courier may take the return packaging to the delivery service.

In some embodiments, at step 1120, the delivery service and/or the computer system may assign a tracking number to the return packaging. In some embodiments, the computer system may automatically retrieve the tracking number and/or other delivery information for the return packaging from the delivery service. In some embodiments, the computer system may automatically retrieve the tracking number and/or delivery information via an API. In some embodiments, the computer system may use the tracking number and/or delivery information for chain of custody as described further below with reference to FIGS. 12A and 12B.

In some embodiments, the laboratory may receive the return packaging. In some embodiments, if the return packaging is modified, tampered with, or otherwise altered when the laboratory receives the return packaging, the laboratory may input a notification and/or indication of the same.

In some embodiments, the laboratory may perform confirmatory testing on the sample retrieved by the sample collection device at step 1122. In some embodiments, the laboratory may perform oral fluid testing and/or urine testing. In some embodiments, the laboratory may perform confirmatory testing on a second sample retrieved by a second sample collection device. In some embodiments, the donor may retrieve the second sample during the drug screening session, before the drug screening session, and/or after the drug screening session. In some embodiments, the laboratory may perform a DNA analysis on both the sample and the second sample to confirm the sample and the second sample are both from a same donor.

In some embodiments, if the laboratory confirms the presumptive positive of the drug screening, the laboratory and/or the computer system may determine the result of the drug screening is a confirmed positive result. In some embodiments, the computer system may automatically transmit the positive results or indication that the donor tested positive for one or more drugs to the user portal. The results can be stored in a database at step 1124.

In some embodiments, a medical review officer (MRO) and/or other laboratory personnel may interpret the result of the drug screening. In some embodiments, the MRO and/or the other laboratory personnel may review the result of the drug screening indicated by one or more of the one or more result indicators and/or a result of the confirmatory testing. In some embodiments, the MRO and/or the other laboratory personnel may input the confirmed positive result into the computer system. In some embodiments, the MRO and/or the other laboratory personnel may review donor information to determine if the donor information indicates a reason for the positive result of the drug screening, for example, the donor may have a prescription. In some embodiments, if the donor information indicates a reason for the positive result, the MRO and/or the other laboratory personnel may determine that the positive result of the drug screening is not confirmed, and the results of the drug screening are negative. In some embodiments, may input the negative result into the computer system and the results can be stored in the database at step 1124.

In some embodiments, any records or the chain of custody of the drug screening session may include a name, address, phone number, and/or any other information about the MRO and/or the other laboratory personnel. In some embodiments, the user portal may display to a user the name, address, phone number, and/or any other information about the MRO and/or the other laboratory personnel.

In some embodiments, the computer system may transmit any of the notifications and/or the indications input by the proctor, the laboratory, and/or the computer system at any of the steps of method 1100 to the user portal. In some embodiments, a user may review images, videos, and/or any other information about the drug screening session based on the notifications and/or the indications.

In some embodiments, the computer system may transmit any results of the drug screening session and/or the confirmatory testing to a user and/or the donor via an email, a text message, a call, and/or any other form of communication. In some embodiments, the results may include a file format. In some embodiments, the file format may include .csv, .txt, .doc, .docx, .xls, .xlsx, .pdf, and/or any other file format.

In some embodiments, the computer system may automatically update the chain of custody and/or a digital audit trail throughout any of the steps of method 1100. In some embodiments, the chain of custody and/or the digital audit trail may be displayed to the user via the user portal.

Chain of Custody

As discussed briefly above, it can be important to maintain records and ensure proper chain of custody is maintained when performing drug screenings. For example, drug screening test results can be used in making pre-employment decisions, employment decisions, and so forth. In some cases, drug screening results can play a part in determining liability, such as when a worker is involved in an accident while on the job. For example, if a worker is under the influence of one or more drugs while working and gets injured, and the worker seeks to recover damages from their employer, the worker's recovery may be reduced or even barred. As another example, if a worker injures others while on the job, the employer's liability may depend upon whether or not the worker was under the influence of one or more drugs at the time of the incident, whether the employer had a drug testing policy in place, whether the policy was adequate, whether the policy was followed, and so forth.

It can be important for employees or other organizations that perform testing to have a defensible record of the drug screening. For example, if an employee is fired or an individual's parole is revoked as a result of a failed drug screening, it can be important that the employer or government authorities be able to show that the drug screening was conducted properly and without abnormalities.

Accordingly, in some embodiments, chain of custody information, video information, and so forth can be stored for future use. As described herein, in some embodiments, video and/or other data can be automatically retained for a period of time. In some embodiments, video and/or other data can be removed automatically after a period of time, for example to reduce an amount of storage capacity needed to store information about past drug screening sessions, to reduce the amount of information stored so that less information is potentially at risk of being obtained by unauthorized users, and so forth. In some embodiments, a user can use a user portal, as shown in FIG. 7, to mark a result for preservation. For example, if legal action has arisen or has a likelihood of arising and the drug screening result can be relevant (e.g., to determine liability), any related video, chain of custody information, or other information related to the testing session can be maintained, in some cases even if such information would ordinarily be removed according to standard data retention policies.

Figure 12B:
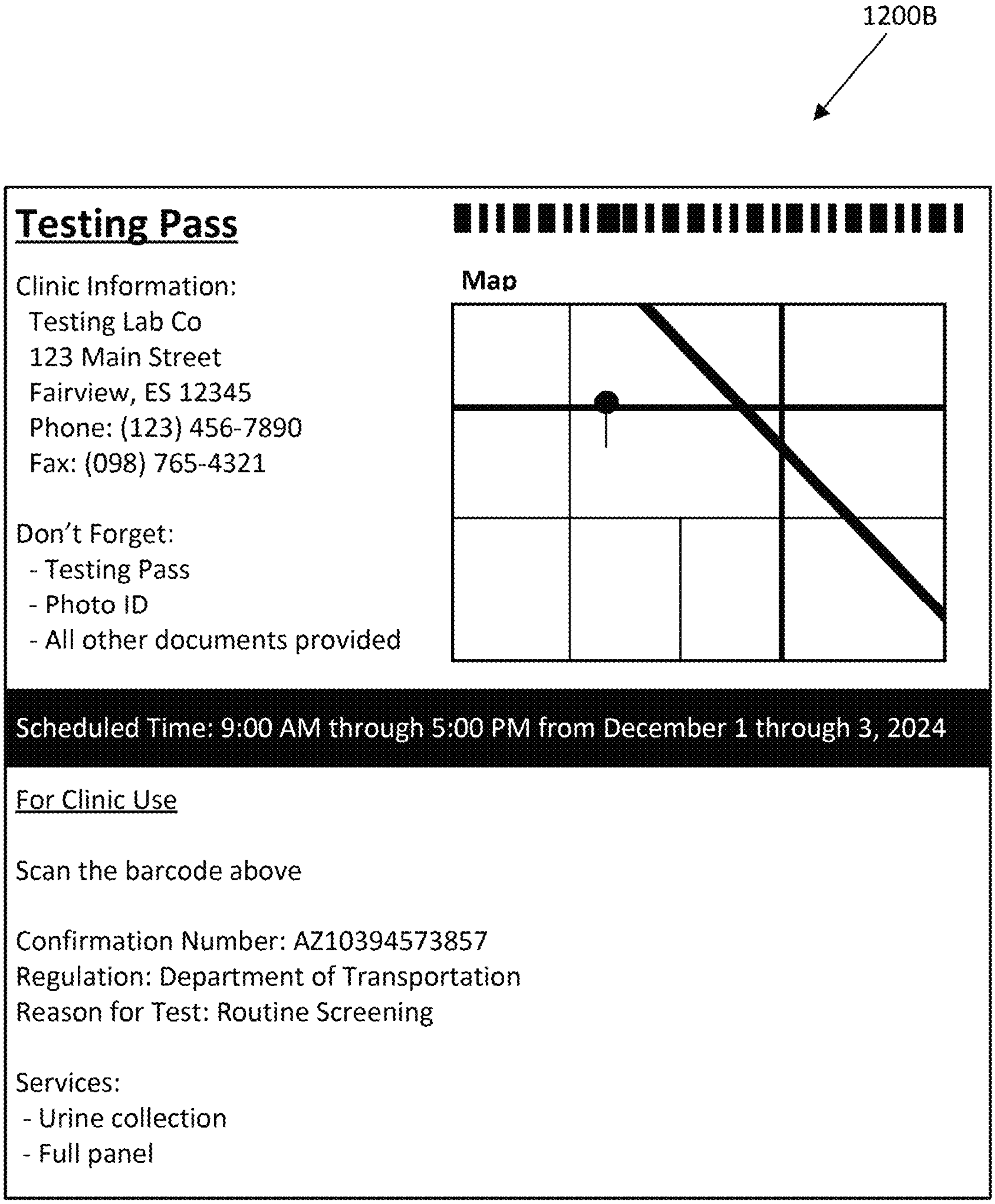

Once data collection processes described herein (or other processes) are completed, a telehealth provider can provider test results to a user, donor, etc. In some embodiments, a testing or screening kit, or a portion thereof, can be returned to a lab or other facility (e.g., using the return packaging 318 of FIG. 3A) to conduct further testing or processing. in some embodiments, the computer system can determine a chain of custody for a screening kit, a telehealth session, etc. In some embodiments, the chain of custody may include a chain of custody form, which can include a chain of custody and control form (e.g., digital or physical chain of custody control form). FIGS. 12A and 12B show example chain of custody forms. Other chain of custody forms can be used to capture the same or similar information.

In some embodiments, the chain of custody form may be transmitted to the laboratory. In some embodiments, the custody form may be shipped to the laboratory or transmitted digitally to the laboratory. In some embodiments, the laboratory may review the chain of custody form to confirm the return packaging received by the laboratory corresponds to a correct donor and/or a sample included in the return packaging received by the laboratory corresponds to the correct donor.

In some embodiments, the chain of custody form may be transmitted to the user portal or otherwise made available in the user portal. In some embodiments, a user may review the chain of custody form to confirm the return packaging received by the laboratory corresponds to the correct donor and/or the sample included in the return packaging received by the laboratory corresponds to the correct donor. In some embodiments, the user may review the custody form to confirm the sample used during the drug screening and the sample used for the confirmatory testing are both samples from the same donor.

In some embodiments, the chain of custody form may include a chain of custody tracker. In some embodiments, the chain of custody tracker may include an identifier (e.g., identifier 316) and/or a second identifier associated with the identifier. In some embodiments, the chain of custody tracker may be used to confirm the kit, the testing equipment, the test panel, the sample, and/or other components are correct and/or the same.

In some embodiments, the chain of custody form may include the donor information, a test method, a confirmatory test method, a test panel and/or testing equipment make or model, billing information, reporting information, MRO and/or other laboratory personnel information, proctor information, results of the confirmatory testing, a reason for the drug screening, for example pre-employment, random, reasonable suspicion, etc., and/or any other chain of custody information about the telehealth session or the telehealth kit.

In some embodiments, the chain of custody form and/or the user portal may include one or more time stamps. In some embodiments, the one or more time stamps may include a time when the identifier is scanned, a time when the telehealth session started, a time when the donor was connected to the proctor via a video call, a time when the return packaging was picked up by a courier, a time when the return packaging was received by the delivery service, a time when the laboratory received the return packaging, a time when the confirmatory testing was performed, any other time, or any combination.

In some embodiments, the computer system may transmit and/or receive chain of custody information and/or any other information from the laboratory via an API, an HL7 file, a JSON file, and/or any other digital communication protocol or pathway. In some embodiments, the chain of custody information and/or any other information included on the chain of custody form may be based on a location of the user, the location of the donor, the location of the laboratory, the location of the requesting entity, and/or the location of any other party.

In some embodiments, the computer system may store the chain of custody information, videos of the telehealth session, images of the telehealth session, the results of the telehealth session, the results of the confirmatory testing, and/or any other information for a period of time. In some embodiments, the period of time may include a time of 1 day or about 1 day, 1 week or about 1 week, 1 month or about 1 month, 2 months or about 2 months, 3 months or about 3 months, 4 months or about 4 months, 5 months or about 5 months, 6 months or about 6 months, 7 months or about 7 months, 8 months or about 8 months, 9 months or about 9 months, 10 months or about 10 months, 11 months or about 11 months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any value between the aforementioned values, or more.

In some embodiments, the computer system and/or the user portal may transmit a system report to the user. In some embodiments, the computer system and/or the user portal may transmit the system report to the user upon request by the user. In some embodiments, the computer system and/or the user portal may transmit the system report to the user periodically. In some embodiments, the computer system and/or the user portal may transmit the system report to the user with a frequency of or about every 1 day or about 1 day, 2 days or about 2 days, 3 days or about 3 days, 4 days or about 4 days, 5 days or about 5 days, 6 days or about 6 days, 1 week or about 1 week, 2 weeks or about 2 weeks, 3 weeks or about 3 weeks, 1 month or about 1 month, 2 months or about 2 months, 3 months or about 3 months, 4 months or about 4 months, 5 months or about 5 months, 6 months or about 6 months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any value between the aforementioned values. In some embodiments, the system report may include any chain of custody information, videos of telehealth sessions, images of telehealth sessions, results of the telehealth sessions, results of confirmatory tests, and/or any other information about any completed telehealth sessions over a period of time. In some embodiments, the system report may include a number of tests conducted, a number of positive test results, a number of negative test results, what drugs or substances donors tested positive for, how many screenings of each type of drug screening, and/or any other information.

In some embodiments, some or all data related to drug screening can be stored in an immutable form. For example, in some embodiments, drug screening information (e.g., results, chain of custody, video, etc.) can be maintained in a blockchain or other immutable database. Such an approach can help ensure that information is not tampered with after it is collected. In some cases, only drug screening information that is marked for retention may be stored in an immutable form. This can have several advantages, as storing all screening data in such a form may consume a prohibitively large amount of storage and may otherwise be unwieldy to work with. However, such an approach can have several drawbacks, as an actor would be able to modify data prior to preserving the record. In some embodiments, relatively large data such as video and/or any other data can be stored on the blockchain or in another immutable form. In some embodiments, drug screening data can be preserved by, for example, calculating a checksum for one or more video files and/or any other data associated with a drug screening. In such an approach, rather than storing the relatively large videos and/or any other data on the blockchain or other immutable data store, the checksum can be stored. If there is a later need to view a video or retrieve other data, the video's checksum and/or the other data's checksum can be recalculated and compared to the checksum stored on the blockchain to ensure that the video and/or any other data has not been altered. Similar approaches can be used for other data, such as test results, chain of custody forms, etc., enabling assurance that video and/or other records have not been modified without the need to maintain all data in an immutable form.

Other approaches can be used alternatively or in addition to the approach described above. For example, in some embodiments, chain of custody, drug screening results, and so forth can be digitally signed. If such digitally signed records are later tampered with, it can be readily determined that the records are not authentic.

Drug screening information can be stored in a variety of formats that achieve many of the same goals as storing such information in a blockchain or immutable database. For example, in some embodiments, drug screening information can be stored in a conventional database with a slowly changing dimension (e.g., a database with columns that indicate whether a record is active or inactive, or columns that indicate a time range during which a record is active). In some embodiments, a database table can be configured for versioning and the SQL "as of" syntax can be used to retrieve records as of a particular date. However, such approaches can still be susceptible to tampering. In some embodiments, a ledger database can be used. The ledger database can operate similarly to a blockchain. However, unlike a blockchain, consensus may not be required. Rather, a single trusted entity can maintain control of the ledger. Other technologies can also be used, such as decentralized version-controlled databases.

In the case of a telehealth service that offers drug testing services to organizations, the telehealth service itself may maintain the immutable record. For example, the telehealth service can maintain a ledger database and can be the trusted entity for maintaining the ledger. Accordingly, any tampering with the drug testing records by a laboratory, employer, and so forth could be readily detected, providing an element of trust for the records.

As described above, the computer system may determine a chain of custody for each drug screening kit and/or drug screening session. In some embodiments, the chain of custody may include a chain of custody form. As shown in FIG. 12A, the chain of custody form 1200A may include a paper chain of custody and control form. As shown in FIG. 12B, the chain of custody form may include a digital chain of custody form 1200B.

In some embodiments, the chain of custody form may be transmitted to the laboratory. In some embodiments, the custody form may be shipped to the laboratory or transmitted digitally to the laboratory. In some embodiments, the laboratory may review the chain of custody form to confirm the return packaging received by the laboratory corresponds to a correct donor and/or a sample included in the return packaging received by the laboratory corresponds to the correct donor.

In some embodiments, the chain of custody form may be transmitted to the user portal. In some embodiments, a user may review the chain of custody form to confirm the return packaging received by the laboratory correspond to the correct donor and/or the sample included in the return packaging received by the laboratory corresponds to the correct donor. In some embodiments, the user may review the custody form to confirm the sample used during the drug screening and/or the sample used for the confirmatory testing are both samples from the same donor.

In some embodiments, the chain of custody form may include a chain of custody tracker. In some embodiments, the chain of custody tracker may include the identifier and/or a second identifier associated with the identifier. In some embodiments, the chain of custody tracker may be used to confirm the drug screening kit, the screening equipment, the test panel, the sample, and/or the second sample used at each step of a drug screening process are correct and/or the same.

In some embodiments, the chain of custody form may include the donor information, a test method, a confirmatory test method, a test panel and/or screening equipment make or model, billing information, reporting information, MRO and/or other laboratory personnel information, proctor information, results of the confirmatory testing, a reason for the drug screening, for example pre-employment, random, reasonable suspicion, etc., and/or any other chain of custody information about the drug screening process or the drug screening kit.

In some embodiments, the chain of custody form and/or the user portal may include one or more time stamps. In some embodiments, the one or more time stamps may include a time when the identifier is scanned each time throughout a screening and/or confirmatory testing process, a time when the drug screening session started, a time when the donor was connected to the proctor via a video call, a time when the return packaging was picked up by a courier, a time when the return packaging was received by the delivery service, a time when the laboratory received the return packaging, a time when the confirmatory testing was performed and/or any other time.

In some embodiments, the computer system may transmit and/or receive chain of custody information and/or any other information from the laboratory via an API, an HL7 file a JSON file, and/or any other digital communication protocol or pathway.

In some embodiments, the chain of custody information and/or any other information included on the chain of custody form may be based on a location of the user, the location of the donor, the location of the laboratory, the location of the requesting entity, and/or the location of any other party.

In some embodiments, the computer system may store the chain of custody information, videos of the drug screening session, images of the drug screening session, the results of the drug screening session, the results of the confirmatory testing, and/or any other information for a period of time. In some embodiments, the period of time may include a time of 1 day or about 1 day, 1 week or about 1 week, 1 month or about 1 month, 2 months or about 2 months, 3 months or about 3 months, 4 months or about 4 months, 5 months or about 5 months, 6 months or about 6 months, 7 months or about 7 months, 8 months or about 8 months, 9 months or about 9 months, 10 months or about 10 months, 11 months or about 11 months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any value between the aforementioned values.

In some embodiments, the computer system and/or the user portal may transmit a system report to the user. In some embodiments, the computer system and/or the user portal may transmit the system report to the user upon request by the user. In some embodiments, the computer system and/or the user portal may transmit the system report to the user periodically. In some embodiments, the computer system and/or the user portal may transmit the system report to the user every 1 day or about 1 day, 1 week or about 1 week, 1 month or about 1 month, 2 months or about 2 months, 3 months or about 3 months, 4 months or about 4 months, 5 months or about 5 months, 6 months or about 6 months, 7 months or about 7 months, 8 months or about 8 months, 9 months or about 9 months, 10 months or about 10 months, 11 months or about 11 months, 1 year or about 1 year, 2 years or about 2 years, 3 years or about 3 years, 4 years or about 4 years, 5 years or about 5 years, 6 years or about 6 years, 7 years or about 7 years, 8 years or about 8 years, 9 years or about 9 years, 10 years or about 10 years, and/or any value between the aforementioned values. In some embodiments, the system report may include any chain of custody information, videos of drug screening sessions, images of drug screening sessions, results of the drug screening sessions, results of confirmatory tests, and/or any other information about any completed drug screening session over a period of time. In some embodiments, the system report may include a number of tests conducted, a number of positive test results, a number of negative test results, what drugs or substances donors tested positive for, how many screenings of each type of drug screening, and/or any other information.

Drug Screening Provider

Figure 13:
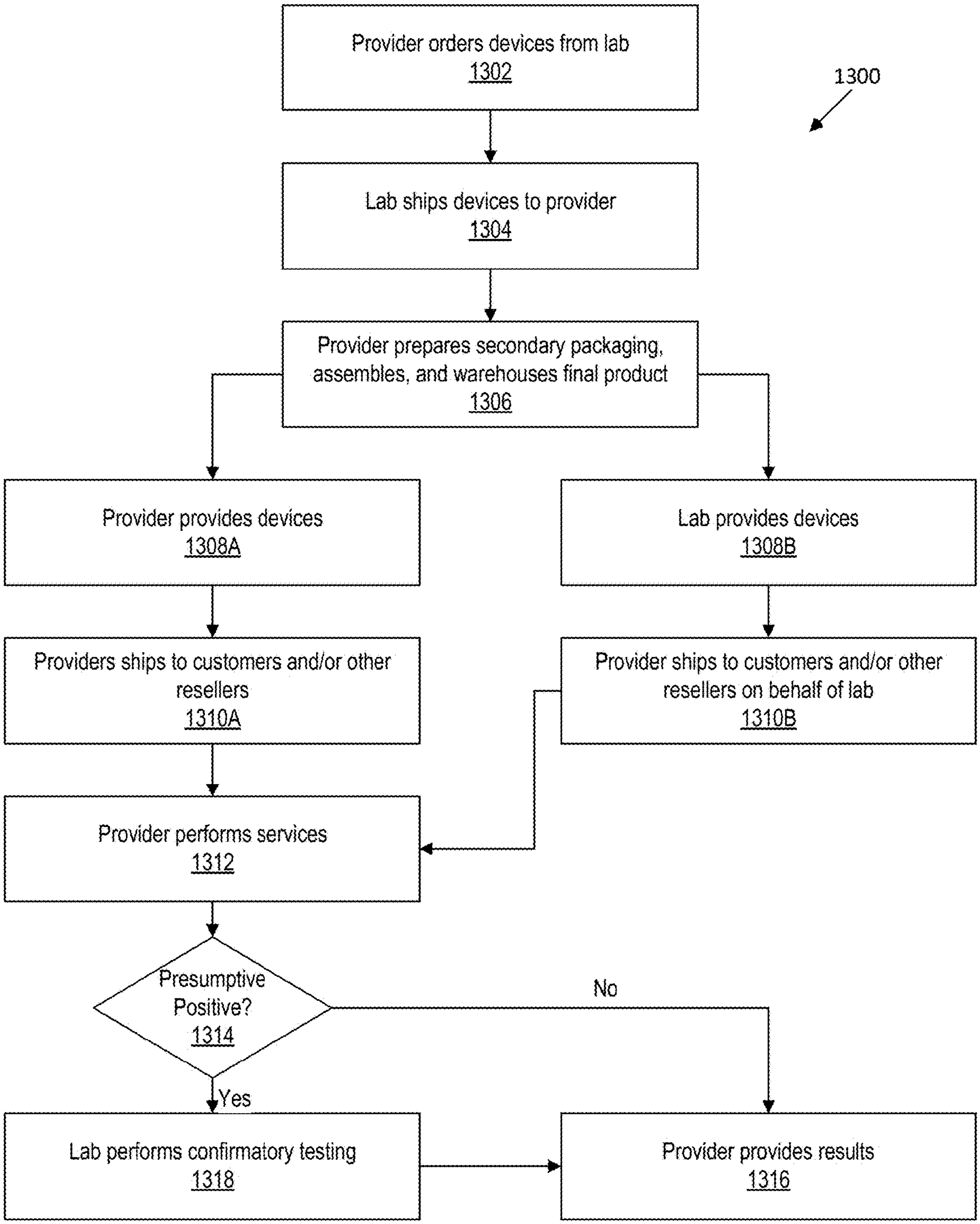
FIG. 13 shows a schematic of an example method for a drug screening workflow.

FIG. 13 shows a schematic of a method 1300 for a drug screening workflow. In some embodiments, at step 1302 a drug screening provider may order a plurality of screening equipment from a laboratory or equipment provider. In some embodiments, at step 1304 the drug screening provider may receive the plurality of screening equipment from the provider. In some embodiments, at step 1306, the drug screening provider may package and/or assemble the screening equipment in drug screening kits. In some embodiments, the drug screening provider may generate identifiers (e.g., unique identifiers), return packaging and/or any other items included in or on the drug screening kits.

In some embodiments, at step 1308A, the provider can provide drug screening kits to users. Alternatively or additionally, at step 1308B, a lab can provide drug screening kits to users. In some embodiments, the provider and/or lab can provide drug screening kits to users, donors, requesting entities, and/or others. In some embodiments, at step 1310A, the drug screening provider can ship or send the drug screening kits directly to users, requesting entities, and/or donors. In some embodiments, alternatively or additionally, at step 1310B, the provider can ship drug screening kits to users, requesting entities, and/or donors on behalf of the lab.

In some embodiments, at step 1312, the drug screening provider may perform drug screening services. At step 1314, the drug screening provider can determine if the donor has a presumptive positive result. If not, the drug screening provider can provide the drug screening results to the user, the user portal, the donor, the requesting entity, and/or any other entity at step 1316. If there is a presumptive positive, the donor can be instructed to send a sample for confirmatory testing, and the lab can perform confirmatory testing at step 1318. At step 1316, the drug screening provider may provide the drug screening results and/or the results of the confirmatory testing to the user, the user portal, the donor, the requesting entity, and/or any other entity.

Equipment Operation Restriction

As described herein, it can be important to restrict access to vehicles, heavy machinery, and other potentially dangerous equipment. For example, it can be important to prevent individuals who are under the influence of drugs of alcohol from operating such equipment, which can lead to accidents, injuries, and so forth. Companies, government entities, and so forth may struggle to adequately monitor individuals. For example, individuals may not be at a centralized location (e.g., truck drivers), providing human supervision can be error-prone and expensive, and so forth.

In some embodiments, the approaches described herein can be used to restrict access to certain equipment such as vehicles, heavy machinery, and so forth. For example, individuals can be required to pass a drug and/or alcohol screening before being able to operate equipment. As used herein, the term "vehicle" can refer to an automobile, forklift, construction equipment, manufacturing equipment, and/or any other machinery to which access can be restricted.

Figure 14A:
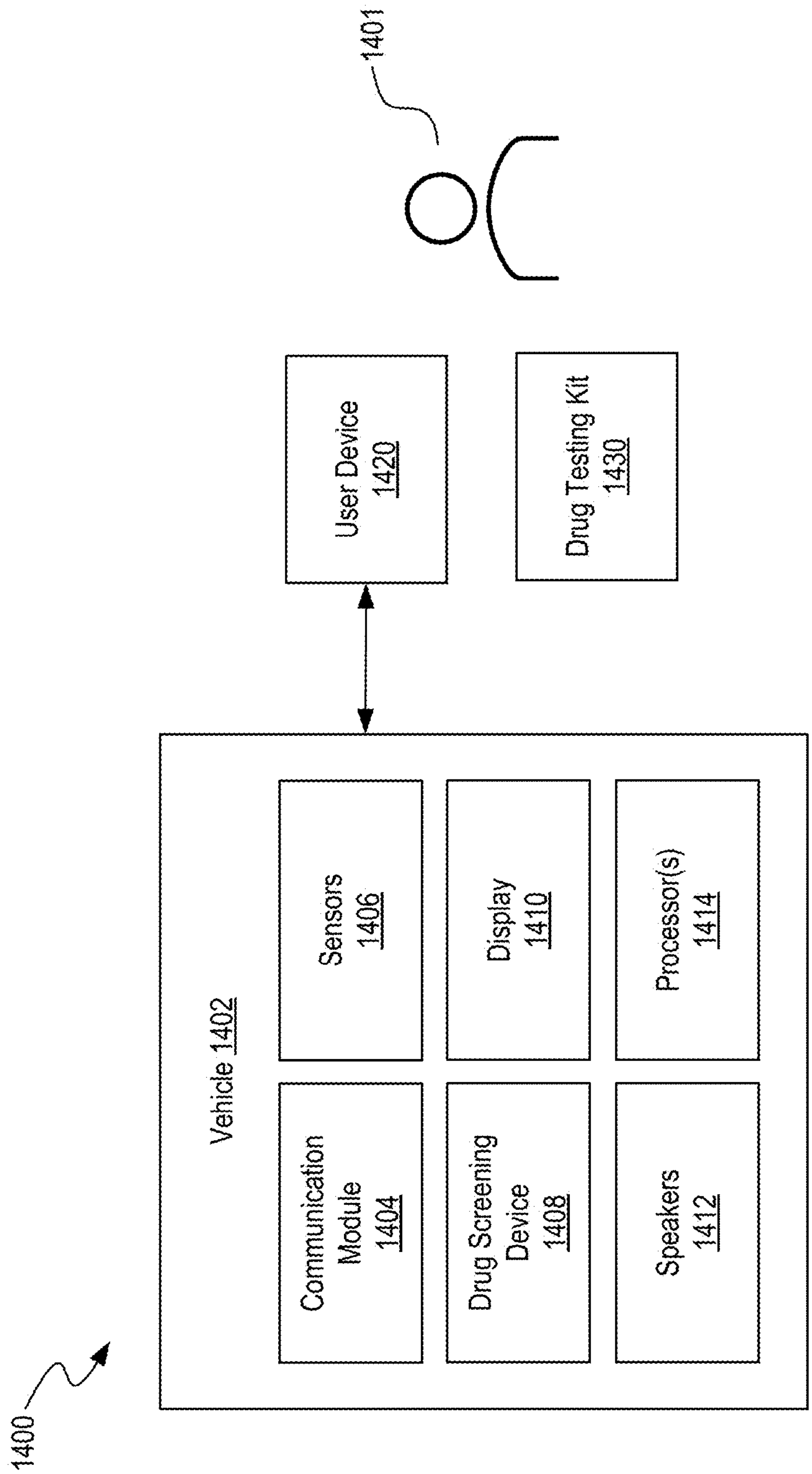
FIG. 14A is a schematic diagram illustrating an in-vehicle drug screening system according to some embodiments.

FIG. 14A is a schematic diagram illustrating an in-vehicle drug screening system 1400. In some embodiments, the system 1400 can include a vehicle 1402. In some embodiments, the vehicle 1402 can include a car, a van, a pick-up truck, an electric car, a gasoline-powered car, a semi-truck, an autonomous vehicle, a train, a motorcycle, a personal flying aircraft, a commercial aircraft, a jetliner, a crane, a forklift, a tractor, a combine, a dump truck, an excavator, a boat, a jet ski, watercraft, and/or any other vehicle, construction equipment, industrial equipment, or dangerous machinery.

In some embodiments, the system 1400 can include a communication module 1404, sensors 1406, drug screening device 1408, display 1410, speakers 1412, and/or processors 1414. In some embodiments, the aforementioned components can be included in and/or operably coupled to the vehicle 1402. In some embodiments, a drug testing kit 1430 can be provided separately. In some embodiments, the communication module 1404 can include Wi-Fi, Bluetooth, Bluetooth® Low Energy, a cellular connection, ultra-wideband (UWB), RFID, NFC, wireless local area network (WLAN), and/or any other wireless communication protocol. In some embodiments, the communication module 1404 can be configured to communicate with a user device 1420. In some embodiments, the user device 1420 can include a key, a key fob, a mobile phone, a personal computer, and/or any other device configured to wirelessly communicate with other devices.

In some embodiments, the communication module 1404 can be configured to communicate with the user device to determine when a user 1401 is near the vehicle 1402. In some embodiments, the communication module 1404 can be configured to communicate with the user device 1420 to determine when the user 1401 unlocks the vehicle 1402. In some embodiments, the communication module 1404 can be configured to communicate with the user device 1420 to determine when the user 1401 turns the vehicle 1402 on. In some embodiments, the communication module 1404 can be configured to communicate with the user device 1420 to determine when the user 1401 opens a door of the vehicle 1402. In some embodiments, the communication module 1404 can be configured to determine when the user 1401 enters the vehicle 1402.

In some embodiments, the communication module 1404 can be configured to connect the vehicle 1402 and/or the user 1401 to a proctor device. In some embodiments, the communication module 1404 can be configured to transmit results of the drug screening to a third-party driving service, to transmit a notification to an employer, and so forth. In some embodiments, the communication module 1404 can be configured to transmit a GPS location of the user device to the third-party driving service. In some embodiments, the communication module 1404 can be configured to automatically request a ride from the third-party driving service.

In some embodiments, the communication module 1404 can be configured to transmit an electronic message to a third-party person, for example, the user's emergency contact, the user's spouse, the user's sponsor, the user's guardian, etc. In some embodiments, the electronic message can include information about the results of the drug screening. In some embodiments, the information about the results of the drug screening can include that the user 1401 failed the drug screening, a concentration of one or more drugs, such as a blood alcohol level, a location of the vehicle 1402, a location of the user device 1420, a time when the user 1401 failed the drug screening, whether a ride has been requested with the third-party driving service, any other information about the results of the drug screening, or any combination thereof. In some embodiments, the communication module 1404 can be configured to transmit a geolocation of the vehicle 1402 to the user device and/or the third-party person, for example as determined using a GPS receiver.

In some embodiments, the sensors 1406 can include a touch sensor, a proximity sensor, a temperature sensor, a motion sensor, a contact sensor, and/or any other sensor. In some embodiments, the sensors 1406 can be positioned on a door of the vehicle 1402. In some embodiments, the sensors 1406 can be positioned on a handle of the door of the vehicle 1402. In some embodiments, the sensors 1406 can be positioned on a door panel of the door of the vehicle 1402. In some embodiments, the sensors 1406 can be positioned on a dashboard of the vehicle 1402. In some embodiments, the sensors 1406 can be positioned on a steering wheel of the vehicle 1402. In some embodiments, the sensors 1406 can be positioned on a center console of the vehicle 1402. In some embodiments, the sensors 1406 can be positioned on a control panel of the vehicle 1402. In some embodiments, the sensors 1406 can be positioned at an ignition system of the vehicle 1402. In some embodiments, the sensors 1406 can be located in one or more keys and/or key fobs. In some embodiments, the sensors 1406 can be positioned in the interior of the vehicle 1402. In some embodiments, the sensors 1406 can be positioned on the exterior of the vehicle 1402.

In some embodiments, the one or more sensors 1406 can be configured to determine when the user 1401 enters the vehicle 1402. In some embodiments, the sensors 1406 can be configured to determine when the user 1401 is near the vehicle 1402. In some embodiments, the sensors 1406 can be configured to determine when the user 1401 opens the door of the vehicle 1402. In some embodiments, the sensors 1406 can be configured to determine when the user 1401 enters the vehicle 1402. In some embodiments, the sensors 1406 can be configured to determine when the user 1401 turns the vehicle 1402 on or otherwise interacts with the vehicle.

In some embodiments, the communication module 1404 and/or the sensors 1406 can be configured to initiate a proctored drug screening session. For example, in some embodiments, the communication module 1404 and/or the sensors 1406 can initiate the proctored drug screening session when the user 1401 is near the vehicle 1402, when the user unlocks the vehicle 1402, when the user opens the door of the vehicle 1402, when the user enters the vehicle 1402, when the user 1401 turns on the vehicle 1402, and/or before or after the aforementioned times, or based on other triggers, such as activating a switch or otherwise interacting with the vehicle In some embodiments, the sensors 1406 can include biometric sensors such as a fingerprint scanner, a palm scanner, an iris scanner, a voice analyzer, and/or any other biometric sensor. In some embodiments, the biometric sensors can be located on a dashboard of the vehicle 1402, the door of the vehicle 1402 (e.g., on a handle of a door), a steering wheel of the vehicle 1402, a steering column of the vehicle, a center console of the vehicle 1402, a control panel of the vehicle 1402, a rearview mirror of the vehicle 1402, a windshield of the vehicle 1402, a seat of the vehicle 1402, a door handle of the vehicle 1402, an ignition system of the vehicle 1402, and/or any other location of the interior of the vehicle 1402.

The one or more drug screening devices 1408 can be examples of the kit 302 (FIG. 3A). In some embodiments, the one or more drug screening devices 1408 can be a part of the vehicle 1402 and integrated into the vehicle 1402 In some embodiments, the one or more drug screening devices 1408 can be configured to determine a presence of a drug in a sample provided by the user 1401. In some embodiments, the one or more drug screening devices 1408 can be configured to determine a concentration of the drug in the user. In some embodiments, the one or more drug screening devices 1408 can be configured to determine a concentration of the drug in the blood of the user. In some embodiments, the drug can include alcohol, marijuana, prescription drugs, narcotics, and/or any other drugs.

In some embodiments, the one or more drug screening devices 1408 can receive a sample from the user 1401. In some embodiments, the sample can include saliva, urine, sweat, blood, and/or any other body fluid. In some embodiments, the sample can include a hair sample, and/or cells from the nasopharynx of the user 1401. In some embodiments, the one or more drug screening devices 1408 can include a breathalyzer. In some embodiments, the one or more drug screening devices 1408 can determine the presence of the drug in the sample provided by the user 1401, the concentration of the drug in the user, and/or the concentration of the drug in the blood of the user 1401. In some embodiments, the drug screening device can screen for 1 drug, 2 drugs, 3 drugs, 4 drugs, 5 drugs, 6 drugs, 7 drugs, 8 drugs, 9 drugs, 10 drugs, 11 drugs, 12 drugs, 29 drugs, 14 drugs, 15 drugs, 20 drugs, 25 drugs, 30 drugs, 35 drugs, 40 drugs, 45 drugs, 50 drugs, and/or any value between the aforementioned values.

In some embodiments, the drug screening device 1408 can include a kit having a stand. In some embodiments, the stand can be configured to receive and/or hold the user device 1420, for example, a mobile phone, a tablet, or the like. In some embodiments, the stand can hold the user device 1420 while the user is performing one or more steps of a drug screening. In some embodiments, the stand can allow the user to perform the drug screening without holding the user device 1420. In some embodiments, the stand can be positioned on or coupled to the dashboard of the vehicle 1402, the door of the vehicle 1402, the steering wheel of the vehicle 1402, the steering column of the vehicle, the center console of the vehicle 1402, the control panel of the vehicle 1402, the headrest of a seat of the vehicle 1402, the rearview mirror of the vehicle 1402, the windshield of the vehicle 1402, and/or any other location of the interior of the vehicle 1402. In some embodiments, the stand can be positioned on or coupled to the exterior of the vehicle 1402.

In some embodiments, the stand can include a portion of the kit (e.g., a container of the kit). In some embodiments, the stand may be coupled to the container. In some embodiments, the container may include one or more features, indentations, and/or extrusions that form the stand. In some embodiments, the container may be folded, bent, or otherwise modified to form the stand.

In some embodiments, the user device 1420 can be configured to connect the user with a proctor for the proctored drug screening session via audio and/or video communication. In some embodiments, the proctor can monitor and/or the system 1400 can monitor the user during the proctored drug screening session via image data and/or audio data captured by the user device 1420. In some embodiments, the image data can be captured by a camera of the user device 1420. In some embodiments, the audio data can be captured by a microphone of the user device 1420.

In some embodiments, the proctor and/or the system 1400 can instruct the user to perform one or more steps of the drug screening via the audio and/or video communication. In some embodiments, the proctor and/or the system 1400 can transmit electronic messages and/or data that enable a display of the user device 1420 to output images and/or video to the user. In some embodiments, the proctor can transmit data that enables speakers of the user device 1420 to output audio to the user. In some embodiments, the proctor can transmit results of the drug screening to the user device 1420. In some embodiments, any and/or all of these steps may not be performed by a proctor but may instead be performed by a telehealth platform. For example, a telehealth platform can be configured to automatically proceed through a testing procedure and video, images, and/or audio can be captured. In some embodiments, the telehealth platform can be configured to detect abnormalities and can flag the abnormalities for review as described herein.

In some embodiments, the user device 1420 can communicate with the vehicle 1402 via a wired and/or wireless connection. In some embodiments, the user device 1420 can communicate with the vehicle 1402 via Wi-Fi, Bluetooth, Bluetooth® Low Energy, a cellular connection, ultra-wideband (UWB), RFID, NFC, wireless local area network (WLAN), and/or any other wireless communication protocol. In some embodiments, the user device 1420 can transmit data to the vehicle 1402 based on the results of the drug screening. In some embodiments, for example, if the user passes the drug screening, the user device 1420 can transmit data to the vehicle 1402 including instructions for the vehicle 1402 to turn on and/or allow the user to operate the vehicle 1402. In some embodiments, for example, if the user fails the drug screening, the user device 1420 can automatically request a ride from the third-party driving service. In some embodiments, the user device 1420 can transmit a GPS location of the user to the system 1400 and the system 1400 can request a ride from the third-party driving service. In some embodiments, the user device 1420 and/or the system 1400 can transmit the results of the drug screening to the user's sponsor and/or any other third party.

In some embodiments, the user device 1420 can communicate with the speakers 1412, the display 1410, and/or other audio devices or video devices of the vehicle 1402 and/or the system 1400 via the wired and/or wireless connection. In some embodiments, the user device 1420 can transmit electronic messages and/or data received from the proctor to the vehicle 1402 via the wired and/or wireless connection so the one or more speakers 1412, the display 1410 and/or other audio devices or video devices can output images, video, and/or audio to the user.

In some embodiments, the one or more drug screening devices 1408 can include a breath-based drug screening device and/or a touch-based drug screening device. In some embodiments, the breath-based drug screening device can be configured to determine the presence of a drug in a sample provided by the user, the concentration of the drug in the user, and/or the concentration of the drug in the blood of the user. In some embodiments, the breath-based drug screening device can be configured to generate a beam of light. In some embodiments, the beam of light can include infrared light, ultraviolet light, and/or any other light frequencies. In some embodiments, the breath-based drug screening device can be configured to receive breath of the user via one or more openings. In some embodiments, the beam of light can be directed at one or more molecules of the breath of the user. In some embodiments, the breath-based drug screening device can determine an amount of light absorbed by the one or more molecules to determine the presence of the drug in the sample provided by the user, the concentration of the drug in the user, and/or the concentration of the drug in the blood of the user. For example, in some embodiments, carbon dioxide molecules can absorb a different amount of light than alcohol molecules. In some embodiments, the breath-based drug screening device can automatically determine a concentration of molecules of the drug in the breath of the user based on the amount of light absorbed by the one or more molecules.

In some embodiments, the vehicle 1402 can include an airflow system. In some embodiments, the airflow system can filter air, and/or direct a flow of the air in a cabin of the vehicle 1402 to ensure the breath-based drug screening device receives substantially only the breath of the user and/or only the breath of the user. In some embodiments, the breath-based drug screening device 1408 can include the airflow system.

Figure 14B:
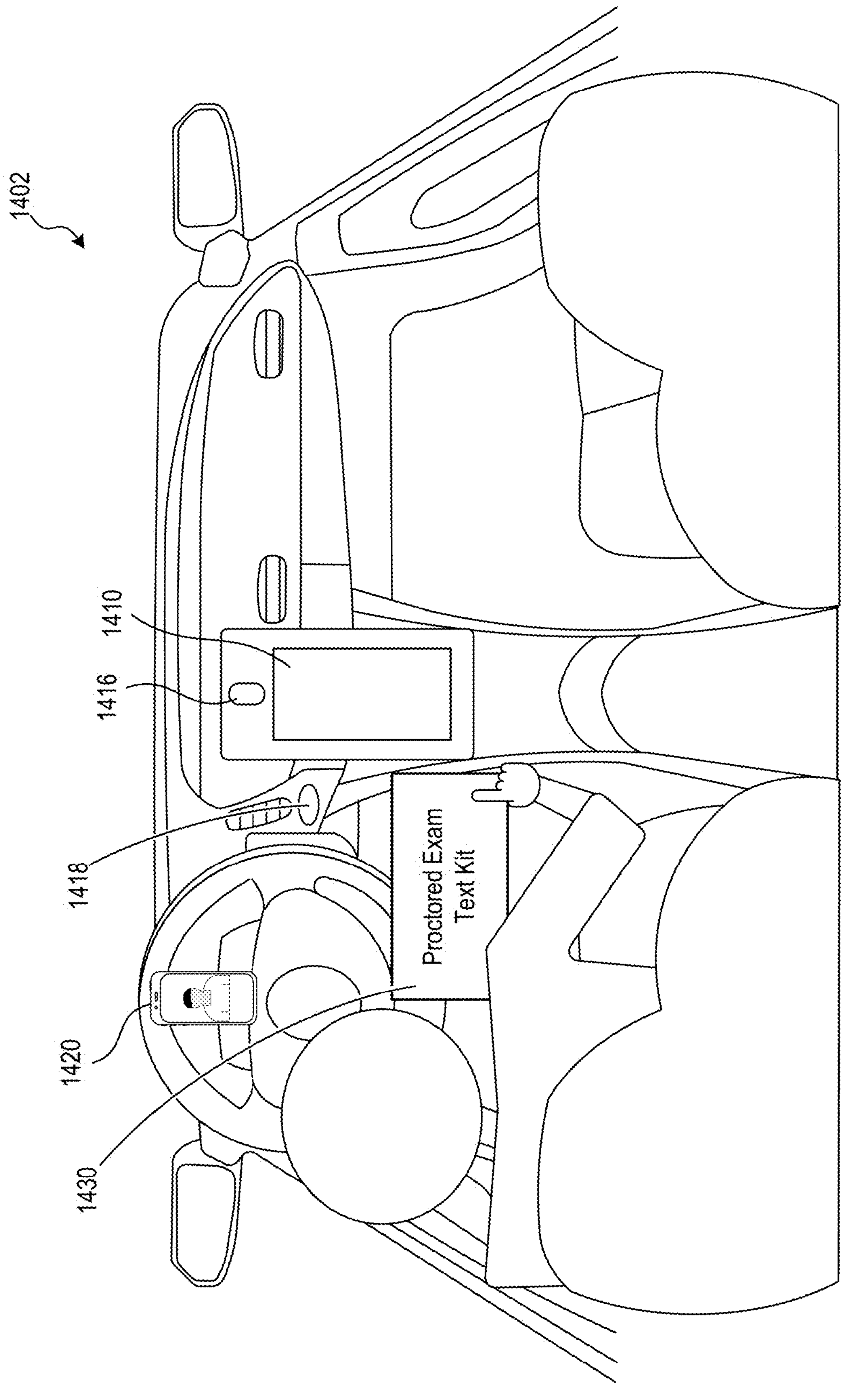
FIGS. 14B-14D show examples of in-vehicle drug testing according to some embodiments.
Figure 14C:
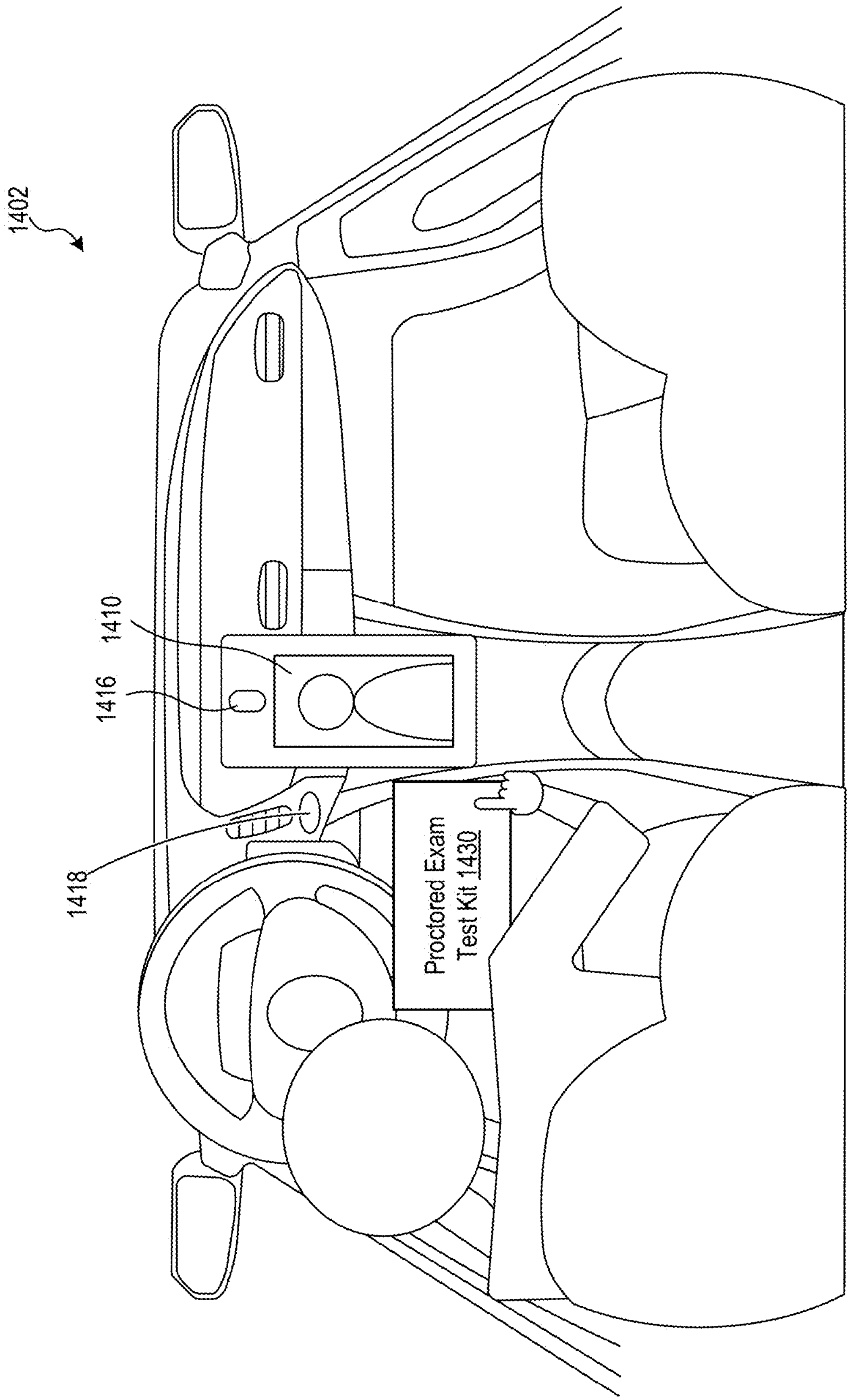
Figure 14D:
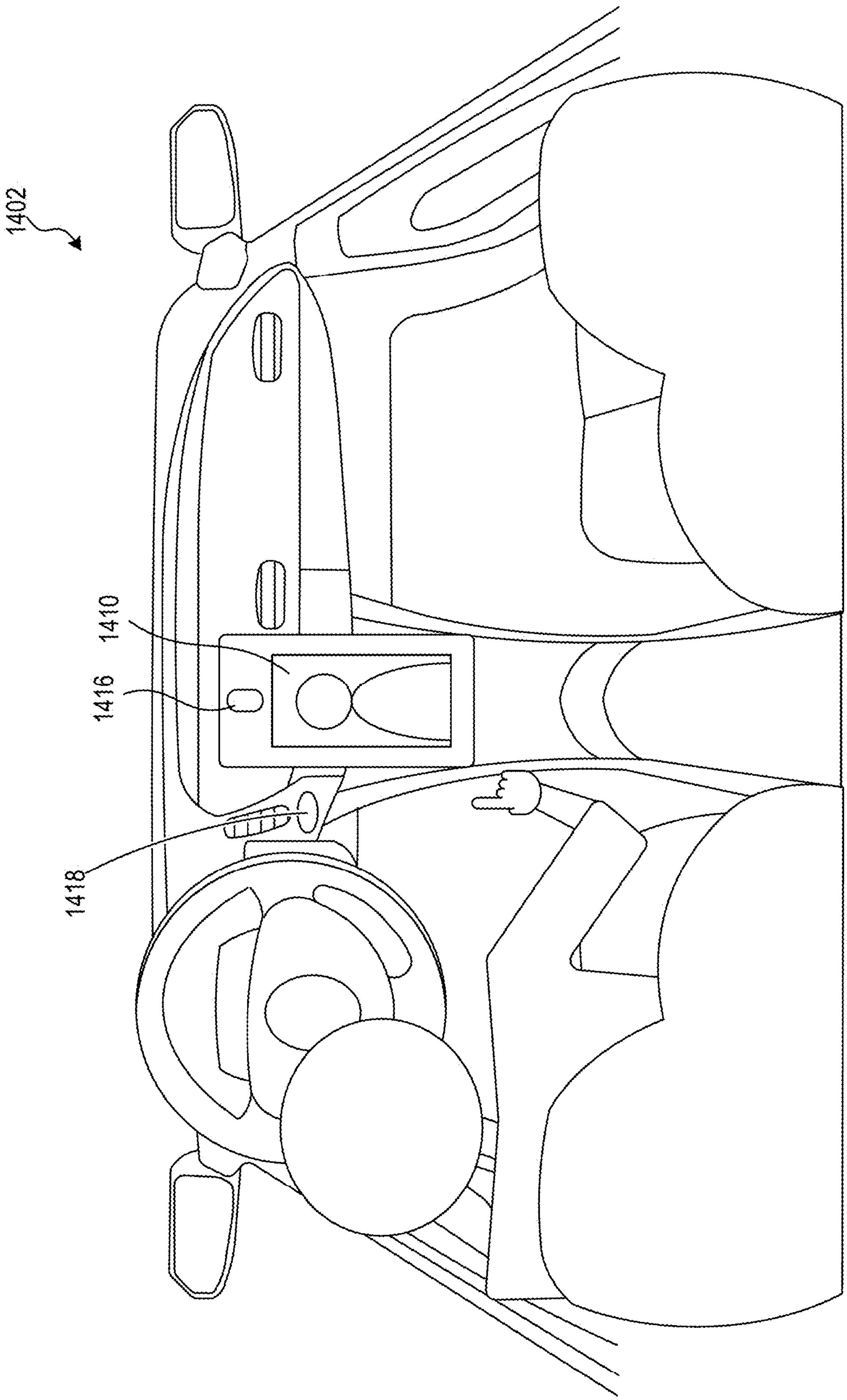

FIGS. 14B-14D show examples of in-vehicle drug testing according to some embodiments. As shown in FIGS. 14A-14B, a user can use a drug testing kit 1430 in conjunction with a user device 1420 and other equipment located in the vehicle (e.g., permanently integrated into a vehicle and/or otherwise installed in a vehicle). For example, a camera 1416 can be installed in the vehicle. A biometric sensor 1418 (e.g., a breath- or touch-based sensor) can be installed in the vehicle.

Figure 15:
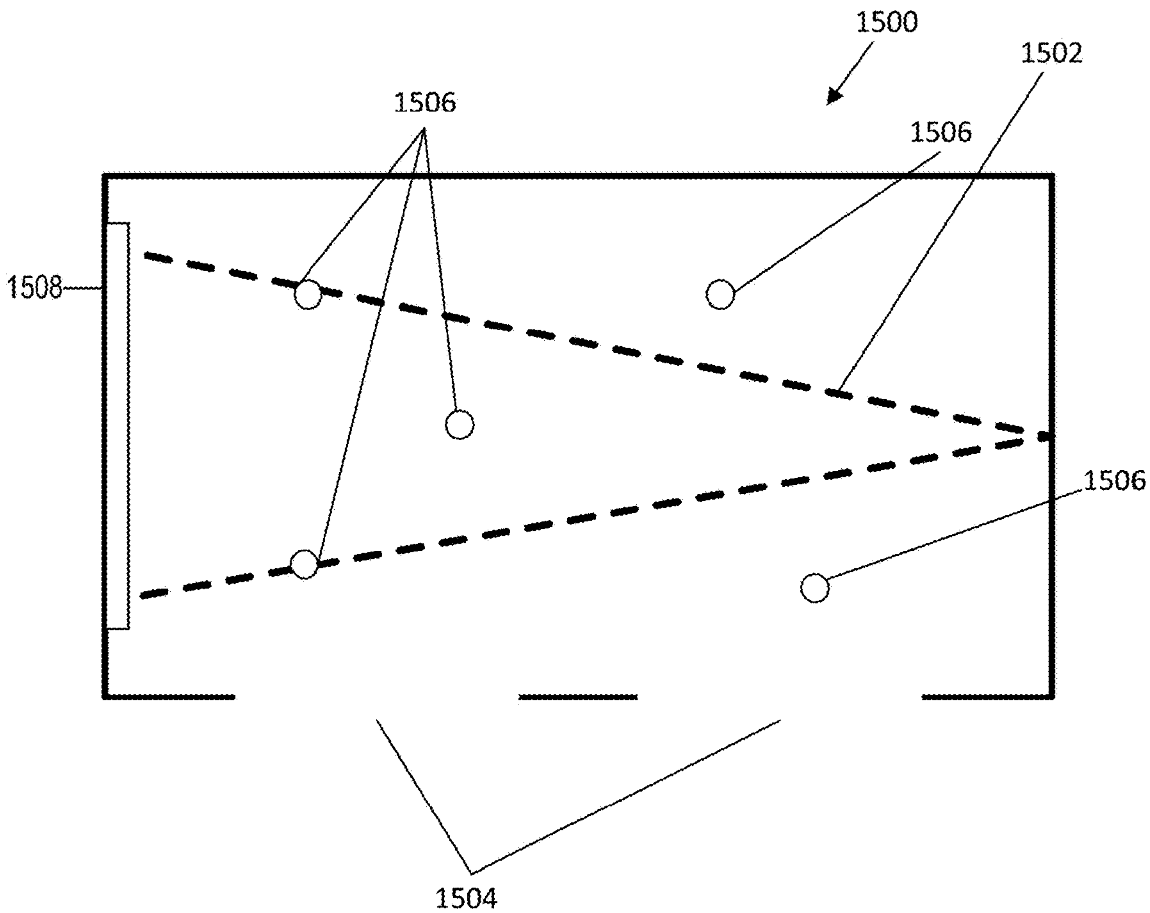
FIG. 15 illustrates a breath-based drug screening device according to some embodiments.

FIG. 15 illustrates a breath-based drug screening device 1500 according to some embodiments. The breath-based drug screening device 1500 can be configured to detect the presence of a drug in a sample provided by the user, the concentration of the drug in the user and/or the sample, and so forth. In some embodiments, the breath-based drug screening device 1500 can be configured to generate a beam of light 1502. The light 1502 can include infrared light, near-infrared light, ultraviolet light, visible light, and/or any other frequency or range of frequencies. For example, the frequency and/or range of frequencies can depend upon the absorption characteristics of a drug of interest. The breath-based drug screening device 1500 can include one or more openings 1504 for receiving the breath of a user. The light 1502 can be directed at molecules received via the one or more openings 1504. The light 1502 can interact with molecules 1506 in the breath of the user, which can result in absorption of some of the light. A sensor 1508 can detect the light. The output of the sensor 1508 can be used to determine the presence and/or concentration of a drug or a plurality of drugs. The breath-based drug screening device 1500 is merely an example, and other configurations are possible. For example, in some embodiments, the breath-based sensor can include a reference beam inside a sealed chamber, and light sensed from the reference beam can be compared to light sensed after passing through the breath of the user to detect the presence and/or concentration of one or more drugs.

In some embodiments, the touch-based drug screening device can be configured to determine the presence of a drug in a user, the concentration of the drug in the user and/or the concentration of the drug in the blood of the user. In some embodiments, the touch-based drug screening device can be configured to determine the presence of the drug in the user, the concentration of the drug in the user and/or the concentration of the drug in the blood of the user below the surface of the skin of the user. In some embodiments, the touch-based drug screening device 1408 can be configured to generate a beam of light. In some embodiments, the beam of light can include infrared light, ultraviolet light, and/or any other light frequencies. In some embodiments, the touch-based drug screening device can direct the beam of light at a portion of the skin of the user. In some embodiments, the portion of the skin of the user can include a finger of the user, a palm of the user, a back of a hand of the user, a forehead of the user, and/or any other portion of the skin of the user.

In some embodiments, the touch-based drug screening device can use near-infrared tissue spectroscopy to determine the concentration of the drug in the user and/or the concentration of the drug in the blood of the user below the surface of the skin of the user. In some embodiments, the touch-based drug screening device can automatically analyze the beam of light after the beam of light reflects off the portion of the skin of the user. In some embodiments, the touch-based drug screening device can automatically determine an intensity of the beam of light after the beam of light reflects off the portion of the skin of the user. In some embodiments, the touch-based drug screening device can automatically determine the concentration of the drug in the user and/or the concentration of the drug in the blood of the user based on the intensity of the beam of light.

In some embodiments, the one or more drug screening devices (e.g., the breath-based drug screening device, the touch-based drug screening device) can include the sensors 1406 (e.g., biometric sensors). In some embodiments, the system 1400 can use the one or more biometric sensors to confirm that the sample, the breath, and/or the portion of the skin of the user received by the one or more drug screening devices is provided by the user. In some embodiments, the system 1400 can use the one or more biometric sensors to confirm that the sample, the breath, and/or the portion of skin received by the one or more drug screening devices is not provided by a user other than the user. The system 1400 can use the one or more biometric sensors to confirm that the sample, the breath, and/or the portion of skin received by the one or more drug screening devices 1408 is provided by a user in the driver's seat of the vehicle 1402.

Figure 16:
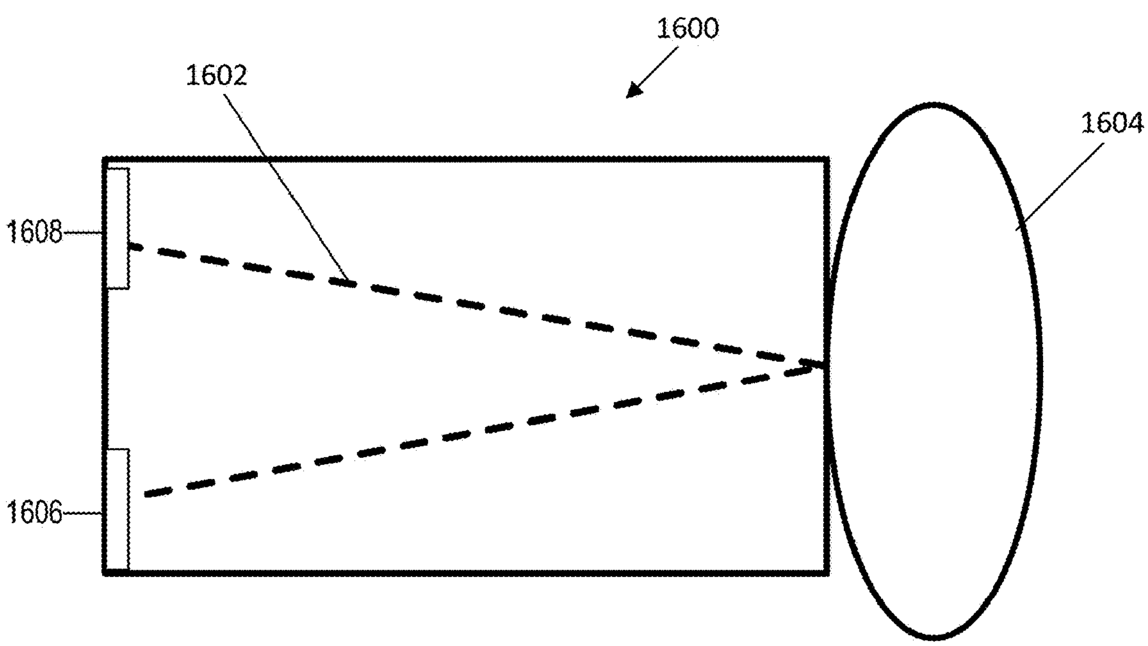
FIG. 16 shows an example of a touch-based sensor according to some embodiments.

FIG. 16 shows an example of a touch-based sensor according to some embodiments. The touch-based sensor 1600 can include a beam of light 1602 and a sensor 1606. In some embodiments, light can be emitted from a light source 1608, reflect off the skin of the user 1604 (e.g., can penetrate a depth in the skin 1604) and can be reflected into the sensor 1606.

In some embodiments, the sensors 1406 can include one or more cameras. In some embodiments, the one or more cameras can be positioned on a dashboard of the vehicle 1402, the door of the vehicle 1402, a steering wheel of the vehicle 1402, a steering column of the vehicle, a center console of the vehicle 1402, a control panel of the vehicle 1402, a headrest of a seat of the vehicle 1402, a rearview mirror of the vehicle 1402, a windshield of the vehicle 1402, and/or any other location of the interior of the vehicle 1402.

In some embodiments, the one or more cameras can be positioned so the user 1401 is within a field of view of the one or more cameras when the user is sitting in a driver's seat, a front passenger seat, and/or a back passenger seat of the vehicle 1402. In some embodiments, the one or more cameras can be positioned so an arm of the user is within the field of view of the one or more cameras. In some embodiments, the one or more cameras can be positioned so the user's face is within the field of view of the one or more cameras. In some embodiments, the one or more cameras can be positioned so the one or more drug screening devices 1408 are within the field of view of the one or more cameras.

In some embodiments, the system 1400 can use image data captured by the one or more cameras to identify the user when the user enters the vehicle 1402, during the proctored drug screening session, and/or after the drug screening session. In some embodiments, the system 1400 can use the image data captured by the one or more cameras to determine whether the user is the person providing a sample for drug screening. In some embodiments, the system 1400 can use computer vision (CV) to identify the user, for example by comparing video of images of the user to store images or video (e.g., a stored identification of the user). In some embodiments, the system 1400 can use CV to analyze the image data captured by the one or more cameras to identify and/or track the user, an arm of the user, a head of the user, a hand of the user, a finger of the user and/or any other portion of the user or the body of the user. In some embodiments, the system 1400 can use CV to analyze the image data captured by the one or more cameras to identify and/or track a user, an arm of the user, a head of the user, a hand of the user, a finger of the user and/or any other portion of the user or the body of the user. In some embodiments, the system 1400 can identify and/or track the user to determine whether the user provides the sample to the one or more drug screening devices 1408. In some embodiments, the system 1400 can identify and/or track the user to determine whether the user provides the sample to the one or more drug screening devices 1408. In some embodiments, if the system 1400 determines the user provides the sample and/or the user does not provide the sample, the system 1400 can prevent or inhibit the vehicle 1402 from turning on. In some embodiments, if the system 1400 determines the user provides the sample and/or the user does not provide the sample, the system 1400 can prevent or inhibit the user from operating the vehicle 1402.

In some embodiments, the one or more cameras can be configured to determine whether the user is the driver of the vehicle 1402 after the drug screening session, for example, the one or more cameras can determine if the user changes with a different user after the drug screening session so the different user cannot drive the vehicle 1402 after the user completes the drug screening session.

In some embodiments, the display 1410 can be located on the dashboard of the vehicle 1402, the door of the vehicle 1402, the steering wheel of the vehicle 1402, the steering column of the vehicle, the center console of the vehicle 1402, the control panel of the vehicle 1402, the headrest of a seat of the vehicle 1402, the rearview mirror of the vehicle 1402, the windshield of the vehicle 1402, and/or any other location of the interior of the vehicle 1402. In some embodiments, the display 1410 can display text instructions, image or graphical instructions, a proctor, drug screening results, and/or any other information to the user.

In some embodiments, the one or more speakers 1412 can be configured to generate audio or sounds. In some embodiments, the one or more speakers 1412 can be configured to generate audio or sounds of a voice of the proctor, instructions, results of the drug screening, an/or any other audio.

In some embodiments, the processor 1414 can be configured to send and/or receive signals from any other components of system 1400. In some embodiments, the processor 1414 can analyze data received from the components of system 1400, for example, image data received from the one or more cameras.

In some embodiments, a method (e.g., a computer-implemented method, program instructions contained in a non-transient computer readable medium) for in-vehicle drug screening can include starting a drug screening session. In some embodiments, the drug screening session can be started when a user is near the vehicle 1402, within a distance threshold of the vehicle 1402, unlocks the vehicle 1402, opens a door to the vehicle 1402, enters the vehicle 1402, sits down in the vehicle 1402, puts a key in the ignition, attempts to start the vehicle 1402, and/or any other time before the user starts operating the vehicle 1402. In some embodiments, the communication module 1404, the one or more sensors 1406 can determine when the user is near the vehicle 1402, within a threshold distance of the vehicle 1402, unlocks the vehicle 1402, opens a door to the vehicle 1402, enters the vehicle 1402, sit down in the vehicle 1402, puts a key in the ignition, attempts to start the vehicle 1402, and/or any other time before the user starts operating the vehicle 1402. In some embodiments, the system 1400 can connect the user and/or the vehicle 1402 to a proctor via a video conference, a phone call, and/or any other communication format.

In some embodiments, the method can include identifying the user 1401. In some embodiments, the system 1400 can identify the user before, after, and/or at the same time the system 1400 starts the drug screening session. In some embodiments, the communication module 1404 can receive a user device identifier, such as a MAC address of the user device, and the system can use the user device identifier to identify the user. In some embodiments, the one or more cameras can capture image data of the user approaching the vehicle 1402, entering the vehicle 1402, and/or sitting or standing in the vehicle 1402, and the system 1400 can use CV to analyze the image data and identify the user. In some embodiments, the system 1400, via the display 1410 and/or the one or more speakers 1412, can prompt the user to capture one or more images of an identification of the user, such as a driver's license. In some embodiments, the system 1400 can compare the one or more image of the identification of the user to the image data of the user approaching the vehicle 1402, entering the vehicles 1402, and/or sitting or standing in the vehicle 1402 to identify the user. In some embodiments, the system 1400 can compare one or more stored images of the user to the image data of the user approaching the vehicle 1402, entering the vehicles 1402, and/or sitting or standing in the vehicle 1402 to identify the user.

In some embodiments, the method can include enabling or allowing the user to perform the drug screening. In some embodiments, the system 1400 can transmit, via the communication module 1404, the image data captured by the one or more cameras to the proctor device. In some embodiments, the proctor and/or the system 1400 can observe the user during the drug screening session. In some embodiments, the proctor and/or the system 1400 can verify that the user correctly performs each step of the drug screening. In some embodiments, the proctor and/or the system 1400 can verify that the user does not leave the field of view of the one or more cameras, a user other than the user does not enter the field of view of the one or more cameras, the user provides the sample, a different user other than the user does not provide the sample, and so forth.

In some embodiments, the one or more drug screening devices 1408, the breath-based drug screening device 1408, and/or the touch-based drug screening device 1408 can receive a sample from the user. In some embodiments, if the proctor and/or the system 1400 determines that a different user other than the user provides the sample, the proctor and/or the system 1400 can end the drug screening session. In some embodiments, if the proctor and/or the system 1400 determines that a different user other than the user provides the sample, the proctor and/or the system 1400 can determine that the user failed the drug screening.

In some embodiments, the one or more drug screening devices 1408 can analyze the sample to determine the presence of the drug in the sample provided by the user, the concentration of the drug in the user, and/or the concentration of the drug in the blood of the user. In some embodiments, the system can compare the presence of the drug in the sample provided by the user, the concentration of the drug in the user, and/or the concentration of the drug in the blood of the user to a threshold. In some embodiments, the threshold can be based on an age of the user, a status of the user, and/or the drug. In some embodiments, for example, if the drug is alcohol and the user is under 21, the threshold can include 0.0 BAC. In some embodiments, for example, if the drug us alcohol and the user is 21 or older, the threshold can include a legal limit for operating the vehicle 1402. In some embodiments, for example, if the drug is any drug other than alcohol, the threshold may include the detection of any amount of the drug.

In some embodiments, if the presence of the drug in the sample provided by the user, the concentration of the drug in the user, and/or the concentration of the drug in the blood of the user is at and/or below the threshold, the system 1400 can start the vehicle 1402.

In some embodiments, if the presence of the drug in the sample provided by the user, the concentration of the drug in the user, and/or the concentration of the drug in the blood of the user is at and/or above the threshold, the system 1400 can prevent and/or inhibit the user from operating the vehicle and/or the user from starting the vehicle 1402.

In some embodiments, system 1400 can be configured to transmit an electronic message to a third-party person, for example, the user's emergency contact, the user's spouse, the user's sponsor, etc. In some embodiments, the electronic message can include information about the results of the drug screening. In some embodiments, the information about the results of the drug screening can include that the user failed the drug screening, a concentration of one or more drugs, such as a blood alcohol level, a location of the vehicle 1402, a location of the user device 1420, a time when the user failed the drug screening, whether a ride has been requested with the third-party driving service, and/or any other information about the results of the drug screening. In some embodiments, the system 1400 can be configured to transmit a GPS location of the vehicle 1402 to the user device and/or the third-party person.

Figure 17:
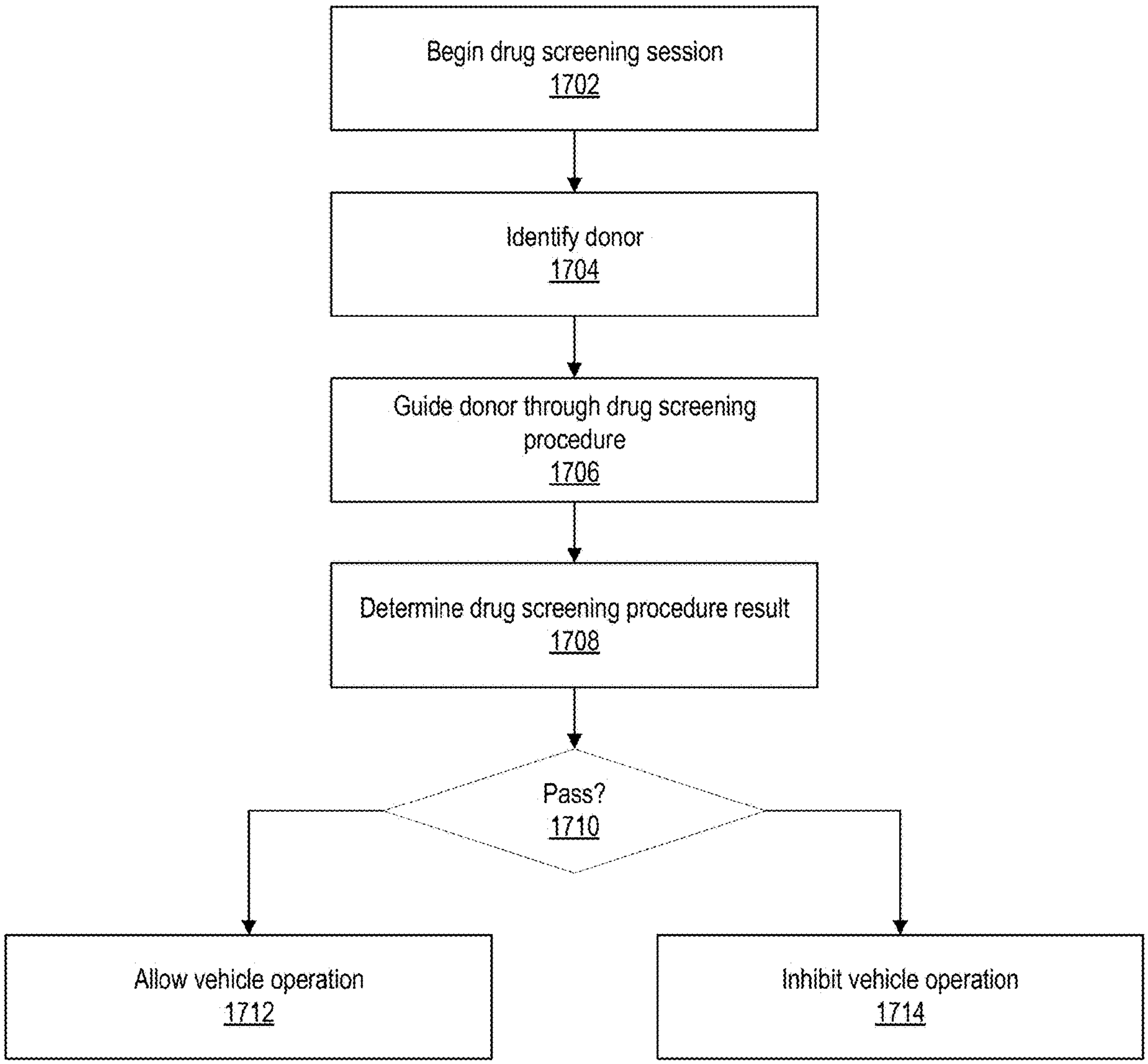
FIG. 17 is a flowchart that illustrates an example drug screen and vehicle access control process according to some embodiments.

FIG. 17 is a flowchart that illustrates an example drug screening and vehicle access control process according to some embodiments. At step 1702, a donor can begin a drug screening session with a telehealth service. At step 1704, the telehealth service can identify the donor. For example, the telehealth service can compare an image or video of the donor to a stored image or video of the donor's face (or a stored representation of the donor's face, such as a feature vector or hash). At step 1706, the telehealth service can guide the donor through a drug screening procedure and can monitor the donor to make sure that the procedure is followed without abnormalities. At step 1708, the telehealth service can determine a result of the drug screening. At decision point 1710, the telehealth service can determine if the donor passed the drug screen. If so, the telehealth system can allow vehicle operation at step 1712, for example the telehealth service can send a notification or other indication to an interlock device that allows operation of the vehicle. If the donor failed the drug screening, the telehealth service can inhibit vehicle operation at step 1714. In some embodiments, the telehealth service may not send a notification or other indication to the vehicle or an interlock device connected with the vehicle. In some embodiments, the telehealth service can send a notification or other indication that indicates that the donor failed the drug screening.

Diagnostic Testing

While much of the preceding discussion has focused on drug screening approaches, it will be appreciated that the approaches herein can be applied in other situations as well, such as diagnostic testing for conditions such as influenza, SARS-CoV-2, sexually transmitted infections, respiratory infections, urinary tract infections, and so forth. In some embodiments, test kits for diagnostics can be similar to those used for drug screening but can include some modifications. For example, return packaging may not be included for some diagnostic tests. In some cases, testing equipment can include, for example, a lateral flow strip.

When users utilize telehealth services for at home diagnostics, urgent care, general practitioner care, and so forth, it can be important to ensure that users efficiently obtain the care they need. In some cases, e.g., for diagnostic testing, users may interact with a provider but, in some cases, may not interact with a medical provider. For example, a user who takes a test for COVID 19 and has a negative result may not talk to a physician or other healthcare provider, while a user who does test positive or who is experiencing significant symptoms may interact with a healthcare practitioner.

Dynamic Provider Routing

In some cases, there can be many providers capable of providing telehealth services to users. However, different providers may be preferable for different users for a variety of reasons, such as expertise, insurance coverage, price, wait time, and so forth. In some cases, a provider may be selected based at least in part on whether a user is seeking a "one and done" interaction or an ongoing interaction.

Figure 18:
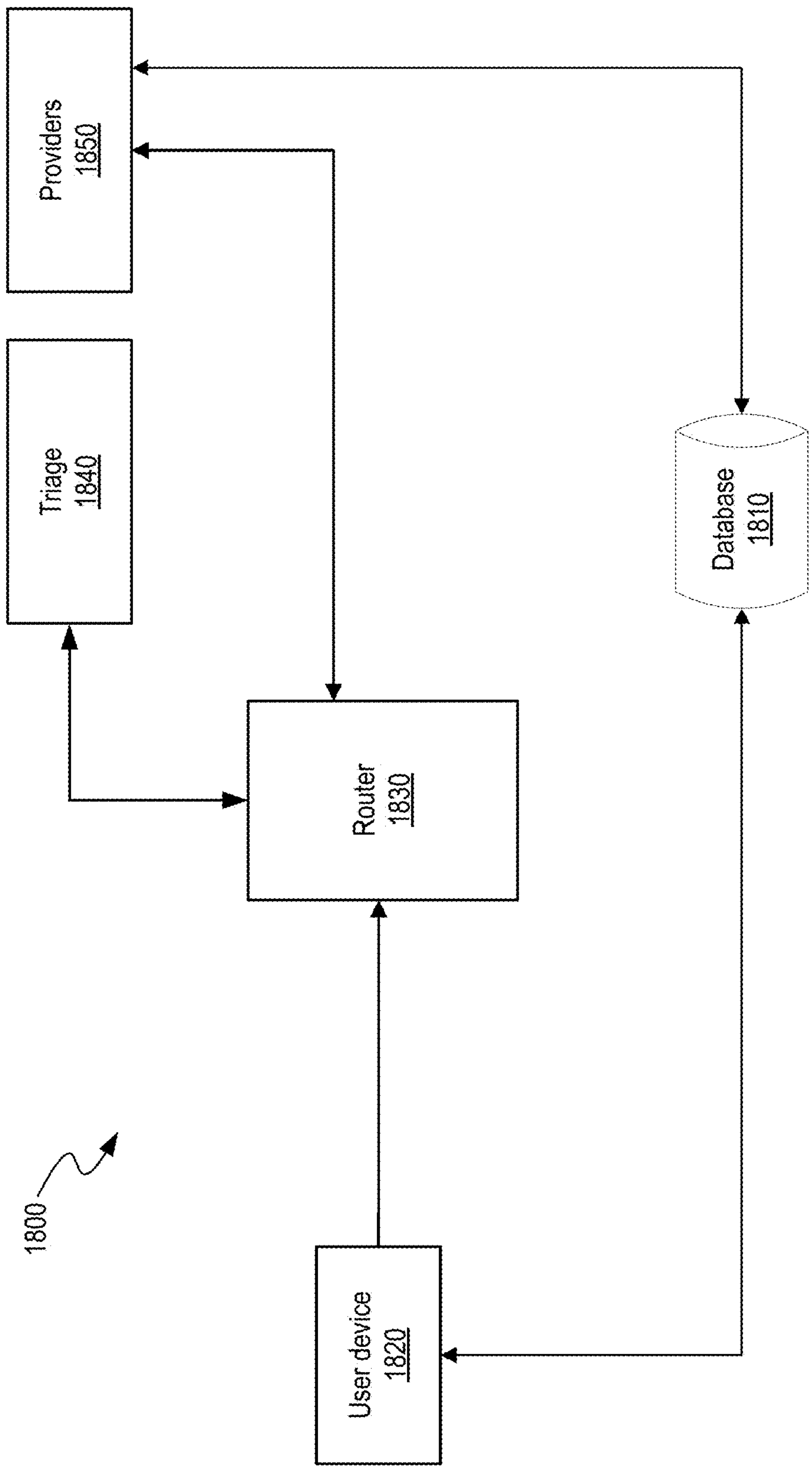
FIG. 18 is a schematic diagram illustrating a dynamic provider routing system according to some embodiments.

FIG. 18 is a schematic diagram illustrating a dynamic provider routing system 1800 in accordance with embodiments of the present technology. In some embodiments, a computer system and/or an algorithm (e.g., components of the telehealth platform 112) can perform one or more aspects of the dynamic provider routing system 1800. In some embodiments, the algorithm can be an artificial intelligence and/or a machine learning algorithm.

In some embodiments, a user device 1820 can access a telehealth platform (e.g., the telehealth platform 112). In some embodiments, the telehealth platform can transmit one or more questions to the user device 1820 from a database 1810. In some embodiments, the telehealth platform can automatically update the database 1810 with one or more updated questions or other updated information. In some embodiments, the telehealth platform can receive one or more updated questions from one or more telehealth providers 1850. In some embodiments, the one or more questions can include prompts for one or more diagnostic test, one or more prompts to capture an image, and/or one or more prompts to capture user health information, such as a temperature, audio of a cough, etc. In some embodiments, the telehealth platform can receive responses or answers to the one or more questions from a user via the user device 1820. In some embodiments, the responses or answers can include a text response, a selection of one or more predetermined responses, one or more images, a result of one or more tests (e.g., diagnostic test, screening test), audio, or any combination thereof.

In some embodiments, the telehealth platform can transmit the responses or answers to a router 1830. In some embodiments, the router 1830 can be a computer system and/or an algorithm. In some embodiments, the router 1830 can store the responses or answers in the database 1810 or other database. In some embodiments, the router 1830 can communicate with the one or more telehealth providers 1850.

In some embodiments, the router can transmit the responses or answers and/or any other patient information to a triage 1840. In some embodiments, the triage 1840 can determine which provider 1850 (e.g., a once-and-done telehealth provider, ongoing patient interaction telehealth provider, etc.) the router should connect the user device 1820 with. In some embodiments, the provider can be an asynchronous once-and-done telehealth provider. In some embodiments, the provider can be a synchronous once-and-done telehealth provider. In some embodiments, the provider can be an asynchronous traditional telehealth provider that can provide ongoing care. In some embodiments, the provider can be a synchronous traditional telehealth provider that can provide ongoing care. As used herein, synchronous telehealth providers can be providers that interact with users in real-time or near real-time. Asynchronous telehealth providers can be providers that do not interact with users in a real time or live manner. For example, a user can submit results and the asynchronous telehealth provider can contact the user after reviewing the results at a later time. Asynchronous telehealth can enable more cost-effective telehealth services as work can be performed by providers without a need for live availability. Asynchronous telehealth can be suited to conditions that do not require immediate attention or for which a delay is unlikely to have significant negative consequences. In some embodiments, the ongoing patient interaction telehealth provider 1850 and/or the once-and-done telehealth providers can provide services for a fixed fee.

In some embodiments, if the triage 1840 determines the router 1830 should connect the user device 1820 with a one and done telehealth provider and/or an ongoing interaction patient interaction telehealth provider (e.g., based on test results, symptoms, user preference, etc.), the router can receive one or more proposals from the telehealth providers 1850. In some embodiments, the router 1830 can receive proposals from a plurality of telehealth providers 1850. In some embodiments, the proposals can include a price or fee, an available time of the telehealth providers, a number of available medical professionals available for the telehealth provider, and/or any other information from the telehealth provider. In some embodiments, the price or fee can include a fee provided by the telehealth provider 1850 and/or a fee charged by the telehealth provider.

In some embodiments, after the router 1830 receives the proposals, the router 1830 can determine a best proposal. In some embodiments, the best proposal may be based on any of the information received from the telehealth providers 1850. In some embodiments, the router 1830 can connect the user with the telehealth provider 1850 with the best proposal. In some embodiments, a best proposal can be based on factors such as total cost, insurance coverage, time before a user can receive care from a provider, provider expertise, and so forth. For example, if a user reports symptoms consistent with influenza, the providers who treat influenza can be considered better than providers who do not or providers who focus on other issues for which users can seek telehealth services.

In some embodiments, if the triage 1840 determines the router 1830 should connect the user with a traditional telehealth provider, the router 1830 can refer the user to a traditional telehealth provider. In some embodiments, the router 1830 can receive proposals from one or more traditional telehealth providers. In some embodiments, after the router 1830 receives the proposals, the router can determine the best proposal. In some embodiments, the best proposal may be based on any of the information received from the traditional telehealth providers. In some embodiments, the router 1830 can connect the user with the traditional telehealth provider with the best proposal.

In some embodiments, the router 1830 can receive the proposals in real time after the router receives the responses or answers, and/or the router 1830 can receive proposals from the telehealth providers based on one or more possible responses or answers from the user device 1820. In some embodiments, the router can perform the aforementioned steps in real time or substantially real time.

Telehealth Test Interpretation

Figure 19:
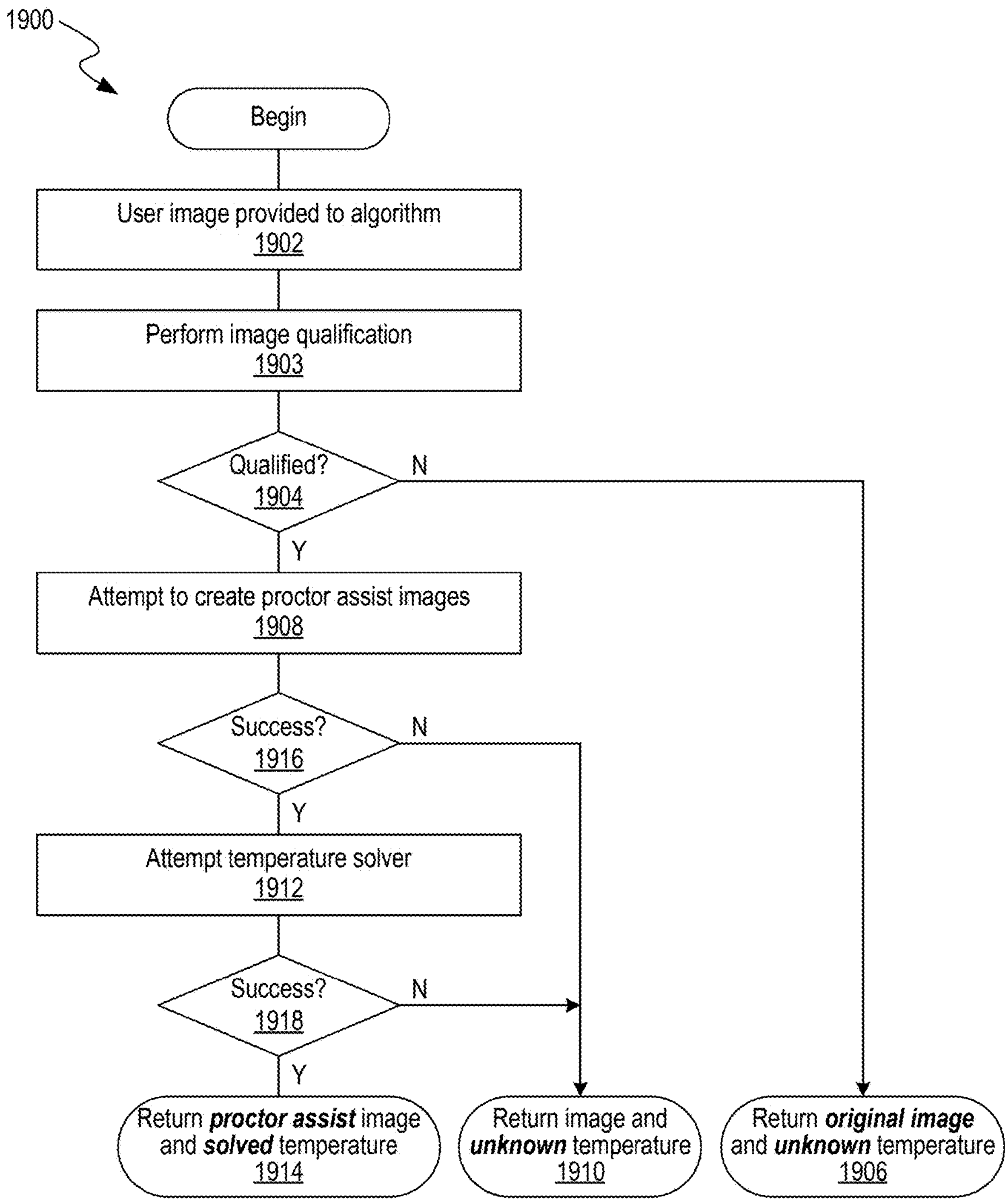
FIG. 19 shows a method for automatically and/or dynamically interpreting a temperature measurement of a thermometer according to some embodiments.
Figure 20:
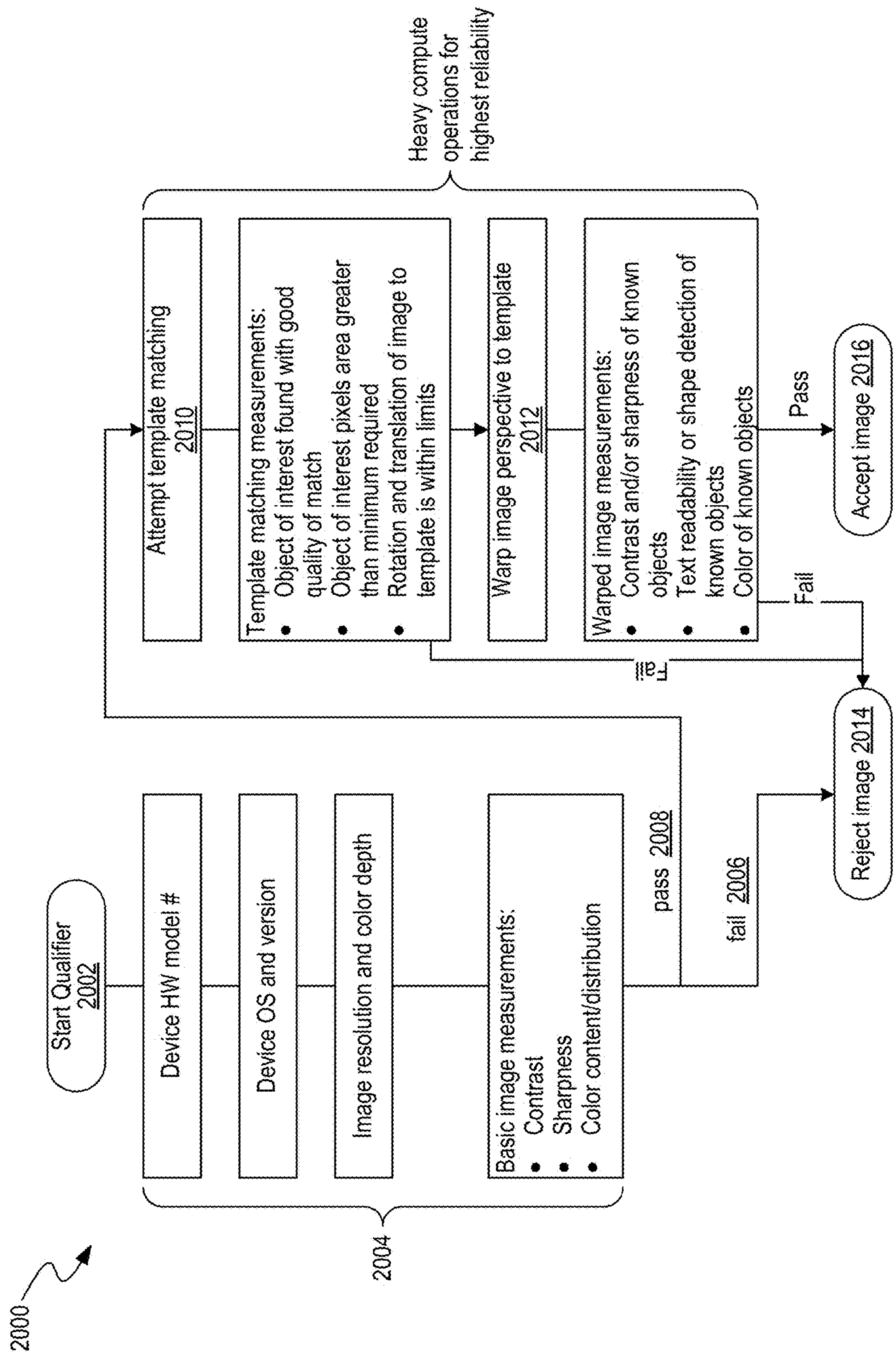
FIG. 20 is a flowchart illustrating a method of determining whether an image qualifies for interpretation according to some embodiments.
Figure 21:
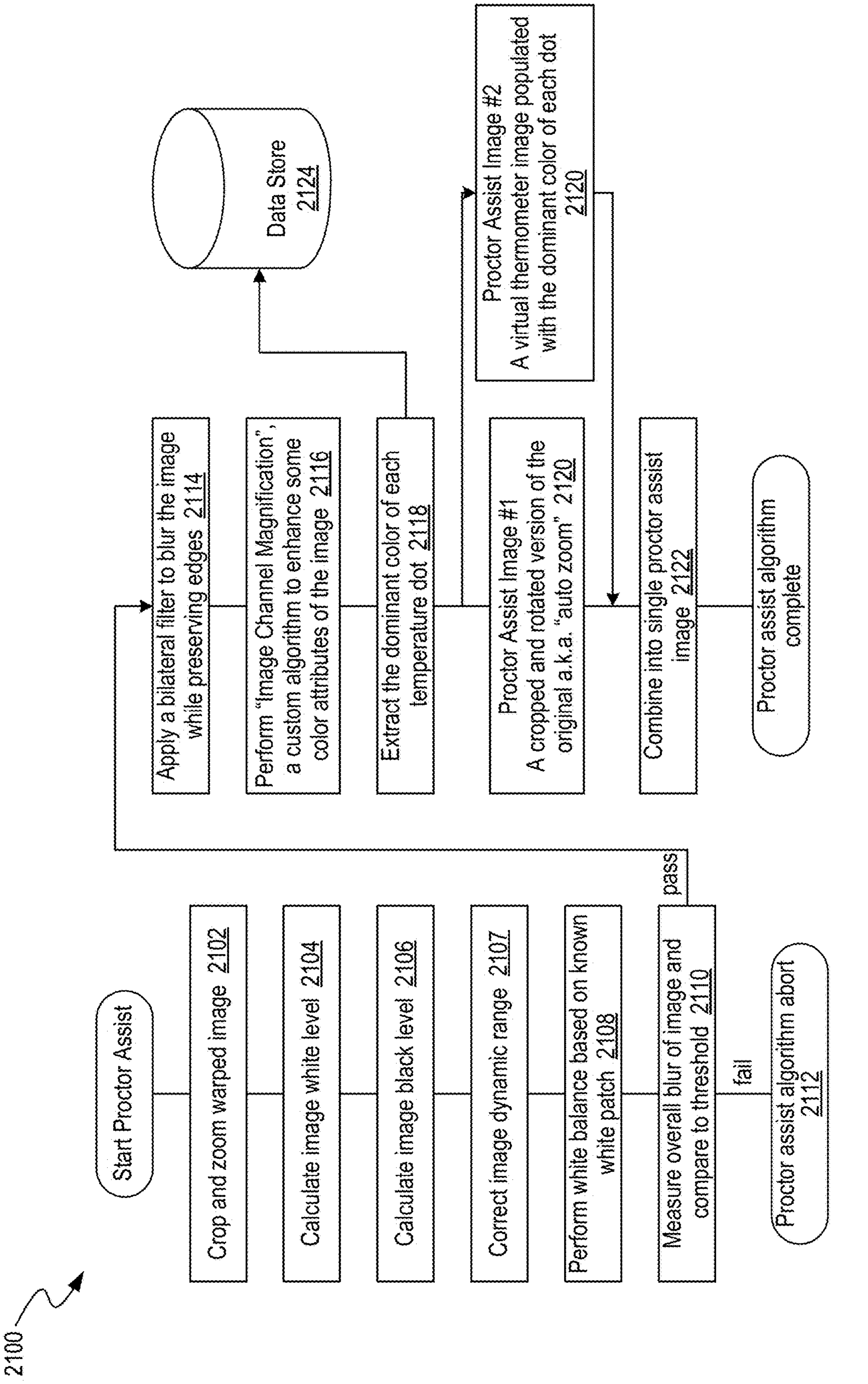
FIG. 21 is a flowchart illustrating a method of generating an assist image according to some embodiments.
Figure 23A:
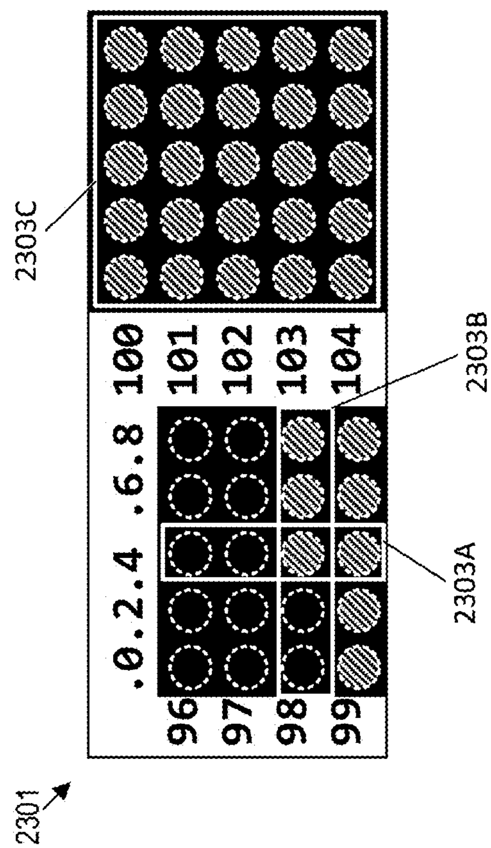
FIG. 23A shows an example of an image for determining a temperature value based on one or more images according to some embodiments.
Figure 23B:
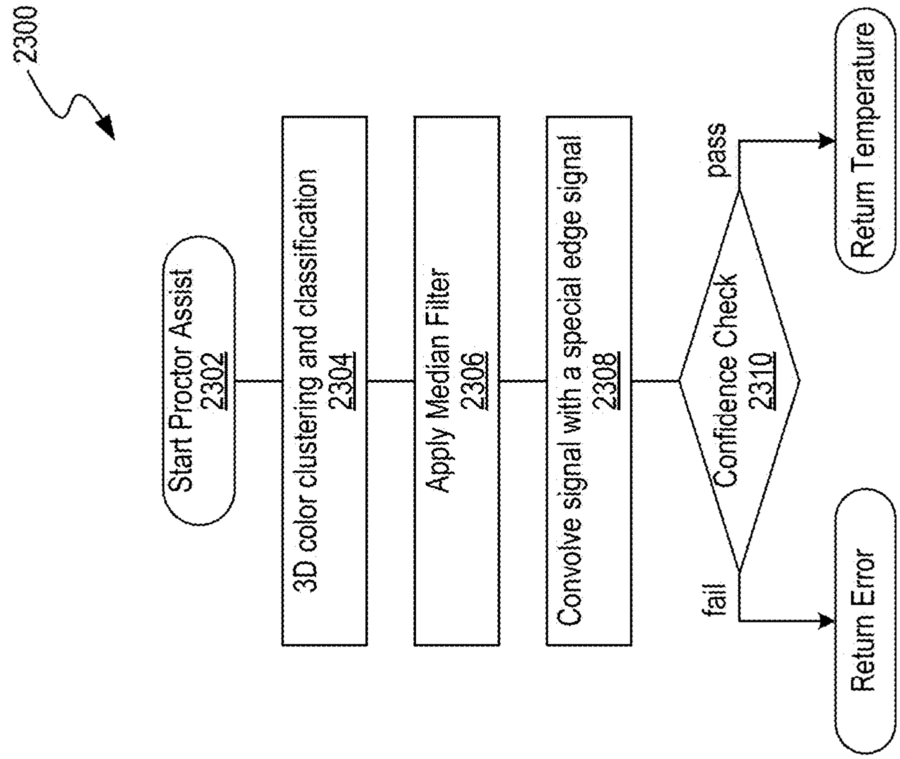

FIGS. 19-21 and 23B are flowcharts illustrating a method or portions thereof for performing a telehealth test in accordance with embodiments of the present technology. Specifically, FIG. 19 illustrates the method at a high level while FIGS. 20, 21, and 23B illustrate sub-steps that can be associated with one or more steps illustrated in FIG. 19. While the figures and the description below relate to reading temperature from a thermometer (e.g., NEXTEMP thermometer), a person of ordinary skill in the art will appreciate that the steps illustrated can be applied to other types of telehealth test procedures. For example, the steps below can be applied to performing various medical diagnostic tests (e.g., COVID test, pregnancy test, influenza test, etc.). For example, the methods described herein can be used to interpret a test strip (e.g., a lateral flow strip), the interpret a result panel (e.g., a result panel of a multi-panel drug test), and so forth.

FIG. 19 shows a method 1900 (e.g., a computer-implemented method, program instructions contained in a non-transient computer readable medium) for automatically and/or dynamically interpreting a temperature measurement of a thermometer. Thermometers (e.g., single use thermometers), can be accurate, but can be complicated to read and can be prone to human error. Misreading temperature results from thermometers can lead to a misdiagnosis of user symptoms, which can lead to a user receiving an incorrect treatment and/or ineffective treatment. Thus, it can be significant to capture one or more images of a thermometer reading so that the temperature reading can be interpreted by a computer system configured to interpret the temperature reading. In some cases, a proctor can assist with interpreting the temperature reading or can confirm the temperature reading. To aid the proctor, in some embodiments an image of the thermometer or a portion thereof including the thermometer reading can be modified, annotated, or otherwise manipulated to increase readability of the temperature reading. Such approaches can reduce the likelihood of misreading temperature results, which can improve diagnosis of user symptoms, improve overall quality of user care, and so forth.

In some embodiments, at step 1902, a user image is provided to a computer system and/or an algorithm, which receives the user image. In some embodiments, the algorithm can include an artificial intelligence (AI) algorithm, a machine learning (ML) algorithm, a computer vision (CV) algorithm, or any combination of two or more of an AI algorithm, an ML algorithm, or a CV algorithm. In some embodiments, a user can capture the image. In some embodiments, the user can capture the image via a camera. In some embodiments, the camera can be a camera of a user device. In some embodiments, the image can include at least a portion of a thermometer. In some embodiments, the thermometer can be a single-use thermometer. In some embodiments, the computer system, the algorithm, and/or a telehealth platform can prompt the user to capture the image. In some embodiments, the computer system, the algorithm, and/or a telehealth platform can prompt the user to capture the image with the thermometer on a white background, a black background, and/or any other color background. In some embodiments, the background can be a surface. In some embodiments, the computer system, the algorithm, and/or the telehealth platform can prompt the user to capture the image with the thermometer on a black card. In some embodiments, the black card and/or the thermometer can be part of a test kit (e.g., the kit 302). In some embodiments, the back card can be an access card of the test kit. In some embodiments, the user can capture the image with the thermometer on the white background, the black background, and/or any other color background. It has been found by the inventors that capturing an image on a solid card, surface, or other background can improve results of the techniques described herein. For example, capturing an image of the thermometer with a dark or black background can improve results of the techniques described herein.

In some embodiments, the computer system and/or algorithm can perform image qualification at step 1903, for example as described below with reference to FIG. 20. In some embodiments, the computer system and/or the algorithm can perform image qualification at step 1903 to determine if the image qualifies for automatic and/or dynamic interpretation at step 1904.

In some embodiments, if the computer system and/or the algorithm determines the image does not qualify at step 1904 (path "N"), the computer system and/or the algorithm can return or transmit the image (e.g., the original image received at step 1902) to a proctor at step 1906. In some embodiments, the computer system and/or the algorithm can transmit an unknown temperature message, alert, and/or notification to the proctor at step 1906. In some embodiments, the computer system and/or the algorithm can transmit an error message to the proctor.

In some embodiments, if the computer system and/or the algorithm determines the image qualifies at step 1904 (path "Y"), the computer system and/or algorithm can attempt to generate or create one or more proctor assist images at step 1908, for example as described below with reference to FIG. 21. At decision point 1916, the system can determine if the attempt to create the proctor assist images was successful. In some embodiments, if the attempt to generate or create the assist image at step 1908 is unsuccessful and/or the computer system and/or algorithm is unable to generate or create the assist image (path "N"), the computer system and/or the algorithm can transmit an image to the proctor at step 1910. In some embodiments, the computer system and/or the algorithm can transmit an unknown temperature message, alert, and/or notification to the proctor at step 1910. In some embodiments, the computer system and/or the algorithm can transmit an error message to the proctor.

In some embodiments, if the attempt to generate or create the assist image at step 1908 is successful (path "Y" from decision point 1916), at step 1912 the computer system and/or the algorithm can attempt a temperature solver based on the created proctor assist image, for example as described further below with reference to FIGS. 23A and 23B.

In some embodiments, if the attempt of the temperature solver is unsuccessful at step 1908 (path "N" from decision point 1918), the computer system and/or the algorithm can transmit the assist image to the proctor at step 1910. As discussed above, in some embodiments, the computer system and/or the algorithm can transmit an unknown temperature message, alert, and/or notification to the proctor at step 1910. In some embodiments, the computer system and/or the algorithm can transmit an error message to the proctor.

In some embodiments, if the attempt of the temperature solver is successful at step 1912 (path "Y"), the computer system and/or the algorithm can transmit the assist image to the proctor at step 1914. In some embodiments, the computer system and/or the algorithm can transmit a temperature to the proctor at step 1914. In some embodiments, the temperature may be a temperature determined or solved by the computer system and/or the algorithm, as further described below with reference to FIGS. 23A and 23B.

FIG. 20 is a flowchart illustrating a method 2000 of determining whether an image qualifies for interpretation. In some embodiments, at step 2002 the computer system and/or the algorithm can start the method 2000. In some embodiments, method 2000 can comprise sub-steps of the step 1903 of method 1900 described above with reference to FIG. 19.

In some embodiments, at step 2004, the computer system and/or the algorithm can retrieve and/or determine user device information and/or image information from a user device used to capture the image received at step 1902 of method 1900. In some embodiments, the user device information can include a device model number, a device hardware model number, a camera model number, a camera resolution, a device operating system, a device operating system version, and/or any other user device information. In some embodiments, the image information can include resolution, color depth, contrast, sharpness, color content, color distribution, f stop or depth of field, and/or any other image characteristics or measurements.

In some embodiments, if one or more of the user device information and/or the image information is below a predetermined threshold (e.g., image quality below a threshold, a user device with an operating system version below a threshold), a device is not included in a database of approved user device information, and/or the device is included in a database of disapproved user device information, the computer system and/or the algorithm can reject the image at step 2006 ("fail"). In some embodiments, if one or more of the user device information and/or the image information is above a predetermined threshold, included in a database of approved user device information, and/or not included in a database of disapproved user device information, the computer system and/or the algorithm can accept the image at step 2008 ("pass"). In some embodiments, the computer system and/or the algorithm can use operations to retrieve and/or determine the user device information and/or the image information at step 2004, for example by determining a device type based on information such as IMEI, determining image information from EXIF data, determining image information using a computer vision algorithm (e.g., to determine blur, identify edges, etc.) and so forth. In some embodiments, the operations can decrease a time for the computer system and/or the algorithm to retrieve and/or determine the user device information and/or the image information, which can increase a speed and/or frequency at which the computer rejects and/or accepts the image.

In some embodiments, if the computer system and/or the algorithm rejects the image at step 2006, the computer system and/or the algorithm can determine the image does not qualify at step 1903 of method 1900. In some embodiments, if the computer system and/or the algorithm accepts the image at step 2008, the computer system and/or the algorithm can continue on to process the image at step 2010.

In some embodiments, at step 2010, the computer system and/or the algorithm can attempt template matching. Template matching is a technique used in computer vision and image processing to find a sub-image (e.g., a template) within an input image. For example, a processor can translate, rotate, scale, or otherwise manipulate the template with respect to the input image and can compare the similarity between the template and the image. The position/scale where the template best matches a portion of the image is considered a potential match. In some embodiments, the template may not be scaled, and template matching can be based on the relative distances between alignment features. In some embodiments, the computer system and/or the algorithm can template match by (1) identifying one or more alignment features or fiducials (e.g., features of interest, such as edges or indicator features of a thermometer) in the received image (e.g., the image to be used for template matching), (2) matching the identified alignment features or fiducials to features in a template, and (3) modifying the received image to match the template to generate a matched image. For example, the computer system and/or the algorithm can perform a rotation operation, a translation operation, a skew operation, a resize operation, a cropping operation, or any combination thereof on the image so the identified features in the received image align with corresponding features of the template to generate a matched image. In some embodiments, the received image is modified such that the identified features in the received image positionally align with the corresponding features of the template. In some embodiments, the features can serve as fiducial points from which one or more coordinate frames can be generated by the computer system and/or the algorithm, and the coordinate frames can be used for improved template matching.

In some embodiments, upon generating the matched image, the computer system and/or the algorithm can compare a position of the alignment features in the matched image to a position of the corresponding features of the template to determine if the position of the alignment features and the position of the corresponding features of the template are within a maximum threshold distance. If yes, the method 2000 can proceed to step 2012. If not, in some embodiments, the method 2000 can repeat the template matching process for a predetermined number of attempts (e.g., 1, 2, 3, 10, 20). In some embodiments, if the positions of the features are not within the threshold distance on the first attempt or the predetermined number of attempts, or the computer system and/or the algorithm is otherwise unable to complete the template matching process, the method 2000 can proceed with rejecting the image at step 2014. For example, if the computer system and/or the algorithm are unable to determine one or more features in the image, the pixel area of the one or more features are less than the minimum pixel area threshold, and/or the position of the one or more features and the position of the corresponding one or more features of the template are not within a maximum threshold distance, the computer system and/or the algorithm can reject the image at step 2014. In some embodiments, if the computer system and/or the algorithm rejects the image at step 2014, the computer system and/or the algorithm can determine the image does not qualify at step 1904 of method 1900.

In some embodiments, at step 2012, the computer system and/or the algorithm can warp the generated matched image by applying a perspective warp to the matched image so the location of the one or more features of interest is the same as the location of the corresponding one or more features of the template or within a threshold distance of the location of the corresponding one or more features of the template, for example within 1 pixel, within 2 pixels, within 5 pixels, within 10 pixels, within 15 pixels, within 20 pixels, within 25 pixels, or within any value between these values, or more if desired. In some embodiments, the threshold can vary depending upon, for example, the image resolution. For example, thresholds can be higher for high resolution images, where each individual pixels represents a smaller physical distance. In some embodiments, the computer system and/or the algorithm can warp the matched image by applying the perspective warp, applying color correction (e.g., based on reference colors accessible by the computer system or reference colors contained in the image), modifying a contrast, modifying a sharpness, and/or modifying any other image characteristics to produce a warped image.

In some embodiments, the computer system and/or the algorithm can take measurements of or otherwise analyze the warped image. In some embodiments, the computer system and/or the algorithm can analyze the warped image to determine if one or more image characteristics are above a predetermined threshold corresponding to each of the one or more image characteristics. In some embodiments, the one or more image characteristics can include characteristics of one or more identified features or objects in the warped image. In some embodiments, the one or more image characteristics can include contrast, sharpness, text readability, shape detection, size, color, and/or any other image characteristics. In some embodiments, if one or more of the one or more image characteristics are below the corresponding predetermined threshold, the computer system and/or the algorithm can reject the warped image at step 2014. In some embodiments, if the computer system and/or the algorithm rejects the warped image at step 2014, the computer system and/or the algorithm can determine the image does not qualify at step 1904 of method 1900. In some embodiments, the computer system and/or the algorithm can carry out additional image manipulation steps, such as adjusting contrast, adjusting colors, applying a sharpening filter, and so forth.

In some embodiments, if one or more of the one or more image characteristics are above the corresponding predetermined threshold, the computer system and/or the algorithm can accept the warped image at step 2016. In some embodiments, if the computer system and/or the algorithm accepts the warped image at step 2016, the computer system and/or the algorithm can determine the image qualifies at step 1904 of method 1900.

As discussed above with reference to FIG. 19, if the computer system and/or the algorithm determines the image qualifies at step 1904 of method 1900, the computer system and/or the algorithm can attempt to generate or create an assist image at step 1908.

Figure 22:
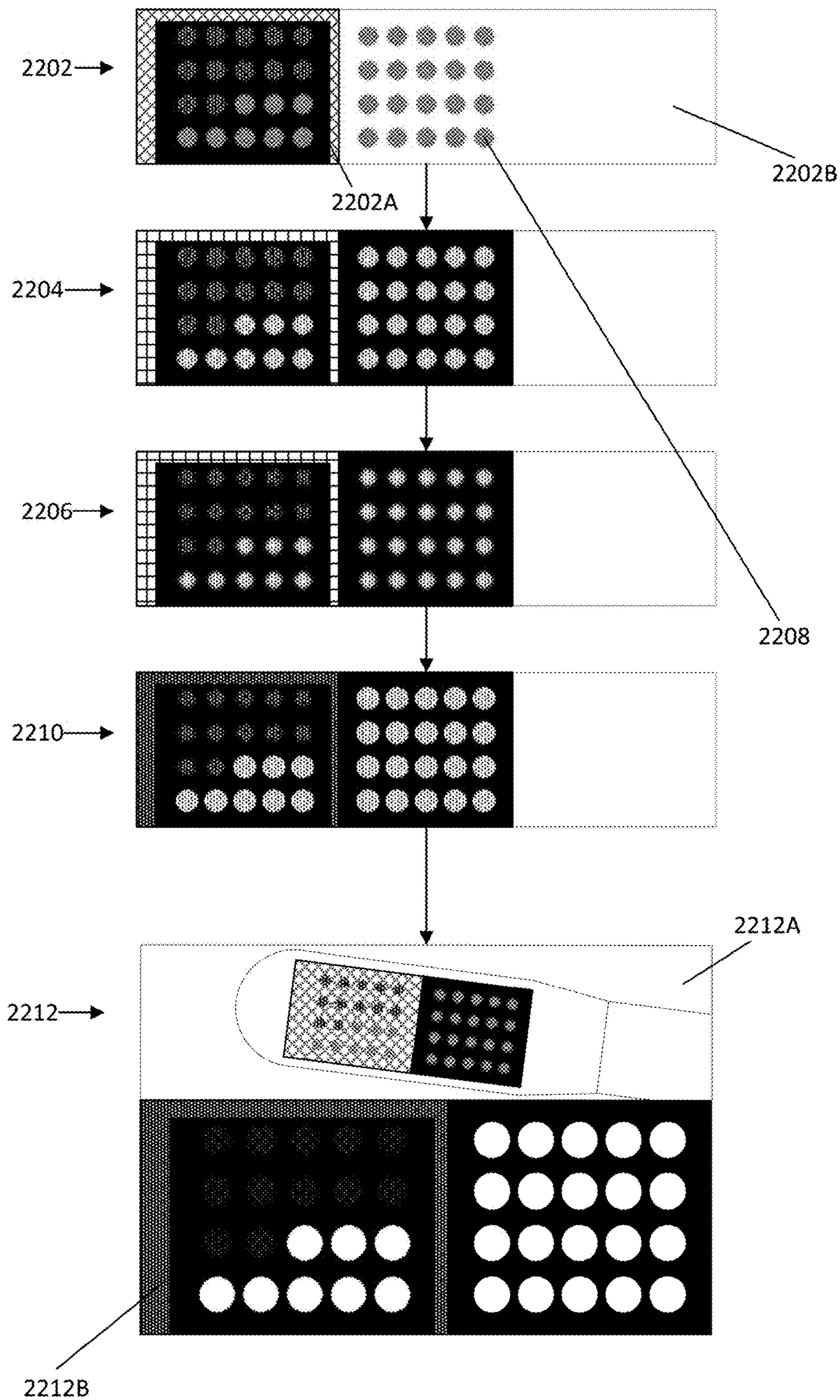
FIG. 22 illustrates various images of a thermometer captured or generated for image processing according to some embodiments.

FIG. 21 is a flowchart illustrating a method of generating an assist image. FIG. 22 illustrates various images of a thermometer captured or generated for image processing. In some embodiments, at step 2102, the computer system and/or the algorithm can crop and/or zoom in on the warped image to generate a cropped image 2202, as shown in FIG. 22. In some embodiments, the computer system and/or the algorithm can crop and/or zoom in on the warped image such that only a temperature measurement portion 2202A of the thermometer is in the cropped image 2210. In some embodiments, the thermometer can include a blank portion 2202B outside the temperature measurement portion 2202A, and the computer system and/or algorithm can crop and/or zoom in on the warped image such that the temperature measurement portion 2202A and tat least a part of the blank portion 2202B are in the cropped image 2210.

In some embodiments, the computer system and/or the algorithm can determine a white level or value of the cropped image 2202 at step 2104. In some embodiments, the computer system and/or the algorithm can analyze the temperature measurement portion 2202A and/or the blank portion 2202B to determine the white level or value of the cropped image 2202. In some embodiments, the computer system and/or the algorithm can determine a black level or value of the cropped image 2202 at step 2106. In some embodiments, the computer system and/or the algorithm can analyze the temperature measurement portion 2202A and/or the blank portion 2202B to determine a black level or value of the cropped image 2202.

In some embodiments, at step 2107, the computer system and/or the algorithm can correct or otherwise modify a dynamic range of the cropped image 2202. In some embodiments, the computer system and/or the algorithm can use the white level or value and/or the black level or value of the cropped image to modify the dynamic range of the cropped image 2202. In some embodiments, the computer system and/or the algorithm can increase or decrease the dynamic range of the cropped image 2202 based on the white level or value and/or the black level or value of the cropped image 2202.

In some embodiments, at step 2108, the computer system and/or the algorithm can modify a white balance of the cropped image 2202 to generate a balanced image 2204. In some embodiments, the computer system and/or the algorithm can determine the white balance of the cropped image 2202 based on the white level or value and/or the black level or value of the cropped image 2202. In some embodiments, the computer system and/or the algorithm can modify the white balance of the cropped image 2202 to generate the balanced image 2204 such that the white balance of the balanced image 2204 is within a predetermined range. In some embodiments, the computer system and/or the algorithm can modify the white balance of the cropped image 2202 to generate the balanced image 2204 such that the white balance of the balanced image 2204 is above a predetermined threshold. In some embodiments, the computer system and/or the algorithm can modify the white balance of the cropped image 2202 to generate the balanced image 2204 such that the white balance of the blank portion 2202B is within a predetermined range. In some embodiments, the computer system and/or the algorithm can modify the white balance of the cropped image 2202 to generate the balanced image 2204 such that the white balance of the blank portion 2202B is within a predetermined threshold, for example within 200 Kelvin or about 200 Kelvin, within 250 Kelvin or about 250 Kelvin, within 200 Kelvin or about 200 Kelvin, within 300 Kelvin or about 300 Kelvin, within 1900 Kelvin or about 1900 Kelvin, within 2000 Kelvin or about 2000 Kelvin, without 1,000 Kelvin or about 1,000 Kelvin, or any value between these values, or more or less, of a reference white balance.

In some embodiments, at step 2110, the computer system and/or the algorithm can determine a blur level of the balanced image 2204. In some embodiments, the computer system and/or the algorithm can analyze one or more features in the balanced image 2204 to determine a sharpness of the one or more features in the balanced image 2204. In some embodiments, the computer system and/or the algorithm can compare the balanced image 2204 to a template to determine the blur level of the balanced image 2204. In some embodiments, the computer system and/or the algorithm can compare the blur level of the balanced image 2204 to a predetermined threshold. In some embodiments, if the blur level is below the predetermined threshold, the computer system and/or the algorithm may determine the balanced image 2204 fails. In some embodiments, if the blur level is above the predetermined threshold, the computer system and/or the algorithm may determine the balanced imaged 2204 fails.

In some embodiments, if the balanced image 2204 fails, the computer system and/or algorithm can exit or abort method 2100 at step 2112. In some embodiments, if the balanced image 2204 fails, the computer system and/or the algorithm can determine that an attempt to generate an assist image at step 1908 of method 1900 was unsuccessful and, the computer system and/or the algorithm can transmit the balanced image 2204 to the proctor at step 1910.

In some embodiments, if the blur level is below the predetermined threshold, the computer system and/or the algorithm may determine the balanced image 2204 passes. In some embodiments, if the blur level is above the predetermined threshold, the computer system and/or the algorithm may determine the balanced image 2204 passes. If the balanced image 2204 passes, the computer system and/or the algorithm can apply a filter (e.g., a bilateral filter) to the balanced image 2204 at step 2114 to produce a filtered image 2206. In some embodiments, the filter can blur the balanced image 2204. In some embodiments, the filter can blur the image and maintain, keep, or preserve edges of one or more features in the balanced image 2204. In some embodiments, the one or more features can include one or more temperature indicator features 2206 (e.g., temperature dots) and/or an edge of the temperature measurement portion 2202A.

In some embodiments, the computer system and/or the algorithm can modify one or more color attributes of the filtered image 2206 to generate an enhanced image 2210 at step 2116. In some embodiments, the computer system and/or the algorithm can enhance the one or more color attributes of the filtered image 2206. In some embodiments, the computer system and/or the algorithm can modify tone or more color attributes of the filtered image 2206 by applying an enhancing algorithm. In some embodiments, the enhancing algorithm can be an image channel magnification algorithm. At step 2118, in some embodiments, the computer system and/or the algorithm can extract a dominant color of each of the temperature indicator features 2208. In some embodiments, the extracted colors are stored for later use in a data store 2124.

In some embodiments, the computer system and/or the algorithm can extract a color of each of the one or more temperature indicator features 2206 in the enhanced image 2210. In some embodiments, the color may be a dominant color of each of the one or more temperature indicator features 2208. In some embodiments, the dominant color of each temperature dot can be a color that covers the largest portion of each temperature dot. In some embodiments, the computer system and/or the algorithm can store each of the dominant colors in a memory or database. In some embodiments, the actual dominant color value can be stored (e.g., an RGB value). In some embodiments, the stored dominant color value can be a simplified representation, such as "red," "green," or "blue." In some embodiments, the computer system and/or the algorithm can store each of the dominant colors in the memory or database so the computer and/or algorithm can use the dominant colors in method 2000, as described further below with reference to FIG. 20. In some embodiments, the computer system and/or the algorithm can store each of the dominant colors in the memory or database as an array of the dominant colors. In some embodiments, the array of the dominant colors can include a location of each of the dominant colors. In some embodiments, the array of dominant colors can also include a color of an area surrounding each of the temperature indicator features (e.g., temperature dots).

In some embodiments, the computer system and/or the algorithm can generate a first intermediary assist image 2212A and a second intermediary assist image 2212B at step 2120, as shown in FIG. 22. An assist image 2212 can comprise the first intermediary assist image 2212A and the second intermediary assist image 2212B. In some embodiments, the first intermediary assist image 2212A and the second intermediary assist image 2212B can be generated from the enhanced image 2210. In some embodiments, the computer system and/or the algorithm can crop, rotate, zoom in on, and/or otherwise modify the enhanced image 2210 to generate the first intermediary assist image 2212. In some embodiments, the computer system and/or the algorithm can crop, rotate, zoom in on, and/or otherwise modify the enhanced image 2210 so each of the temperature indicator features 2208 of the enhanced image 2210 are located at a predetermined location in the first intermediary assist image 2212.

In some embodiments, the computer system and/or the algorithm can generate the first intermediary assist image 2212 from the user-captured image received by the computer system and/or the algorithm at step 1902 of method 1900. In some embodiments, the computer system and/or the algorithm can crop, zoom, and/or rotate the user captured image to generate the first intermediary assist image 2212A. In some embodiments, the computer system and/or the algorithm can crop, zoom, and/or rotate the user-captured image to generate the first intermediary assist image 2212A such that the thermometer in the first intermediary assist image 2212A is oriented and sized so a proctor or user can determine a temperature reading in the first intermediary assist image 2212A.

In some embodiments, the computer system and/or the algorithm can modify a template of a thermometer (or other data collection device) to generate the second intermediary assist image 2212B. In some embodiments, the computer system and/or the algorithm can determine a location of each of the temperature indicator features 2208 in the enhanced image 2212 (e.g., in the first intermediary assist image 2212A and/or the second intermediary assist image 2212B). In some embodiments, the computer system and/or algorithm can fill or color each corresponding temperature dot of the thermometer template in the second intermediary assist image 2212B with the dominant color of each temperature dot of the enhanced image 2210. In some embodiments, the corresponding temperature indicator feature 2208 may be a temperature dot in the thermometer template with a same location or about the same location as a temperature indicator features 2208 of the enhanced image 2210. In some embodiments, the second intermediary assist image 2212B may be a computer-generated image.

In some embodiments, the computer system and/or the algorithm can combine the first intermediary assist image 2212A and the second intermediary assist image 2212B at step 2122 to generate a combined assist image. In some embodiments, the computer system and/or the algorithm can combine the first intermediary assist image 2212A and the second intermediary assist image 2212B such that the first intermediary assist image 2212A and the second intermediary assist image 2212B do not overlap, as illustrated in FIG. 22. In some embodiments, the first intermediary assist image 2212 can be above the second intermediary assist image 2212B. In some embodiments, the first intermediary assist image 2212A can be below the second intermediary assist image 2212B. In some embodiments, the first intermediary assist image 2212A can be on the right side of the second intermediary assist image 2212B. In some embodiments, the first intermediary assist image 2212A can be on the left side of the second intermediary assist image 2212B. In some embodiments, at least a portion of the first intermediary assist image 2212A and the second intermediary assist image 2212B can overlap. In some embodiments, the computer system and/or the algorithm can overlay first intermediary assist image 2212A on the second intermediary assist image 2212B. In some embodiments, the computer system and/or the algorithm can overlay the second intermediary assist image 2212B on the first intermediary assist image 2212A.

In some embodiments, if the computer system and/or the algorithm is able to generate the combined assist image, at step 2016, the computer system and/or the algorithm can determine the attempt to generate or create the assist image is successful at step 1908 of method 1900.

FIG. 23A shows an example of an image associated with the process illustrated in FIG. 23B for determining a temperature value based on one or more images. In some embodiments, at step 2302 the computer system and/or the algorithm can use the array of dominant colors stored in the memory or database (e.g., from step 2118 of the method 2100), the first intermediary assist image 2212A, the second intermediary assist image 2212B, and/or the assist image 2212 as an input. In some embodiments, the computer system and/or the algorithm can analyze the first intermediary assist image 2212A, the second intermediary assist image 2212B, and/or the combined assist image 2212A to determine the array of dominant colors. In some embodiments, the computer system and/or the algorithm can modify the first intermediary assist image 2212A, the second intermediary assist image 2212B, and/or the combined assist image 2212 to generate a first input image and a second input image. In some embodiments, the first input image can be a color version of the array of dominant colors, the first intermediary assist image 2212A, the second intermediary assist image 2212B, and/or the combined assist image 2212. In some embodiments, the first input image can comprise a color extracted from the array of dominant colors. In some embodiments, the second input image can be a grayscale version of the array of dominant colors, the first intermediary assist image 2212A, the second intermediary assist image 2212B, and/or the combined assist image 2212.

In some embodiments, at step 2304, the computer system and/or the algorithm can perform clustering and/or classification. In some embodiments, the computer system and/or the algorithm can use the first input image and/or the second input image to perform clustering and/or classification. In some embodiments, the computer system can SIFT template match the second input image against a thermometer template image. In some embodiments, the computer system and/or the algorithm can transform the second input image to a coordinate system of the thermometer template image. In some embodiments, the computer system and/or the algorithm can transform the second input image such that each of the temperature dots in the second input image are located at the location of corresponding temperature dots of the thermometer template image.

In some embodiments, the computer system and/or the algorithm can extract a region of interest from the second input image. In some embodiments, the region of interest can include the dot grid 2301 (e.g., a portion of the second input image including the temperature dots and the black portion of the second input image). In some embodiments, the region of interest can include each temperature dot. In some embodiments, the computer system and/or the algorithm can determine a brightness of each temperature dot. In some embodiments, the brightness can be an average brightness of every pixel of each temperature dot. In some embodiments, the computer system and/or the algorithm can determine a black brightness. In some embodiments, the black brightness can be a brightness of the area surrounding each of the temperature dots from the array of dominant colors. In some embodiments, the computer system and/or the algorithm can use the area surrounding each of the temperature dots from the array of dominant colors to determine the area surrounding each of the temperature dots in the second input image. In some embodiments, the black brightness can be a brightness of the area surrounding each of the temperature dots in the second input image.

In some embodiments, the computer system and/or the algorithm can determine a contrast of each temperature dot. In some embodiments, the contrast can be a contrast ratio. In some embodiments, the computer system and/or the algorithm can determine the contrast based on the brightness of each temperature dot and the black brightness of the area surrounding each temperature dot. In some embodiments, the contrast can be a ratio of the brightness and the black brightness of each temperature dot.

In some embodiments, at step 2306, the computer system and/or the algorithm can determine a filter. In some embodiments, the computer system and/or the algorithm can determine a median filter. In some embodiments, the determined filter can be based on an analysis of the input image, for example based on determining a level of noise in an image. In some embodiments, the filter can be predetermined, for example a median filter with particular settings can be applied after analyzing an image and/or without conducting further image analysis. For example, median filters are filters commonly used for noise reduction, in which the values of pixels are updated to be the median value of pixels within a window. The window can be, for example, 1 pixel, 2 pixels, 3 pixels, 4 pixels, 5 pixels, 6 pixels, 7 pixels, 8 pixels, 9 pixels, 10 pixels, or more. In the case of a 2D image, the window can represent a radius, and pixels within the radius can be considered when determining the median. It will be appreciated that other filters can be applied. The median filter can be desirable because, for example, it can in some cases reduce noise significantly while preserving edges better than some other filtering algorithms, such as Gaussian blurring.

In some embodiments, the computer system and/or the algorithm can determine a mean or median contrast of all of the temperature dots in a column 2303A of temperature dots. In some embodiments, the computer system and/or the algorithm can generate a filter waveform of the mean or median contrast of all of the columns 2303A, wherein each data point of the filter waveform is the mean or median contrast of a different column 2303A. In some embodiments, each data point corresponds to a different subset of the temperature indicator features. In some embodiments, the computer system and/or the algorithm can determine a polynomial fit or equation of the filter waveform. In some embodiments, the polynomial fit or equation can be a first order, second order, third order or fourth order polynomial.

In some embodiments, the computer system and/or the algorithm can determine a mean or median contrast of all of the temperature indicator features (e.g., temperature dots) in block 2303C of temperature indicator features (e.g., temperature dots). In some embodiments, the computer system and/or the algorithm can generate a block filter waveform of the mean or median contrast of block 2303C, wherein each data point of the block filter waveform is the mean or median contrast of a different block of the blocks 2303C. In some embodiments, the computer system and/or the algorithm can determine a block polynomial fit or equation of the block filter waveform. In some embodiments, the block polynomial fit or equation can be a first order, second order, third order or fourth order polynomial. In some embodiments, instead of a polynomial, the equation can be a stepwise function, a sinusoidal function, etc.

In some embodiments, the median filter can include the polynomial fit or equation and/or the block polynomial fit or equation.

In some embodiments, at step 2308, the computer system and/or the algorithm can convolve a waveform. In some embodiments, the waveform can be a waveform with each data point of the waveform being the contrast of each temperature indicator feature (e.g., temperature dot). In some embodiments, the computer system and/or the algorithm can convolve the waveform by applying the median filter to the waveform. In some embodiments, the computer system and/or the algorithm can generate a filtered waveform by applying the median filter to the waveform. In some embodiments, the computer system and/or the algorithm can apply the median filter to the waveform by adding or subtracting the polynomial fit or equation to or form the data points of each row 2303B of temperature indicator features (e.g., temperature dots). In some embodiments, the computer system and/or the algorithm can apply the median filter by adding or subtracting the block polynomial fit or equation to or from the data points of each block 2303C of temperature indicator features (e.g., temperature dots).

In some embodiments, at step 2310, the computer system and/or the algorithm can determine the temperature reading and perform a confidence check. In some embodiments, the computer system and/or the algorithm can analyze the filtered wavelength to determine the temperature reading. In some embodiments, the computer system and/or the algorithm can analyze the filtered wavelength to determine a slope of every portion of the filtered wavelength between each data point. In some embodiments, the temperature reading can be the portion of the filtered wavelength having the largest slope. In some embodiments, the temperature reading can be a temperature associated with a data point on either end of the portion of the filtered wavelength with the largest slope.

In some embodiments, the computer system and/or the algorithm can perform the confidence check of the temperature reading. In some embodiments, the computer system and/or the algorithm can compare the slope of each portion of the filtered wavelength. In some embodiments, if a second portion of the filtered wavelength has a same slope as the portion of the filtered wavelength with the largest slope, or if a second portion of the filtered wavelength has a slope within a predetermined threshold of the portion of the filtered wavelength with the largest slope, the computer system and/or the algorithm can determine the temperature reading fails the confidence check. In some embodiments, if no other portion of the filtered wavelength has the same slope as the portion of the filtered wavelength with the largest slope, and/or no other portion of the filtered wavelength has a slope within the predetermined threshold of the portion of the filtered wavelength with the largest slope, the computer system and/or the algorithm can determine the temperature reading passes the confidence check.

In some embodiments, if the temperature reading passes the confidence check ("pass"), the computer system and/or the algorithm can return or output the temperature reading. In some embodiments, if the computer system and/or the algorithm returns or outputs the temperature reading, the computer system and/or algorithm can determine that the attempt of the temperature solver is successful at decision point 1918 of method 1900.

In some embodiments, if the temperature reading does not pass the confidence check ("fail"), the computer system and/or the algorithm can return or output an error. In some embodiments, if the computer system and/or the algorithm returns or outputs the error, the computer system and/or algorithm can determine that the attempt of the temperature solver is unsuccessful at decision point 1918 of method 1900.

In some embodiments, methods 1900, 2000, 2100, and 2300 can each be performed by one computer system and/or one algorithm. In some embodiments, methods 1900, 2000, 2100, and 2300 can each be performed by separate computer systems and/or algorithms, or the methods can be combined in various ways such that some methods are performed by one computer system and/or algorithm while other, different methods are performed by another computer system and/or algorithm. In some embodiments, methods 1900, 2000, 2100, and 2300 can be performed by a multi-stage algorithm. In some embodiments, the computer system can be a user device and/or a server. In some embodiments, the algorithm can be stored and/or run on the user device and/or a server. In some embodiments, at least a portion of the algorithm can be stored and/or run on the user device and at least a portion if the algorithm can be stored and/or run on the server. In some embodiments, the algorithm can be stored and/or run on a cloud based computing system.

Much of the above discussion relates to analyzing color images. In some cases, however, it can be simpler and/or more effective to analyze grayscale images. For example, in the case of a thermometer with temperature indicator features that change color, the baseline color of the temperature indicator features and the changed color of the temperature indicator features can be known ahead of time. For example, if a color indicator feature changes from black to green, in some embodiments, a computer system can be configured to extract a green channel from an RGB image (e.g., an image comprising red, green, and blue channels) and can perform subsequent processing steps on only the green channel. In some embodiments, processing can be carried out using saturation values, hue values, lightness values, and so forth. For example, if a temperature indicator feature becomes brighter when it undergoes a change, analysis can be performed using brightness values, lightness values, or the like. For example, RGB values can be converted to HSV, HSL, or other well-known color coding schemes.

Figure 24:
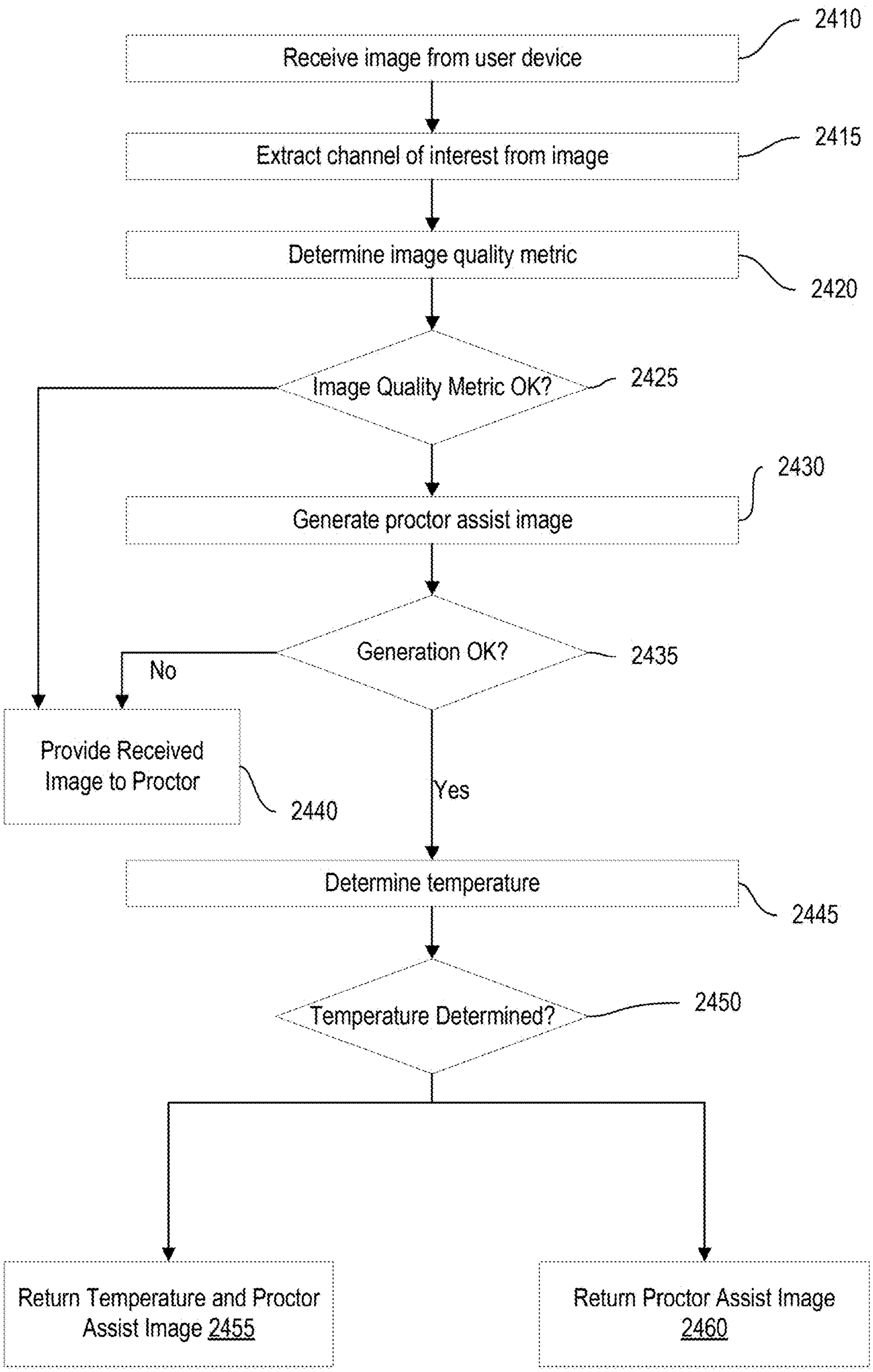
FIG. 24 illustrates an example process for determining a temperature from a received image according to some embodiments.

FIG. 24 illustrates an example process for determining a temperature from a received image according to some embodiments. At step 2410, a computing system can receive an image from a user device. The image can include a portion of a thermometer and can include a plurality of temperature indicator features (e.g., temperature dots). At step 2415, the computing system can extract a channel of interest from the image. For example, if the temperature indicator features turn green upon exposure to heat or have a green color prior to exposure to heat, the computer system can extract the green channel from the received image. At step 2420, the computing system can determine an image quality metric. The image quality metric can include one or more of an image resolution, an amount of blur in the image, an amount of noise in the image, a brightness of the image, a contrast of the image, and so forth. At decision point 2425, the system can determine if the image quality metric(s) is acceptable. If not, the computing system can provide the received image to the proctor at step 2440. In some embodiments, the computing system can be configured to provide a notification to user that the image was unacceptable, in which case the user can capture another image. If so, the system can attempt to generate a proctor assist image at step 2430. To generate the proctor assist image, the system can adjust one or more of scale, skew, warp, blur, noise, etc., for example as described above. In some embodiments, generating the proctor assist image can comprise matching the image to a template, for example as described above. In some embodiments. At decision point 2435 if generating the proctor assist image failed, the computing system can provide the receive image to a proctor at step 2440. If generating the proctor assist image succeeded, the computing system can determine the temperature at step 2445 by analyzing the image, for example as described herein. At decision point 2450, the computing system can determine if determining the temperature succeeded. If so, the computing system can return the temperature and the proctor assist image to the proctor at step 2455. If not, the computing system can return the proctor assist image at step 2460.

Figure 25:
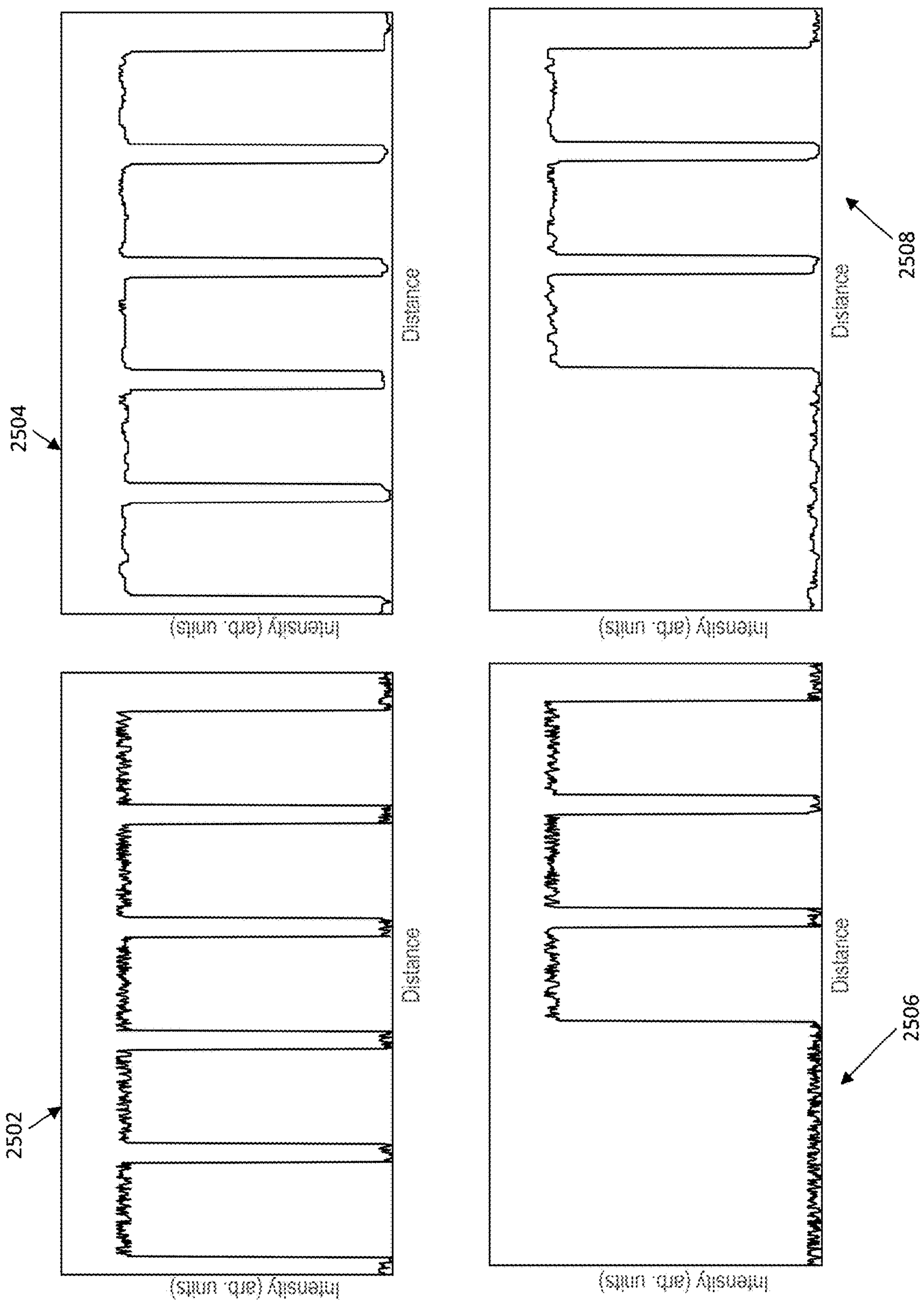
FIG. 25 illustrates examples of waveforms that can be used in temperature determination according to some embodiments.

FIG. 25 illustrates image processing according to some embodiments. Plot 2502 can represent an intensity of a single channel across a line segment passing through five colored temperature indicator features. Plot 2504 shows an example result of applying a median filter to the plot 2502, in which the noise has been reduced while preserving the boundaries between the indicator features (portions of high intensity) and the background (portions of low intensity). Plot 2506 is similar to plot 2502, except that two indicator features are uncolored (e.g., the temperature indicator features turned black in response to exposure to heat, or only some of the temperature indicator became colored in response to exposure to heat. Plot 2508 shows plot 2506 after application of a median filter. In some embodiments, the temperature of the user can be determined by analyzing plot 2508 to identify a first (e.g., leftmost) peak in the intensity. In some embodiments, plot 2504 can be subtracted from plot 2508 and the resulting plot can be analyzed to identify the temperature.

Post-Result Operations

Figure 26:
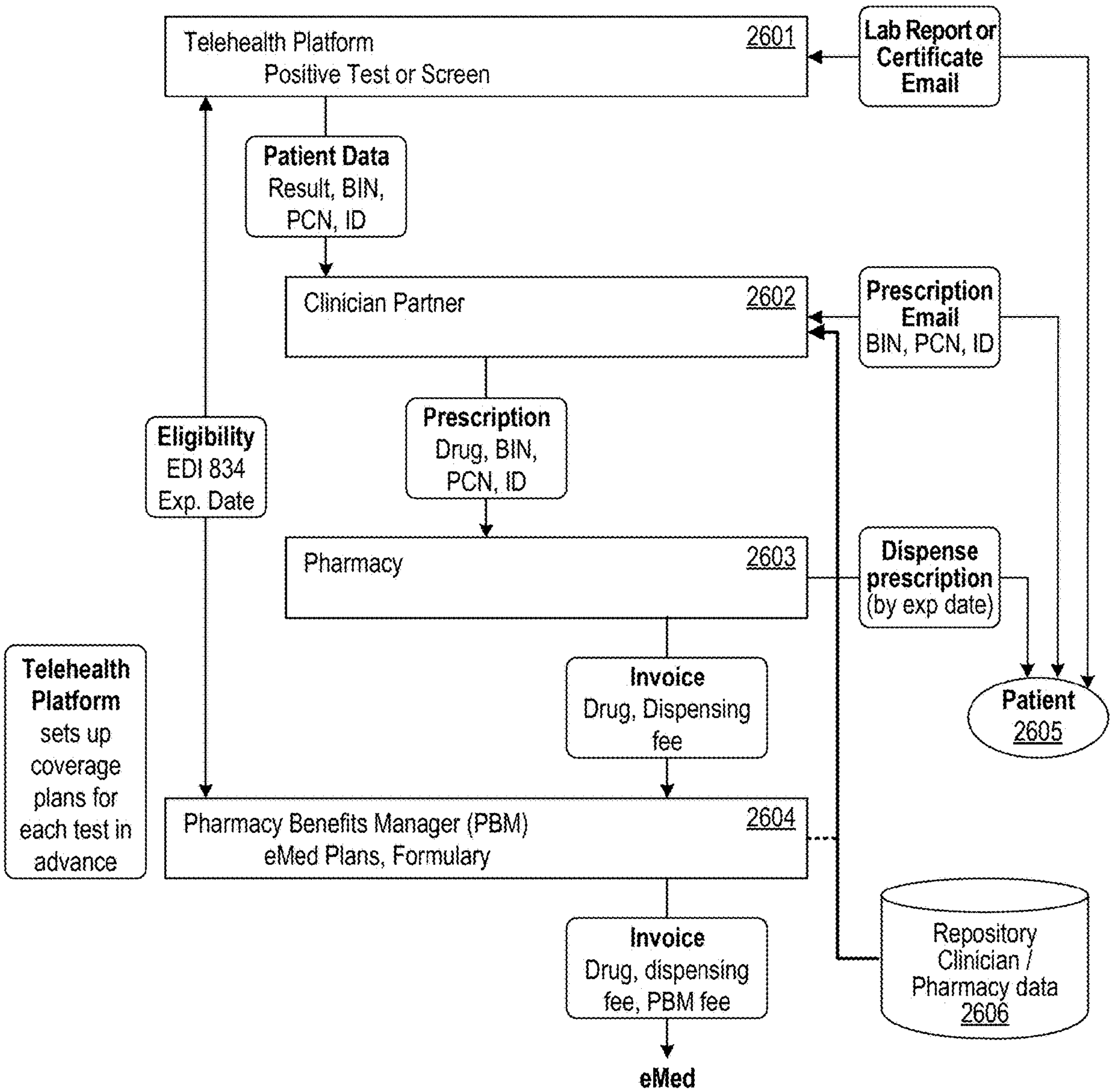
FIG. 26 is a flowchart illustrating a method of providing a microbenefit to a user according to some embodiments.

FIG. 26 is a schematic diagram illustrating a microbenefit policy system. The microbenefit policy can be used for some types of telehealth services such as diagnostic screening, urgent care, on-demand care, and so forth, where a user may need to obtain treatment for an illness or condition. In some cases, a patient, upon being diagnosed with an illness (e.g., testing positive on a test), may not have the resources (e.g., finances, insurance, time to order, transportation options to a pharmacy) to immediately obtain mediation (or otherwise as soon as possible). Such delay can exacerbate the user's health condition and/or cause other problems for the user (e.g., mental anxiety, disruption in life and/or work). Therefore, it can be advantageous to provide a microbenefit policy system that can provide microbenefits or otherwise limited benefits, such as reduced medication cost (e.g., for medication for the first day(s), week(s), month(s), year(s)), deferred payment plans, free or cheaper delivery of medication, etc.

In FIG. 26, a patient 2605 (also referred to herein as a user) takes a diagnostic test. The user receives a positive test result from a telehealth platform 2601. The telehealth platform 2601 provides patient data to a clinician partner 2602. For example, the telehealth platform 2601 can provide the test result and/or other clinically relevant information, biographical information (e.g., name, date of birth, and so forth), and/or benefits information (e.g., processor control number (PCN), prescription BIN number) to the clinician partner 2602. The clinician partner 2602 can communicate with the patient 2605, for example by sending prescription information to the patient 2605, for example via email, text message, or another messaging service. The clinician partner 2602 can communicate with a pharmacy 2603 that can dispense the prescription to the patient 2605. The patient 2605 can be required to pick up the prescription before an expiration date. In some embodiments, the pharmacy 2603 can ship the prescription to the patient 2605. The pharmacy 2603 can send invoice information (e.g., drug, drug price, and any other fees) to a pharmacy benefits manager 2604 (PBM). The testing platform 2601 can send eligibility information to the pharmacy benefits manager 2604, for example an EDI 834 file, expiration information, and so forth. The telehealth platform 2601 can have prearranged plans with the pharmacy benefits manager 2604 for different types of tests, where different prearranged plans can provide coverage for different treatments, can expire after different lengths of time, and so forth. The pharmacy benefits manager 2604 can send invoices to the telehealth platform 2601 for payment. The telehealth platform 2601 can store the data related to the test, patient, clinician partner, pharmacy, pharmacy benefits manager, and so forth in a repository 2606.

Figure 27:
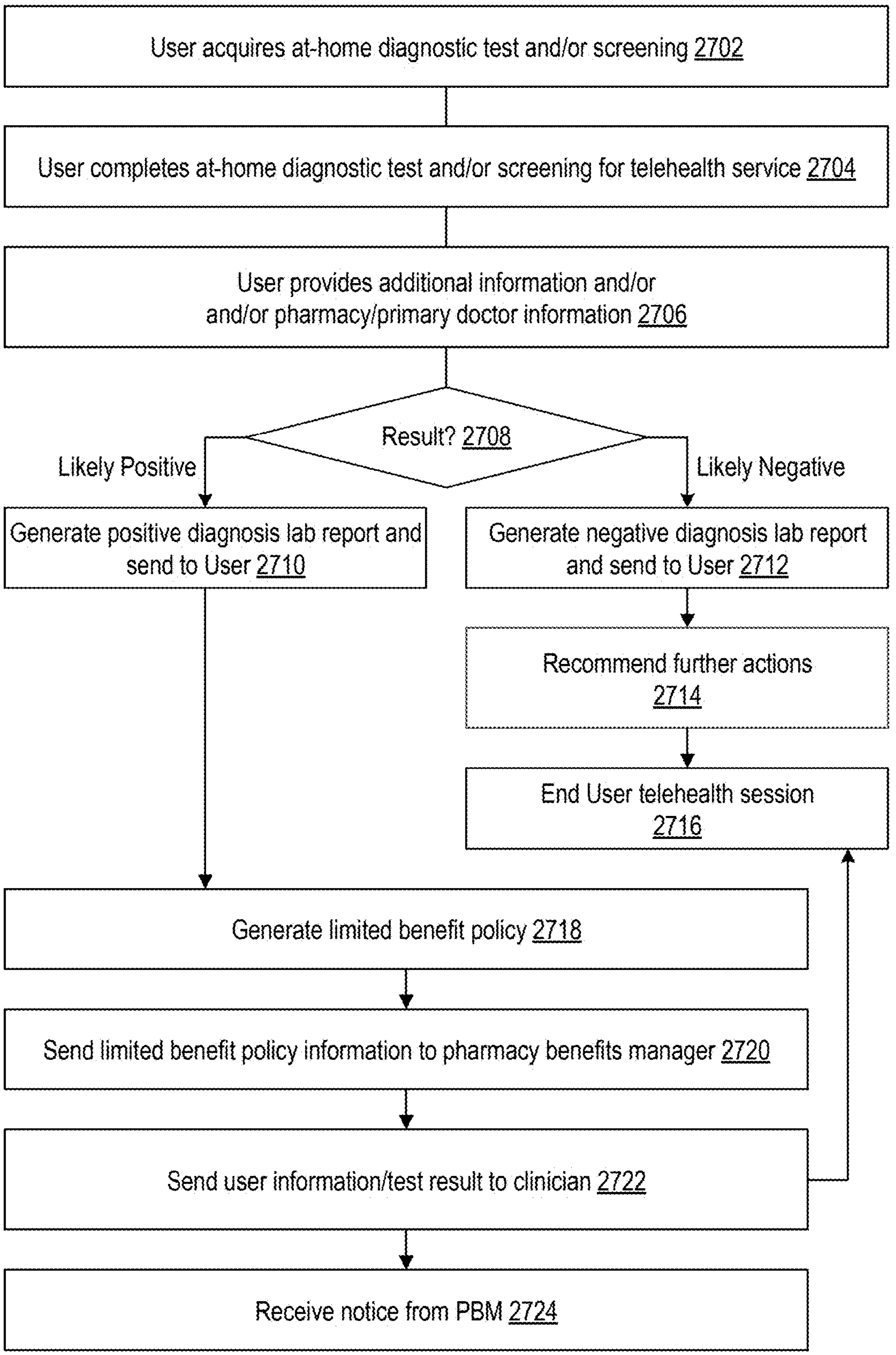
FIG. 27 is a schematic diagram illustrating another microbenefit policy system according to some embodiments.

FIG. 27 is a flowchart illustrating a method of providing a microbenefit to a user. At block 2702, a user can acquire an at-home diagnostic test or screening for an illness. At block 2704, the user can then complete the diagnostic test or screening at home, for example using a telehealth service that can include proctoring. In some embodiments, at block 2706, the user can provide additional personal, demographic, and/or health-related information, for example via surveys, forms, menus, sensors (e.g., thermometers, heart rate sensors, pulse oximeters, electrocardiograms, and so forth), images, additional testing information, diagnostic processes, and so forth, and/or information about the user's insurance, pharmacy, primary doctor, etc. At decision point 2708, the telehealth service can determine an at-home diagnostics result. If the user receives a test result that is likely negative, at block 2712, the telehealth service can generate a negative diagnosis lab report and send the report to the user. In some embodiments, at block 2714, the testing platform can recommend follow-up care which can include, for example, telehealth, in-person healthcare, home remedies (e.g., common, low-risk care such as rest, hydration, and so forth), or any combination thereof. The telehealth system can end the telehealth session at block 2716.

If the user receives a likely positive test result at decision point 2708, at block 2710, the telehealth service can generate a positive diagnosis lab report and send the report to the user. At block 2718, the telehealth service can generate a limited benefit or microbenefit policy, which, as described above, can have limited prescription options and/or limited eligibility duration based on the positive diagnosis. At block 2720, the telehealth service can send the user's limited benefit policy eligibility information (e.g., EDI 834 file, policy expiration date, etc.) to a pharmacy benefits manager. At block 2722, the telehealth service can send the user's diagnosis result, selected identification and/or medically-relevant information, and limited benefit policy information (e.g., processor control number and/or prescription BIN number) to a clinician or clinician group that can prescribe treatment to the user. The user's telehealth session can then be ended at block 2716. At block 2724, the pharmacy benefits manager can send an invoice to the telehealth service. The invoice can example, the pharmacy benefits manager's handling charge, pharmacy dispensing fee, drug information (e.g., drug name, quantity, dose, date dispensed, date delivered to user, etc.), and so forth. In some embodiments, an invoice may include information related to a single user. In some embodiments, the pharmacy benefits manager may batch process information and can send an invoice to the telehealth service that includes charges related to a plurality of users.

Figure 28:
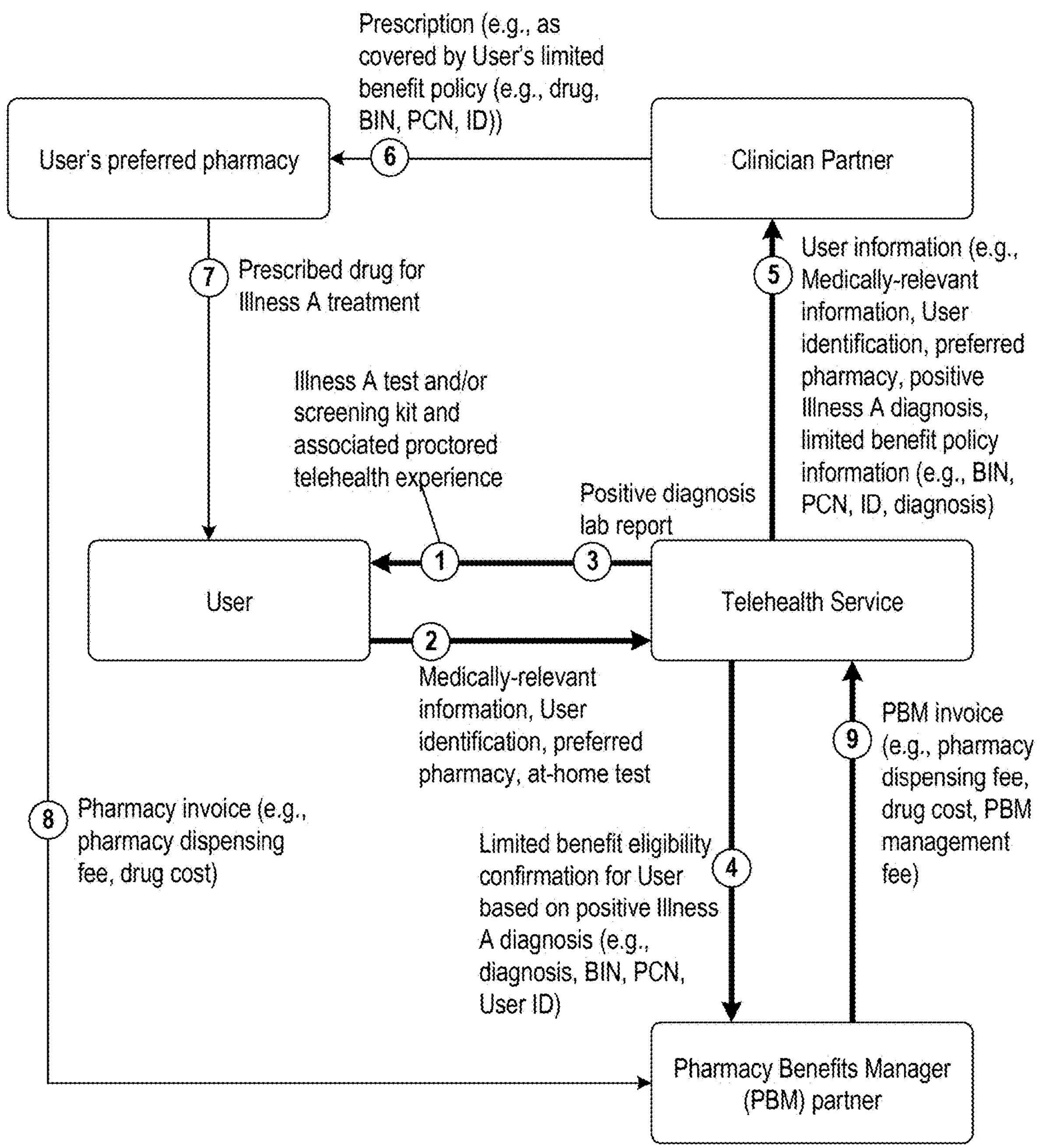
FIG. 28 is a schematic diagram illustrating another microbenefit policy system according to some embodiments.

FIG. 28 is a schematic diagram illustrating another microbenefit policy system according to some embodiments. As indicated by circle 1, the user receives a telehealth test or screening kit and engages in a telehealth experience with a telehealth service, which can be a proctored or non-proctored telehealth session in some embodiments. As indicated by circle 2, medically relevant information about the user, user identification information, pharmacy preferences, and so forth can be received by the telehealth service from the user. As indicated by circle 3, in the illustrated example, the telehealth service can provide a diagnostic report to the user. In the illustrated example, the user receives a positive diagnosis from the telehealth service. If the user receives a negative diagnosis, the telehealth session can end after providing the user with the negative result.

As indicated by circle 4, the telehealth service can communicate with a pharmacy benefits manager (PBM). The communication can include limited benefit eligibility confirmation for the user based upon the positive diagnosis. The communication can include various information such as an EDI 834 file, diagnostic, BIN, PCN, user ID, and so forth. As indicated by circle 5, the telehealth service can provide information about the user (gathered from the user, as indicated by circle 2, and/or from databases, third party data sources, etc.), such as medically relevant information, user identification, preferred pharmacy, test results, limited benefit policy information (e.g., BIN, PCN, ID, diagnosis), and so forth to a clinician partner. The clinician partner can determine whether to prescribe treatment to the user and, if warranted, can prescribe treatment for the user.

As indicated by circle 6, the clinician partner can send prescription information to a pharmacy. For example, if the user has specified a preferred pharmacy, the prescription information can be sent to the user's preferred pharmacy. In some embodiments, the telehealth service can partner with, for example, a mail-order pharmacy which can receive the prescription information. In some embodiments, the telehealth service can provide its own pharmacy services. As indicated by circle 7, the pharmacy can provide the prescribed treatment to the user. In some embodiments, the pharmacy can verify that the user's microbenefits policy has not expired and/or covers the prescribed medication. As indicated by circle 8, the pharmacy can provide an invoice to the PBM. The invoice can include, for example, the pharmacy dispensing fee, drug cost, and other information such as identifying information for the user, policy information, and so forth. As indicated by circle 9, the PBM can, based at least in part on the received invoice from the pharmacy, generate an invoice for the telehealth service. The invoice for the telehealth service can include one or more of a pharmacy dispensing fee, drug cost, PBM management fee, and so forth.

Computer Systems

Figure 29:
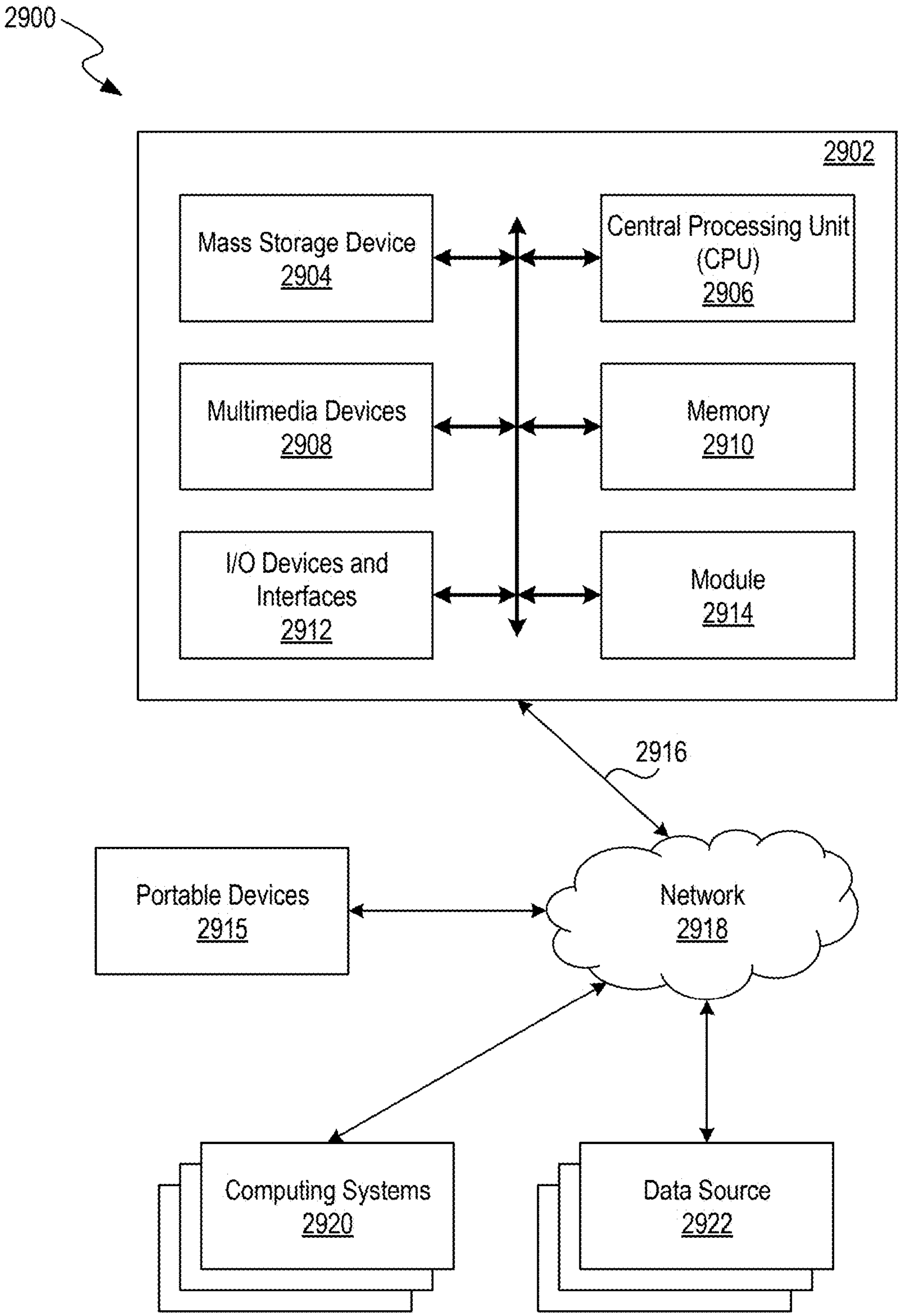
FIG. 29 is a block diagram depicting an embodiment of a computer hardware system on which some embodiments of the present disclosure can be executed.

FIG. 29 is a block diagram 2900 depicting an embodiment of a computer hardware system 2902 configured to run software for implementing the approaches for determining a diagnosis and intervention (e.g., based on a data structure generated for the user) and any systems, methods, and devices disclosed herein. The example computer system 2902 is in communication with one or more computing systems 2920 and/or one or more data sources 2922 via one or more networks 2918. While FIG. 29 illustrates an embodiment of a computing system 2902, it is recognized that the functionality provided for in the components and modules of computer system 2902 may be combined into fewer components and modules, or further separated into additional components and modules.

The computer system 2902 can comprise a module 2914 that carries out the functions, methods, acts, and/or processes described herein. The module 2914 is executed on the computer system 2902 by a central processing unit 2906 discussed further below.

In general, the word "module," as used herein, refers to logic embodied in hardware or firmware or to a collection of software instructions, having entry and exit points. Modules are written in a program language, such as JAVA, C or C++, PYTHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 2902 includes one or more processing units (CPU) 2906, which may comprise a microprocessor. The computer system 2902 further includes a physical memory 2910, such as random-access memory (RAM) for temporary storage of information, a read only memory (ROM) for permanent storage of information, and a mass storage device 2904, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 2902 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 2902 includes one or more input/output (I/O) devices and interfaces 2912, such as a keyboard, mouse, touch pad, and printer. The I/O devices and interfaces 2912 can include one or more display devices, such as a monitor, which allows the visual presentation of data to a user. More particularly, a display device provides for the presentation of GUIs as application software data, and multi-media presentations, for example. The I/O devices and interfaces 2912 can also provide a communications interface to various external devices. The computer system 2902 may comprise one or more multi-media devices 2908, such as speakers, video cards, graphics accelerators, and microphones, for example.

The computer system 2902 may run on a variety of computing devices, such as a server, a Windows server, a Structure Query Language server, a Unix Server, a personal computer, a laptop computer, and so forth. In other embodiments, the computer system 2902 may run on a cluster computer system, a mainframe computer system and/or other computing system suitable for controlling and/or communicating with large databases, performing high volume transaction processing, and generating reports from large databases. The computing system 2902 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 2902 illustrated in FIG. 29 is coupled to a network 2918, such as a LAN, WAN, or the Internet via a communication link 2916 (wired, wireless, or a combination thereof). Network 2918 communicates with various computing devices and/or other electronic devices, such as portable devices 2915. Network 2918 is communicating with one or more computing systems 2920 and one or more data sources 2922. The module 2914 may access or may be accessed by computing systems 2920 and/or data sources 2922 through a web-enabled user access point. Connections may be a direct physical connection, a virtual connection, and other connection type. The web-enabled user access point may comprise a browser module that uses text, graphics, audio, video, and other media to present data and to allow interaction with data via the network 2918.

Access to the module 2914 of the computer system 2902 by computing systems 2920 and/or by data sources 2922 may be through a web-enabled user access point such as the computing systems' 2920 or data source's 2922 personal computer, cellular phone, smartphone, laptop, tablet computer, e-reader device, audio player, or another device capable of connecting to the network 2918. Such a device may have a browser module that is implemented as a module that uses text, graphics, audio, video, and other media to present data and to allow interaction with data via the network 2918.

The output module may be implemented as a combination of an all-points addressable display such as a cathode ray tube (CRT), a liquid crystal display (LCD), a plasma display, or other types and/or combinations of displays. The output module may be implemented to communicate with interfaces 2912 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 2902 may comprise a physical or logical connection established between a remote microprocessor and a mainframe host computer for the express purpose of uploading, downloading, or viewing interactive data and databases on-line in real time. The remote microprocessor may be operated by an entity operating the computer system 2902, including the client server systems or the main server system, an/or may be operated by one or more of the data sources 2922 and/or one or more of the computing systems 2920. In some embodiments, terminal emulation software may be used on the microprocessor for participating in the micro-mainframe link.

In some embodiments, computing systems 2920 who are internal to an entity operating the computer system 2902 may access the module 2914 internally as an application or process run by the CPU 2906.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 2902 may include one or more internal and/or external data sources (for example, data sources 2922). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 2902 may also access one or more databases 2922. The databases 2922 may be stored in a database or data repository. The computer system 2902 may access the one or more databases 2922 through a network 2918 or may directly access the database or data repository through I/O devices and interfaces 2912. The data repository storing the one or more databases 2922 may reside within the computer system 2902.

VIII. CONCLUSION

In the foregoing specification, the systems and processes have been described with reference to specific embodiments thereof. It will, however, be evident that various modifications and changes may be made thereto without departing from the broader spirit and scope of the embodiments disclosed herein. The specification and drawings are, accordingly, to be regarded in an illustrative rather than restrictive sense.

Indeed, although the systems and processes have been disclosed in the context of certain embodiments and examples, it will be understood by those skilled in the art that the various embodiments of the systems and processes extend beyond the specifically disclosed embodiments to other alternative embodiments and/or uses of the systems and processes and obvious modifications and equivalents thereof. In addition, while several variations of the embodiments of the systems and processes have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed systems and processes. Any methods disclosed herein need not be performed in the order recited. Thus, it is intended that the scope of the systems and processes herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

It will also be appreciated that conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the embodiments are not to be limited to the particular forms or methods disclosed, but, to the contrary, the embodiments are to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (for example, as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (for example, as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

What is claimed is:

1. A computer-implemented method, the method comprising:

receiving, from a user device, an image of at least a portion of a thermometer used by a user, wherein the portion of the thermometer includes one or more temperature indicator features;

analyzing the received image to determine an image transformation, wherein analyzing the received image comprises:

identifying an alignment feature in the received image based on at least one of a quality or a number of pixels of the alignment feature by analyzing pixel data of the received image;

aligning the alignment feature in the received image with a corresponding alignment feature of a template such that the alignment feature of the received image positionally align with the corresponding alignment feature of the template to generate a matched image, wherein generating the matched image comprises at least one of rotating, translating, skewing, resizing or cropping;

warping the matched image such that the alignment feature of the received image positionally aligns with the corresponding alignment feature of the template, wherein warping the matched image comprises applying at least one of a perspective warp, a color correction, a contrast modification or a sharpness modification; and determining that the alignment feature of the received image is within a maximum threshold distance from the corresponding alignment feature of the template in the matched image;

determining that the warped image qualifies for interpretation, wherein determining that the warped image qualifies for interpretation comprises determining that an image characteristic of the warped image is above a predetermined threshold corresponding to the image characteristic, wherein the image characteristic comprises at least one of contrast, sharpness, text readability, shape detection, size, or color;

generating an assist image based on the warped image based on the determined image transformation; and determining a temperature of the user based on the generated assist image.

2. The computer-implemented method of claim 1, wherein analyzing the received image further comprises:

determining image information from the received image; and determining that the image information is above a second predetermined threshold.

3. The computer-implemented method of claim 2, wherein the image information comprises a resolution of the received image.

4. The computer-implemented method of claim 1, wherein generating the assist image comprises:

generating a cropped image by cropping the warped image such that the one or more temperature indicator features of the thermometer are in the cropped image;

determining at least one of a white level or a black level of the cropped image;

modifying a dynamic range of the cropped image based on at least one of the determined white level or the determined black level; and generating a balanced image by modifying a white balance of the cropped image based on the determined white level and/or the determined black level.

5. The computer-implemented method of claim 4, wherein generating the assist image further comprises:

determining that a blur level of the balanced image is below a predetermined threshold;

generating a filtered image by applying a filter to the balanced image to preserve edges of one or more features in the balanced image;

generating an enhanced image by modifying one or more color attributes of the filtered image;

extracting a color of each of the one or more temperature indicator features in the enhanced image;

generating a first intermediary assist image from the enhanced image, wherein each of the one or more temperature indicator features are at a corresponding predetermined location in the first intermediary assist image;

generating a second intermediary assist image from a virtual thermometer template including one or more virtual temperature indicator features, wherein each of the one or more virtual temperature indicator features are filled with the corresponding extracted color in the second intermediary assist image; and generating the assist image by combining the first intermediary assist image and the second intermediary assist image.

6. The computer-implemented method of claim 5, wherein the filter comprises a median filter.

7. The computer-implemented method of claim 1, wherein determining the temperature of the user comprises:

determining an array of dominant colors based on the generated assist image, wherein the dominant colors of the array correspond to the one or more temperature indicator features;

generating an input image, wherein the input image comprises a grayscale version of the array of dominant colors;

generating a filter waveform of mean or median contrasts of the one or more temperature indicator features, wherein each of data points of the filter waveform corresponds to a different subset of the one or more temperature indicator features;

generating a filtered waveform by applying a filter to the filter waveform; and determining the temperature of the user by analyzing the filtered waveform.

8. The computer-implemented method of claim 7, wherein generating the filtered waveform comprises:

determining a polynomial fit of the filter waveform; and adding the determined polynomial fit or a negative of the determined polynomial fit to the data points of the filter waveform.

9. The computer-implemented method of claim 7, wherein determining the temperature of the user comprises:

determining a plurality of slopes corresponding to different portions of the filtered waveform between the data points, wherein the temperature of the user corresponds to a temperature value associated with at least one of the data points on the portion with a largest slope.

10. The computer-implemented method of claim 9, further comprising:

performing a confidence check of the determined temperature of the user, wherein performing the confidence check comprises confirming that no other portion of the filtered waveform has a slope within a predetermined threshold of the largest slope.

11. A non-transitory computer readable medium containing program instructions for causing a computer to perform a method comprising:

receiving, from a user device, an image of at least a portion of a thermometer used by a user, wherein the portion of the thermometer includes one or more temperature indicator features;

analyzing the received image to determine an image transformation, wherein analyzing the received image comprises:

identifying an alignment feature in the received image based on at least one of a quality or a number of pixels of the alignment feature by analyzing pixel data of the received image;

aligning the alignment feature in the received image with a corresponding alignment feature of a template such that the alignment feature of the received image positionally align with the corresponding alignment feature of the template to generate a matched image, wherein generating the matched image comprises at least one of rotating, translating, skewing, resizing or cropping;

warping the matched image such that the alignment feature of the received image positionally aligns with the corresponding alignment feature of the template, wherein warping the matched image comprises applying at least one of a perspective warp, a color correction, a contrast modification or a sharpness modification; and determining that the alignment feature of the received image is within a maximum threshold distance from the corresponding alignment feature of the template in the matched image;

determining that the warped image qualifies for interpretation, wherein determining that the warped image qualifies for interpretation comprises determining that an image characteristic of the warped image is above a predetermined threshold corresponding to the image characteristic, wherein the image characteristic comprises at least one of contrast, sharpness, text readability, shape detection, size, or color;

generating an assist image based on the warped image based on the determined image transformation; and determining a temperature of the user based on the generated assist image.

12. The non-transitory computer readable medium of claim 11, wherein analyzing the received image further comprises:

determining image information from the received image; and determining that the image information is above a predetermined threshold.

13. The non-transitory, computer readable medium of claim 12, wherein the image information comprises a resolution of the received image.

14. The non-transitory computer readable medium of claim 11, wherein generating the assist image comprises:

generating a cropped image by cropping the warped image such that the one or more temperature indicator features of the thermometer are in the cropped image;

determining at least one of a white level or a black level of the cropped image;

modifying a dynamic range of the cropped image based on at least one of the determined white level or the determined black level; and generating a balanced image by modifying a white balance of the cropped image based on the determined white level and/or the determined black level.

15. The non-transitory computer readable medium of claim 14, wherein generating the assist image further comprises:

determining that a blur level of the balanced image is below a predetermined threshold;

generating a filtered image by applying a filter to the balanced image to preserve edges of one or more features in the balanced image;

generating an enhanced image by modifying one or more color attributes of the filtered image;

extracting a color of each of the one or more temperature indicator features in the enhanced image;

generating a first intermediary assist image from the enhanced image, wherein each of the one or more temperature indicator features are at a corresponding predetermined location in the first intermediary assist image;

generating a second intermediary assist image from a virtual thermometer template including one or more virtual temperature indicator features, wherein each of the one or more virtual temperature indicator features are filled with the corresponding extracted color in the second intermediary assist image; and generating the assist image by combining the first intermediary assist image and the second intermediary assist image.

16. The non-transitory computer readable medium of claim 15, wherein the filter comprises a median filter.

17. The non-transitory computer readable medium of claim 11, wherein determining the temperature of the user comprises:

determining an array of dominant colors based on the generated assist image, wherein the dominant colors of the array correspond to the one or more temperature indicator features;

generating an input image, wherein the input image comprises a grayscale version of the array of dominant colors;

generating a filter waveform of mean or median contrasts of the one or more temperature indicator features, wherein each of data points of the filter waveform corresponds to a different subset of the one or more temperature indicator features;

generating a filtered waveform by applying a filter to the filter waveform; and determining the temperature of the user by analyzing the filtered waveform.

18. The non-transitory computer readable medium of claim 17, wherein generating the filtered waveform comprises:

determining a polynomial fit of the filter waveform; and adding the determined polynomial fit or a negative of the determined polynomial fit to the data points of the filter waveform.

19. The non-transitory computer readable medium of claim 17, wherein determining the temperature of the user comprises:

determining a plurality of slopes corresponding to different portions of the filtered waveform between the data points, wherein the temperature of the user corresponds to a temperature value associated with at least one of the data points on the portion with a largest slope.

20. The non-transitory computer readable medium of claim 19, wherein the method further comprises:

performing a confidence check of the determined temperature of the user, wherein performing the confidence check comprises confirming that no other portion of the filtered waveform has a slope within a predetermined threshold of the largest slope.

* * * * *